United States Patent [19]  [11] 3,932,425
Lednicer  [45] Jan. 13, 1976

[54] BENZOSPIRAN DERIVATIVES
[75] Inventor: Daniel Lednicer, Portage, Mich.
[73] Assignee: The Upjohn Company, Kalamazoo, Mich.
[22] Filed: Apr. 12, 1974
[21] Appl. No.: 460,449

[52] U.S. Cl.... 260/293.62; 260/239 B; 260/326.5 J; 260/326.8; 260/326.81; 260/488 CD; 260/562 R; 260/570.5 CA; 424/244; 424/267; 424/274; 424/311; 424/324; 424/330
[51] Int. Cl.² ................................ C07D 295/02
[58] Field of Search ...... 260/239 B, 293.62, 293.66, 260/326.8, 326.81, 562 R, 570.5 CA

[56] References Cited
UNITED STATES PATENTS
3,097,136  9/1963  Godefroi et al. ............... 167/65
3,651,142  3/1972  Freedman ................. 260/570.5 CA Primary Examiner—G. Thomas Todd
Attorney, Agent, or Firm—John T. Reynolds; William A. Hodes

[57] ABSTRACT
This invention relates to novel benzospiran derivatives embraced by the formula

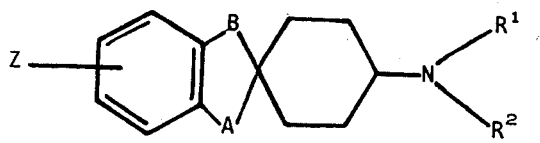

wherein the sum of A and B is at least the integer 2; A is selected from the group consisting of —$(CH_2)_n$— wherein n is 1 through 5 and —$(C_nH_{2n-2}XY)$— wherein X is selected from the group consisting of hydroxy, acetoxy, amino and acetamido and Y is hydrogen, and X when taken together with Y is selected from the group consisting of =O and =$CR^3R^4$ wherein $R^3$ and $R^4$ are selected from the group consisting of hydrogen and lower alkyl of 1 through 3 carbon atoms; B is absent or —$(CH_2)_n$— wherein n is 1 through 3; $R^1$ is selected from the group consisting of hydrogen and lower alkyl of 1 through 3 carbon atoms; $R^2$ is selected from the group consisting of hydrogen, lower alkyl of 1 through 3 carbon atoms,

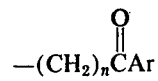

wherein n is 2 through 5 and Ar is phenyl having zero through three substituents selected from the group consisting of lower alkyl of 1 through 3 carbon atoms, lower alkoxy of 1 through 3 carbon atoms, bromine, chlorine and fluorine; $R^1$ and $R^2$ taken together with —N< is a saturated heterocyclic amino radical selected from the group consisting of unsubstituted and substituted pyrrolidino, piperidino, and hexamethylenimino; Z is selected from the group consisting of hydrogen, lower alkyl of 1 through 3 carbon atoms, lower alkoxy of 1 through 3 carbon atoms, nitro, amino, monoalkylamino of 1 through 3 carbon atoms, acylamido of 1 through 4 carbon atoms, bromine, chlorine and fluorine; and a pharmacologically acceptable acid addition salt thereof. It also relates to intermediates and processes for the preparation of the aforesaid novel compounds (1) and novel derivatives thereof. The administration to humans and animals of the novel compounds (1) depresses their central nervous systems and lowers their blood pressures.

10 Claims, No Drawings

BENZOSPIRAN DERIVATIVES

BRIEF SUMMARY OF THE INVENTION

This invention relates to novel organic compounds, particularly novel benzospiran derivatives embraced by the formula

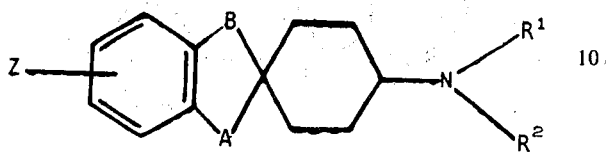

wherein the sum of A and B is at least the integer 2; A is selected from the group consisting of $-(CH_2)_n-$ wherein n is 1 through 5 and $-(C_nH_{2n-2}XY)-$ wherein X is selected from the group consisting of hydroxy, acetoxy, amino and acetamido and Y is hydrogen, and X when taken together with Y is selected from the group consisting of =O and =CR$^3$R$^4$ wherein R$^3$ and R$^4$ are selected from the group consisting of hydrogen and lower alkyl of 1 through 3 carbon atoms; B is absent or $-(CH_2)_n-$ wherein n is 1 through 3; R$^1$ is selected from the group consisting of hydrogen and lower alkyl of 1 through 3 carbon atoms; R$^2$ is selected from the group consisting of hydrogen, lower alkyl of 1 through 3 carbon atoms,

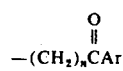

wherein n is 2 through 5 and Ar is phenyl having zero through three substituents selected from the group consisting of lower alkyl of 1 through 3 carbon atoms, lower alkoxy of 1 through 3 carbon atoms, bromine, chlorine and fluorine; R$^1$ and R$^2$ taken together with $-N<$ is a saturated heterocyclic amino radical selected from the group consisting of unsubstituted and substituted pyrrolidino, piperidino, and hexamethylenimino; Z is selected from the group consisting of hydrogen, lower alkyl of 1 through 3 carbon atoms, lower alkoxy of 1 through 3 carbon atoms, nitro, amino, monoalkylamino of 1 through 3 carbon atoms, acylamido of 1 through 4 carbon atoms, bromine, chlorine and fluorine; and pharmacologically acceptable acid addition salts thereof.

The preferred compounds of this invention embraced by Formula I, immediately above, are those having the formula

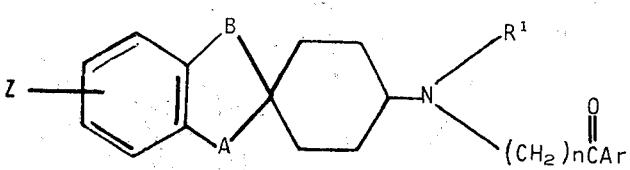

which are inclusive of those represented by the formulae

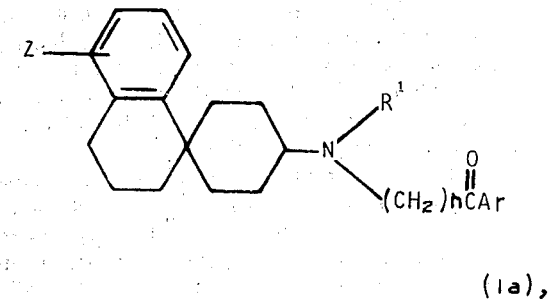

(Ia),

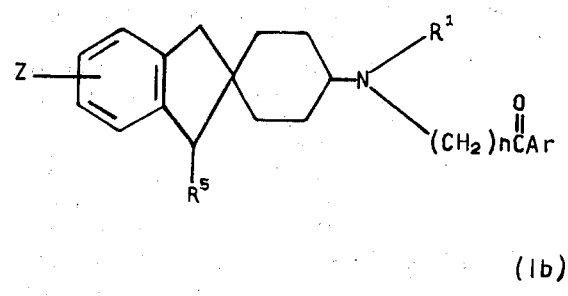

(Ib)

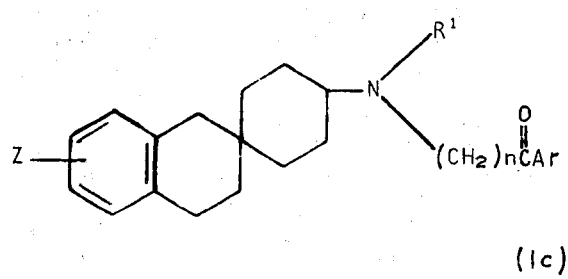

(Ic)

wherein A, B, Ar, n, R$^1$ and Z have the same meaning as above and R$^5$ is selected from the group consisting of hydrogen, hydroxy and methylene; and a pharmacologically acceptable acid addition salt thereof.

Examples of Ar are phenyl, m-chlorophenyl, p-fluorophenyl, m-ethylphenyl, o-methylphenyl, 3,4-dimethoxyphenyl, 2,4-dimethylphenyl, 2-bromo-5-ethylphenyl, 2-chloro-3,5-dipropylphenyl and 2,4,6-trichlorophenyl. Examples of lower alkyl of 1 through 3 carbon atoms are methyl, ethyl, propyl and isopropyl. Examples of lower alkoxy of 1 through 3 carbon atoms are methoxy, ethoxy, propoxy, and isopropoxy. Examples of unsubstituted and substituted pyrrolidino, piperidino and hexamethylenimino are pyrrolidino, 2-methylpyrrolidino, piperidino, 2-ethylpiperidino, hexamethylenimino, 3-methoxyhexamethylenimino and 2-ethyl-4-methylhexamethylenimino. Examples of

is phenyl having from zero through three substituents selected from the group consisting of fluorine, chlorine, bromine, lower alkyl of 1 through 3 three carbon atoms and lower alkoxy of 1 through 3 carbon atoms, are: 4-oxo-4-(p-fluorophenyl)-butyl, 4-oxo-4-(2-chloro-1-methylphenyl)butyl, 4-oxo-4-phenylbutyl, 4-oxo-4-(p-tolyl)butyl, 4-oxo-4-(p-methoxyphenyl)butyl, 4-oxo-4-(p-chlorophenyl)butyl, 4-oxo-(2-bromo-4-chlorophenyl)butyl, 3-oxo-3-(p-bromophenyl)propyl, 5-oxo-4-(o-ethoxyphenyl)pentyl, and the isomeric forms thereof. Examples of monoalkylamino of 1 through 3 carbon atoms are methylamino, ethylamino, propylamino and isopropylamino. Examples of acylamido of 1 through 4 carbon atoms are formylamido, acetamido, propionamido and isopropionamido.

The novel benzospiran compounds of Formula I exist either in the non-protonated (free base) form or in the protonated (acid addition salt) form, depending on the pH of the environment. They form stable protonates, i.e., acid addition salts, on neutralization of the free base form with suitable acids, for example, hydrochloric, hydrobromic, sulfuric, phosphoric, nitric, acetic, propionic, palmitic, benzoic, salicylic, hexynoic, phenylbutyric, naphthoic, glycolic, succinic, nicotinic, tartaric, maleic, malic, pamoic, methanesulfonic, citric and lactic acids, and the like. Conversely, the free base of the novel compounds of Formula I can be obtained from a salt (e.g., from the hydrochloride or sulfate salts) by neutralization with a base such as sodium hydroxide, extracting with an immiscible solvent, for example chloroform, drying the extract, for example, with anhydrous sodium sulfate, and removing the solvent by evaporation.

The novel compounds of generic Formula I, above, include those of three types, namely, 3',4'-dihydrospiro[cyclohexane-1,1'(2'H)-naphthalene]s having the general structure

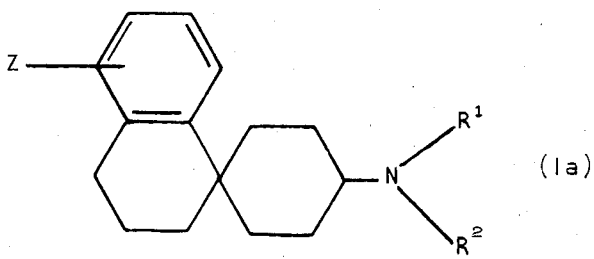

(Ia)

spiro[cyclohexane-1,2'-indan]s of the general structure

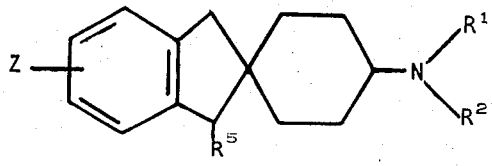

(Ib)

and spiro[cyclohexane-1,2'-tetralin]s of the general structure

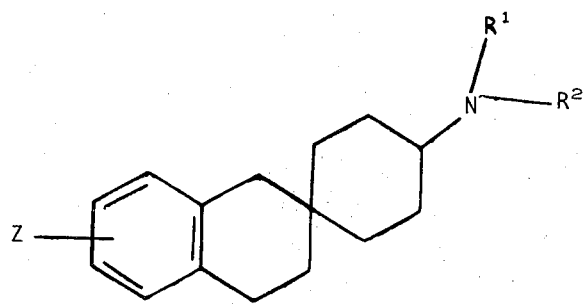

(Ic)

wherein $R^1$, $R^2$ and Z have the same meaning as above and $R^5$ is selected from the group consisting of hydrogen, hydroxy and methylene.

The novel compounds of Formula I (a, b and c), above, and intermediates therefor are prepared in accordance with the procedures of Processes A, B and C, respectively, described below.

Process A

The following sequence of formulae illustratively represents procedures for the preparation of compounds of Formula I(a).

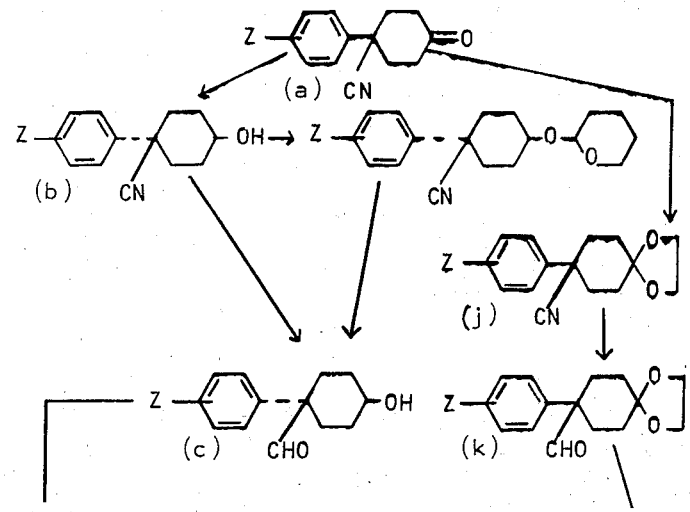

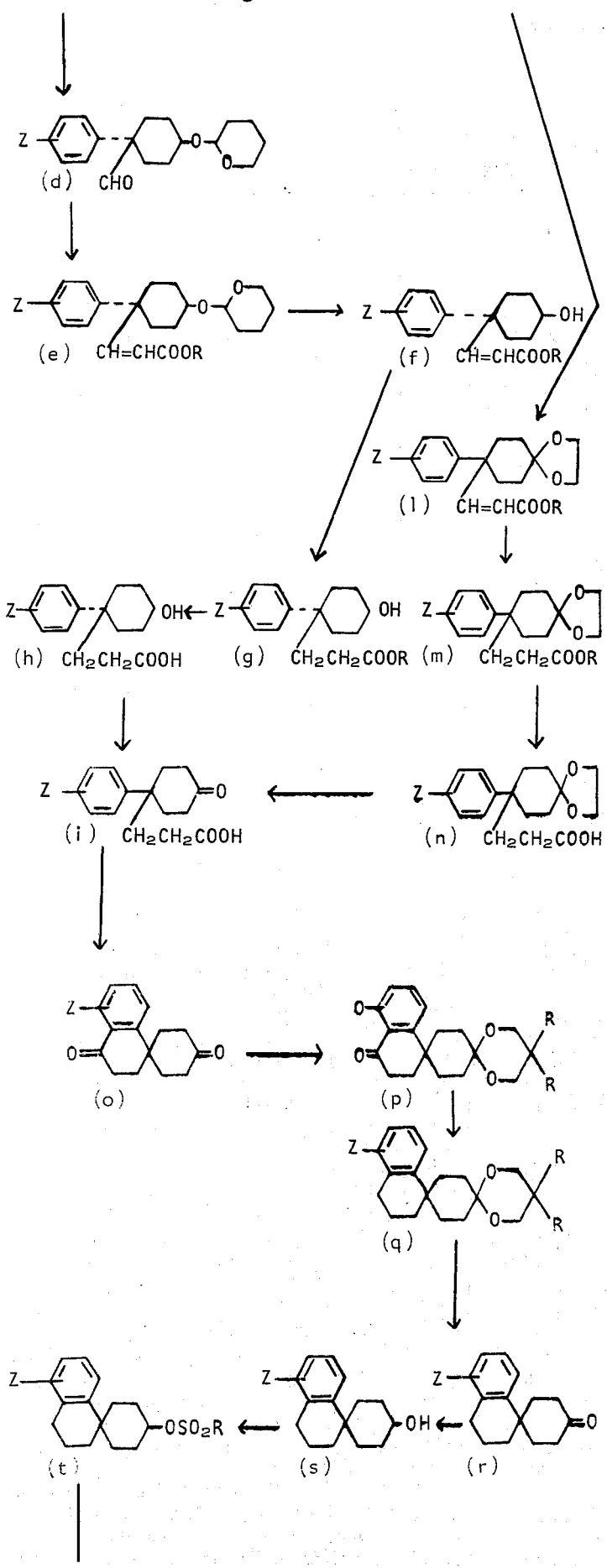

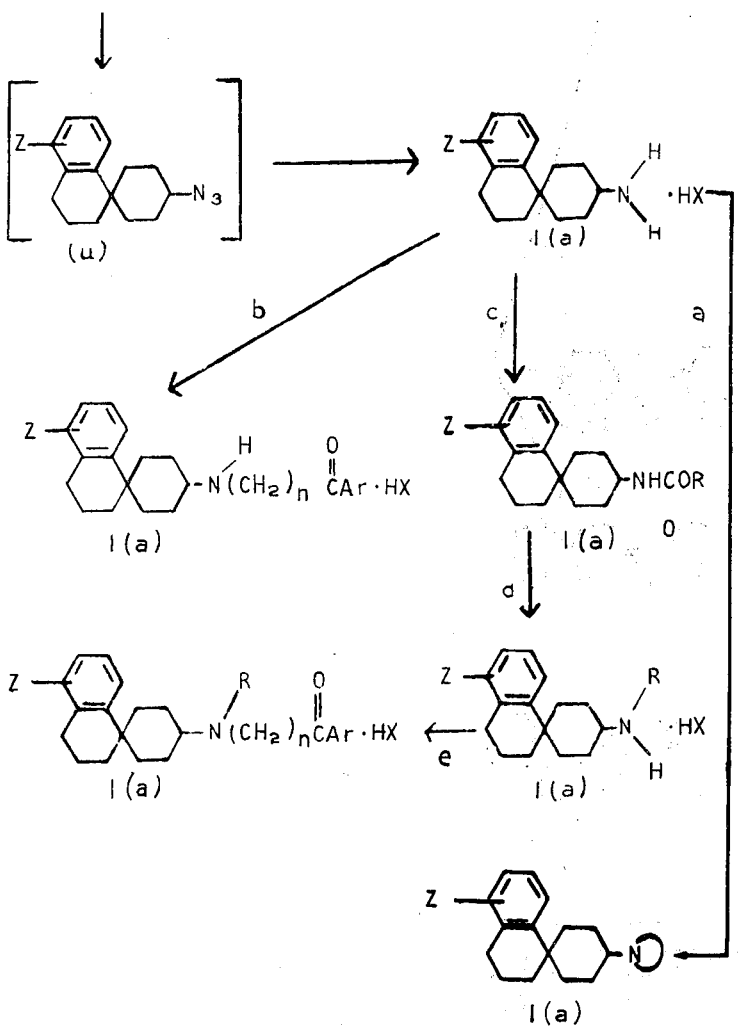

wherein Ar, n and Z have the same meaning as above, R is lower alkyl of 1 through 3 carbon atoms, the symbol —N◯ represents a saturated heterocyclic amino radical selected from the group consisting of unsubstituted and substituted pyrrolidino, piperidino and hexamethyleneimino and X is selected from the group consisting of chlorine, bromine and an anion of a pharmacologically acceptable acid addition salt.

The compounds embraced by Formula I(a) of the flowsheet designated Process A, above, are prepared by the procedures indicated therein, employing the methods and reactions described below.

1. The first step of the process comprises reducing a known 4-cyano-4-phenylcyclohexanone (a), e.g., with sodium borohydride (in a solvent such as tetrahydrofuran) at low temperature, to yield a corresponding 4-cyano-4-phenylcyclohexanol (b).

2. A thus produced 4-cyano-4-phenylcyclohexanol (b) obtained in step (1) is directly reduced, e.g., with lithium aluminum hydride (in a solvent such as tetrahydrofuran) at elevated (reflux) temperature, to give a corresponding 4-hydroxy-1-phenyl-1-cyclohexanecarboxaldehyde (c). This compound is also prepared via the tetrahydropyranyl ether of (b).

3. A 4-hydroxy-1-phenyl-1-cyclohexanecarboxaldehyde (c) produced in step (2) is first converted to its corresponding tetrahydropyranyl ether (d) (e.g., by mixing it will dihydropyran in the presence of an acid catalyst such as p-toluenesulfonic acid in a solvent such as ether), then the formyl function of said ether (d), alkylated via the Wittig reaction (e.g., by reacting it with a mixture of a trialkylphosphonoacylate, in a solvent such as tetrahydrofuran, and sodium hydride, followed by heating at reflux) to give a corresponding alkyl-4-hydroxy-1-phenylcyclohexaneacrylate tetrahydropyranyl ether (e), followed by hydrolysis of said compound (e); for example, with an alkanol (such as methanol) acidified with an acid such as hydrochloric acid, to give a corresponding alkyl-4-hydroxy-1-phenylcyclohexaneacrylate (f).

4. An alkyl-4-hydroxy-1-phenylcyclohexaneacrylate (f) prepared in step (3) is reduced catalytically (e.g., with hydrogen in the presence of palladium on carbon), to give a corresponding alkyl-4-hydroxy-1-phenylcyclohexane-3-propionate (g).

5. An alkyl-4-hydroxy-1-phenylcyclohexane-3-propionate (g) obtained in step (4) is hydrolyzed, e.g., by heating it at reflux with an alkali metal hydroxide (such as sodium hydroxide) in an alkanol (such as methanol), to yield a corresponding 4-hydroxy-1-phenylcyclohexane-3-propionic acid (h).

6. The next step of the process comprises oxidizing the 4-hydroxyl function of a 4-hydroxy-1-phenylcyclohexane-3-propionic acid (h) produced in step (5), e.g., with Jones reagent (chromium trioxide — sulfuric acid), preferably at ice bath temperature, to yield a corresponding 4-oxo-1-phenylcyclohexane 3-propionic acid (i).

The compounds embraced by intermediate (i) can also be prepared by another method, namely, via alkylene ketals, as follows:

1'. A 4-cyano-4-phenylcyclohexanone (a) is ketalized, e.g., by heating (at reflux) in benzene with an alkylene glycol (in the presence of a catalyst such as p-toluenesulfonic acid), to yield a corresponding 4-cyano-4-phenylcyclohexanone alkylene ketal (j).

2'. A 4-cyano-4-phenylcyclohexanone alkylene ketal (j) produced in step (1') is converted with about 0.5 mole equivalent of lithium aluminum hydride (in a solvent such as tetrahydrofuran) at room temperature to a corresponding imine, followed by its hydrolysis (e.g., in a solvent such as tetrahydrofuran with an acid such as hydrochloric acid), to yield a corresponding 4-oxo-1-phenylcyclohexanecarboxaldehyde 4-alkylene ketal (k).

3'. A 4-oxo-1-phenylcyclohexanecarboxaldehyde 4-alkylene ketal (k) produced in step (2') is alkylated via the Wittig reaction (e.g., by reacting it with a mixture of a trialkylphosphonoacetate, in a solvent such as tetrahydrofuran, and sodium hydride, followed by heating at reflux) to give a corresponding alkyl-4-oxo-1-phenylcyclohexaneacrylate alkylene ketal (l).

4'. An alkyl-4-oxo-1-phenylcyclohexaneacrylate alkylene ketal (l) prepared in step (3') is reduced catalytically (e.g., with hydrogen in the presence of palladium on carbon), to give a corresponding alkyl-4-oxo-1-phenylcyclohane-3-propionate alkylene ketal (m).

5'. An alkyl-4-oxo-1-phenylcyclohexane-3-propionate alkylene ketal (m) obtained in step (4') is hydrolyzed, e.g., by heating it at reflux with an alkali metal hydroxide (such as sodium hydroxide) in an alkanol (such as methanol), to give a corresponding 4-oxo-1-phenylcyclohexane-3-propionic acid alkylene ketal (n).

6'. In this step, the alkylene ketol protective group of a 4-oxo-1-phenylcyclohexane-3-propionic acid alkylene ketal (n) produced in step (5') is removed by employing conventional reagents and procedures, e.g., by stirring an aforesaid compound with a dilute aqueous acid (e.g., hydrochloric) in acetone at moderate (room) temperature for a long (6 to 60 hour) period, to give a corresponding 4-oxo-1-phenylcyclohexane-3-propionic acid (i), also produced by the method ending with step (6), above.

7. A 4-oxo-1-phenylcyclohexane-3-propionic acid (i) prepared in step (6) or (6') is cyclized, e.g., by allowing it to stand at room temperature for from about 15 to about 80 hours with liquid hydrogen fluoride, to yield a corresponding spiro[cyclohexane-1,1'(2'H)-naphthalene]-4,4'(3'H)-dione (o).

8. A spiro[cyclohexane-1,1'(2'H)-naphthalene]-4,4'(3'H)-dione (o) prepared in step (7) is monoketalized at the non-conjugated least hindered carbonyl function, e.g., by heating (at reflux) in a solvent such as benzene with an alkylene glycol (in the presence of a catalyst such as p-toluenesulfonic acid), to yield a corresponding spiro[cyclohexane-1,1'(2'H)-naphthalene]-4,4'(3'H)-dione, 4-(2,2-dialkyltrimethylene ketal) (p).

9. A spiro[cyclohexane-1,1'(2'H)-naphthalene]-4,4'(3'H)-dione, 4-(2,2-dialkyltrimethylene ketal (p) produced in step (8) is reduced at the 4'-position, e.g., by long (about 12 to about 18 hours) heating (at reflux) with hydrazine hydrate and an alkali metal base such as sodium hydroxide in a solvent such as an alkylene glycol (e.g., ethylene glycol) to give a corresponding 3',4'-dihydrospiro[cyclohexane-1,1'(2'H)-naphthalene]-4-one, 2,2-dialkyltrimethylene ketal (g).

10. In this step, a 3',4'-dihydrospiro[cyclohexane-1,1'(2'H)-naphthalene]-4-one, 2,2-dialkyltrimethylene ketal (q) prepared in step (9) has its ketal protective group removed by hydrolysis, e.g., by mixing it with an acid (such as hydrochloric acid) in a solvent (such as acetone) at moderate (room) temperature for from about 2 to about 10 hours, to yield a corresponding 3',4'-dihydrospiro[cyclohexane-1,1'(2'H)-naphthalen]-4-one (r).

11. A 3',4'-dihydrospiro[cyclohexane-1,1'(2'H)-naphthalen]-4-one (r) produced in step (10) has its 4-keto function reduced, e.g., by mixing said compound in a solvent such as ethanol with sodium borohydride at moderate (room) temperature for from about 3 to about 8 hours, to produce a corresponding 3',4'-dihydrospiro[cyclohexane-1,1'(2'H)-naphthalen]-4-ol (s).

12. Letting stand (preferably at low temperature for from about 3 to about 14 hours) a mixture of a 3',4'-dihydrospiro[cyclohexane-1,1'-(2'H)-naphthalen]-4-ol (s) obtained in step (11) in an amine base (e.g., pyridine) and a lower alkyl sulfonyl halide (such as methanesulfonyl chloride), yields a corresponding 3',4'-dihydrospiro[cyclohexane-1,1'(2'H)naphthalen]-4-ol lower alkyl sulfonate (t).

13. A 3',4'-dihydrospiro[cyclohexane-1,1'(2'H)-naphthalen]-4-ol alkyl sulfonate (t) resulting from step (12) and sodium azide in a solvent such as dimethylformamide, on heating (at from about 65° to about 100° C. for from about 4 to about 24 hours), yields a corresponding 3',4'-dihydrospiro[cyclohexane 1,1'(-2'H)-1,1'(2'H)-naphthalen]-4-ylazide (u).

14. A 3',4'-dihydrospiro[cyclohexane-1,1'(2'H)-1,1'(2'H)-naphthalen]-4-ylazide (u) obtained in step (13) on reduction of its azido function, e.g., by reacting said compound with lithium aluminum hydride in a solvent such as tetrahydrofuran at moderate (room) temperature for from about 3 to about 10 hours, yields a corresponding 3',4'-dihydrospiro[cyclohexane-1,1'(-2'H)-naphthalen]-4-ylamine [I(a)] in its free base form. On treating an ether extract of a thus produced compound with an ethereal solution of a suitable (pharmacologically acceptable) acid, its acid addition salt form is obtained.

The free base or acid addition salt forms of the 3',4'-dihydrospiro[cyclohexane-1,1'(2'H)-naphthalen]-4-ylamines [I(a)] obtained as in step (14), above, are employed as starting materials for producing a variety of derivatives thereof, for example, in accordance with the methods described in (a) through (e) that follow.

a. Heating (e.g., under reflux for from about 8 to about 24 hours) a 3',4'-dihydrospiro[cyclohexane-1,1'(2'H)-naphthalen]-4-ylamine [I(a)] obtained in step (14) with a dihaloalkane, gives a corresponding (1-single ring nitrogen containing heterocyclo)-3',4'-dihydrospiro-(cyclohexane-1,1'(2'H)-naphthalen)-4-yl [I(a)], which on dissolving in ether and treating with an ethereal solution of an appropriate acid, yields the corresponding acid addition salt. For example, heating a 3',4'-dihydrospiro[cyclohexane-1,1'(2'H)-naphthalen]-4-ylamine [I(a)] with 1,5-diiodopentane, 1,4-dibromobutane or 1,6-diiodohexane, yields, respectively a corresponding 1-[3',4'-dihydrospiro(cyclohexane-1,1′(2′H)-naphthalen)-4-yl]piperidine [I(a)], a 1-[3′,4′-dihydrospiro(cyclohexane-1,1′(2′H)-naphthalen)-4-yl)pyrrolidine [I(a)] or a 1-[3′,4′-dihydrospiro(cyclohexane-1,1′(2′H)-naphthalen)-4-yl]hexamethyleneimine [I(a)], which can be converted to their acid addition salts in the manner described in the immediately preceding sentence.

b. The production of a compound selected from the group consisting of the free bases and acid addition salts of a 4-[3′,4′-dihydrospiro[cyclohexane-1,1′(-2′H)-naphthalen]-4-ylamino]alkanophenone of the formula

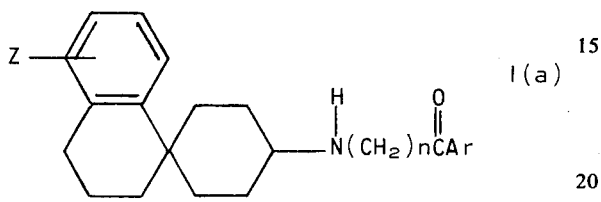

I(a)

wherein Ar, n and Z have the same meaning as above, comprises reacting (in the presence of an alkali metal iodide and an alkali metal carbonate) a corresponding compound obtained as in step (14) selected from the group consisting of the free bases and acid salts of a compound of the formula

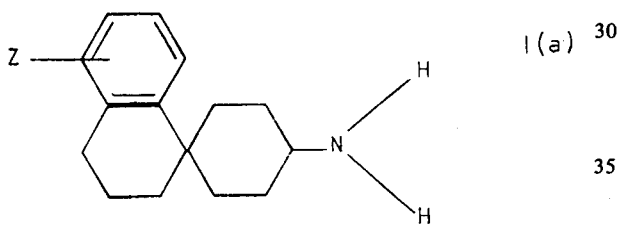

I(a)

wherein Z has the same meaning as above, with a corresponding compound of the formula

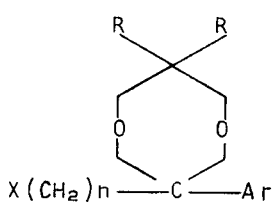

wherein Ar, R and n have the same meaning as above and X is selected from the group consisting of chlorine and bromine, followed by hydrolyzing (i.e., deketalizing) a thus produced compound, e.g., with aqueous acid in an alkanol.

c. Reacting a 3′,4′-dihydrospiro[cyclohexane-1,1′-(2′H)-naphthalen]-4-ylamine [I(a)] obtained as in step (14), in an amine base (such as pyridine) in the cold with a lower alkyl haloformate (e.g., ethyl chloroformate, methylbromoformate or propyl chloroformate), yields a corresponding lower alkyl 3′,4′-dihydrospiro[cyclohexane-1,1′(2′H)-naphthalene]-4-carbamate of the formula

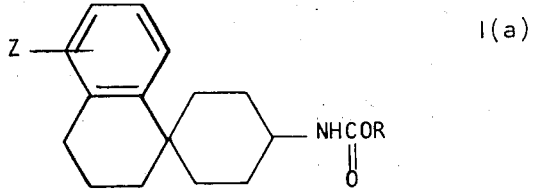

I(a)

wherein R and Z have the same meaning as above.

d. A lower alkyl 3′,4′-dihydrospiro[cyclohexane1,-1′(2′H)-naphthalene]-4-carbamate I(a), prepared as in (c) immediately above, is reduced, for example, by heating it in a solvent such as tetrahydrofuran [e.g., under reflux for from about 8 to about 24 hours] with lithium aluminum hydride, to yield a corresponding 3′,4′-dihydrospiro[cyclohexane-1,1′(2′H)-naphthalen]-4-yl-N-lower alkylamine [I(a)], which on dissolving in ether and treating with an ethereal solution of an appropriate acid gives a corresponding acid addition salt thereof.

e. Following the procedure of (b), above, but substituting as starting material the free base or acid addition salt of a 3′,4′-dihydrospiro[cyclohexane-1,1′-(2′H)-naphthalen]-4-yl-N-lower alkylamine [I(a)], obtained as in (d) immediately above, yields a corresponding 4-[3′,4′-dihydrospiro[cyclohexane-1,1′(2′H)-naphthalen]-2 through 5-yl-N-lower alkylamino]alkanophenone [I(a)], or an acid addition salt thereof.

Process B

The following sequence of formulae illustratively represents procedures for the preparation of compounds of Formulae I(b).

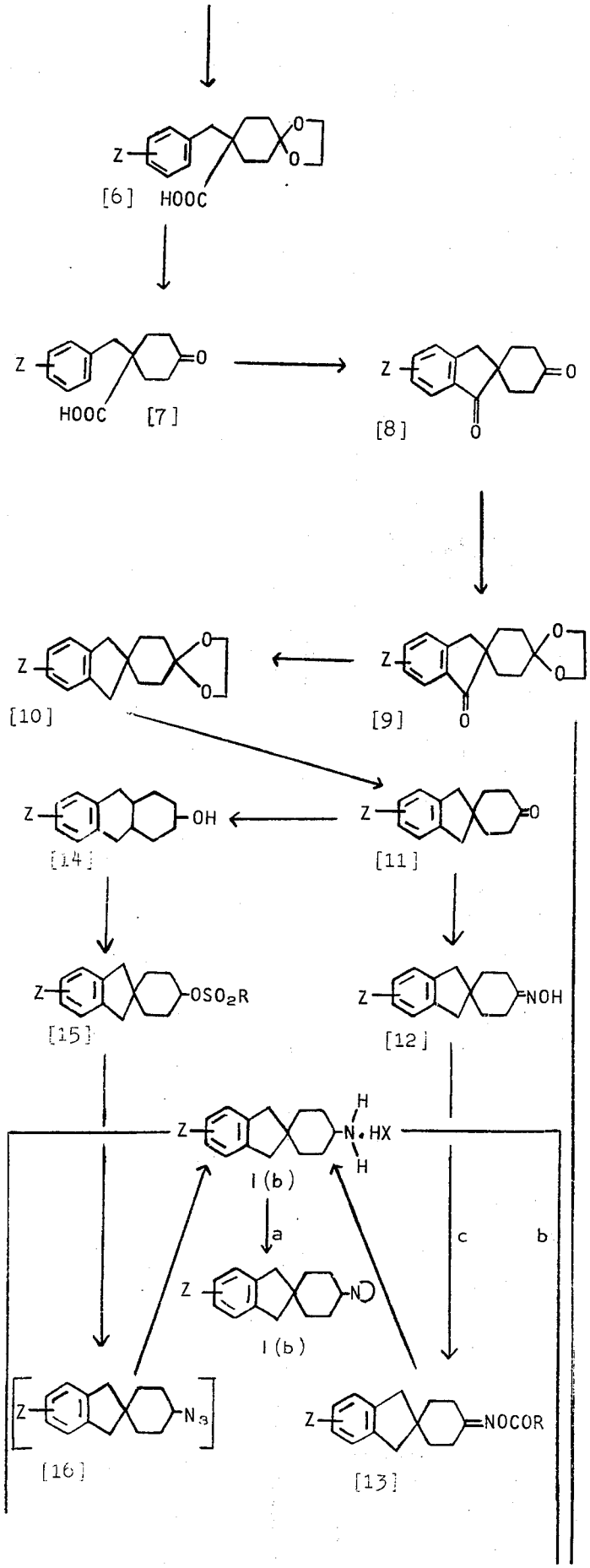

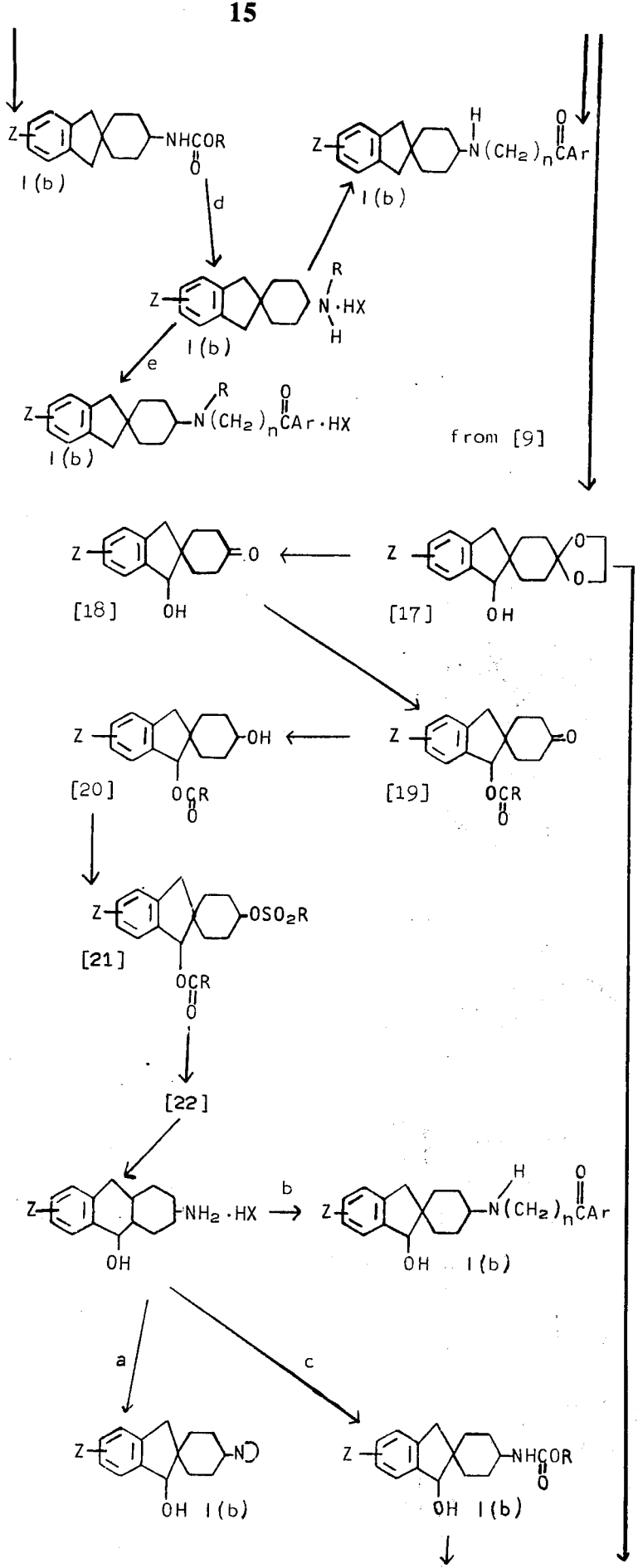

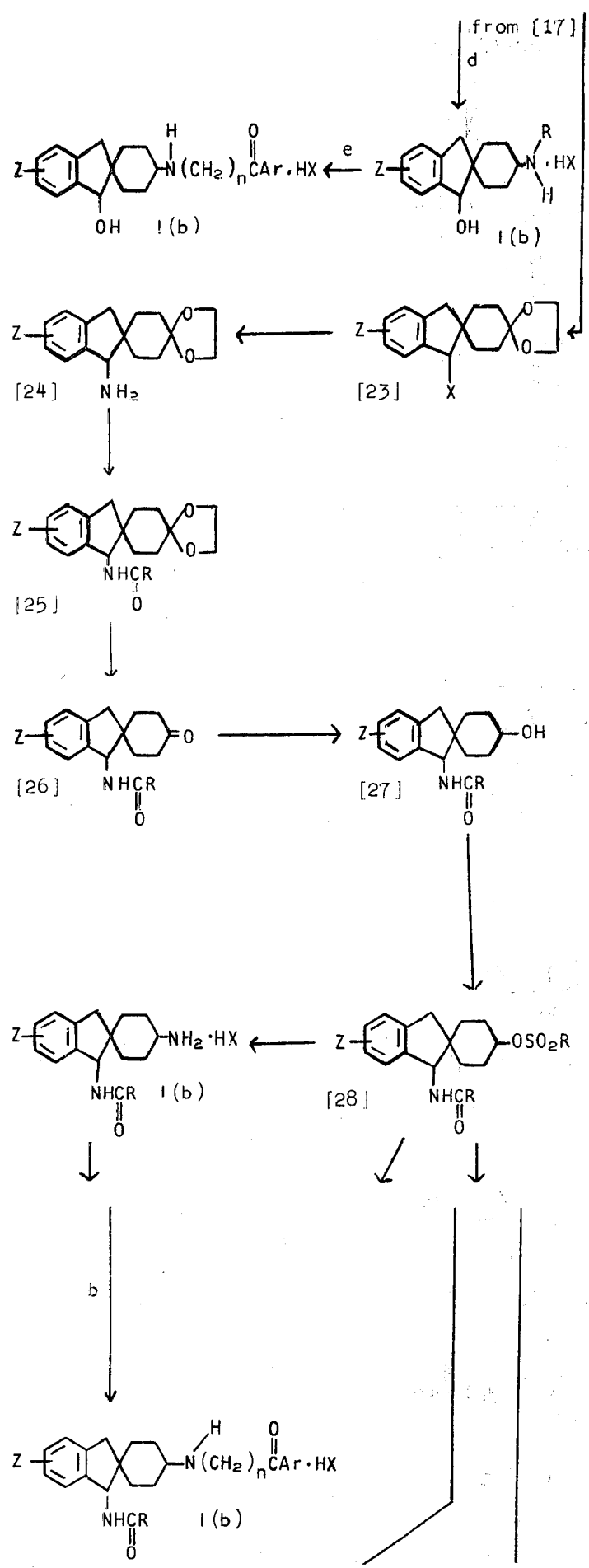

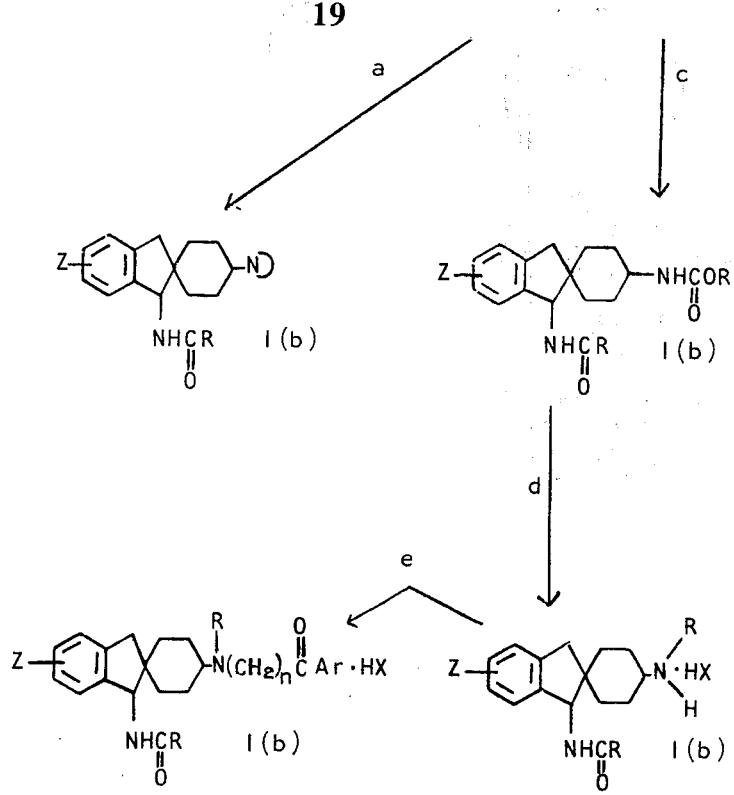
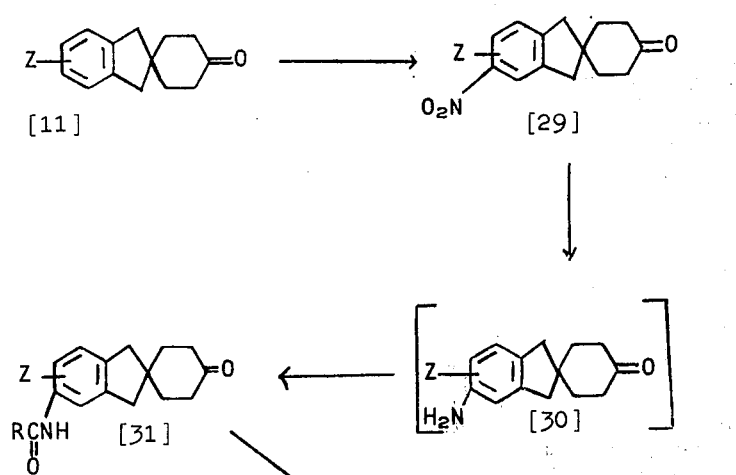
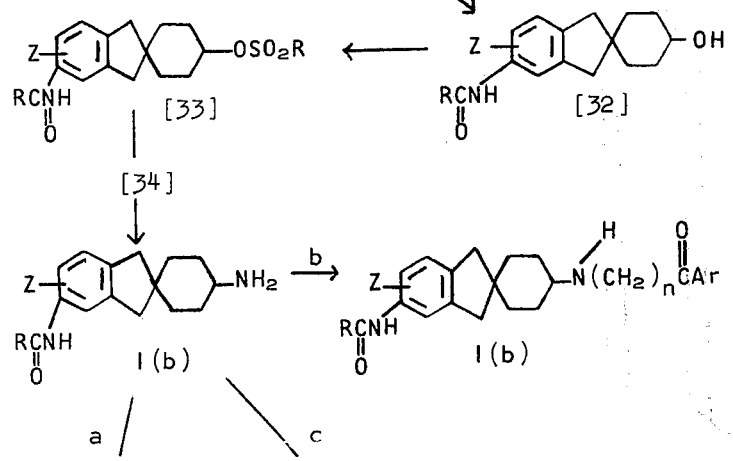

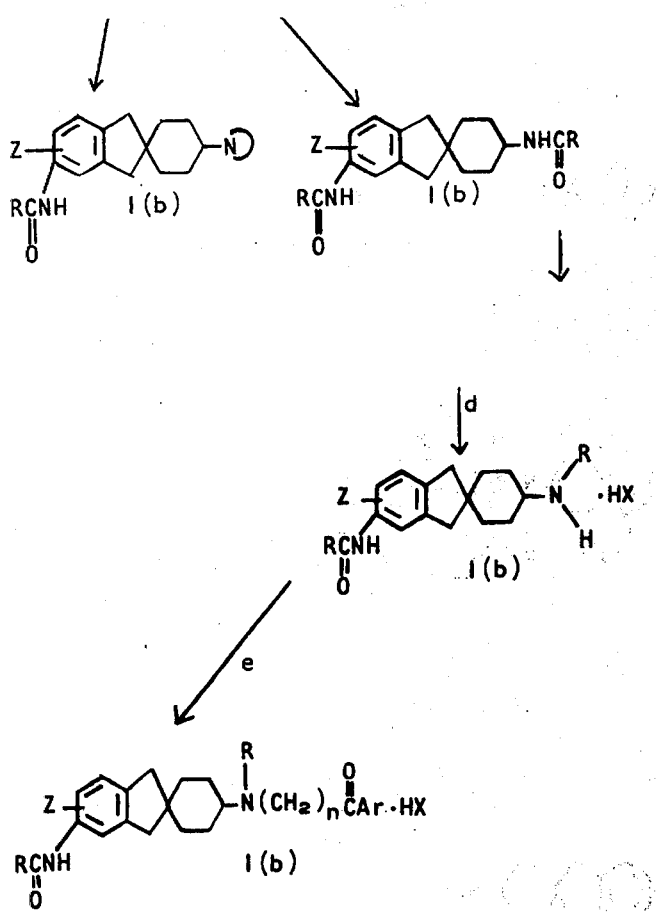
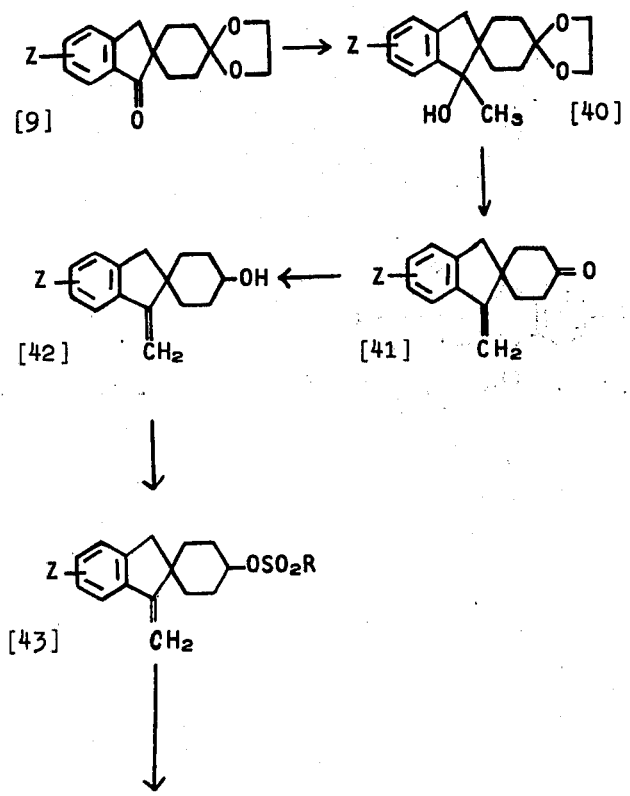

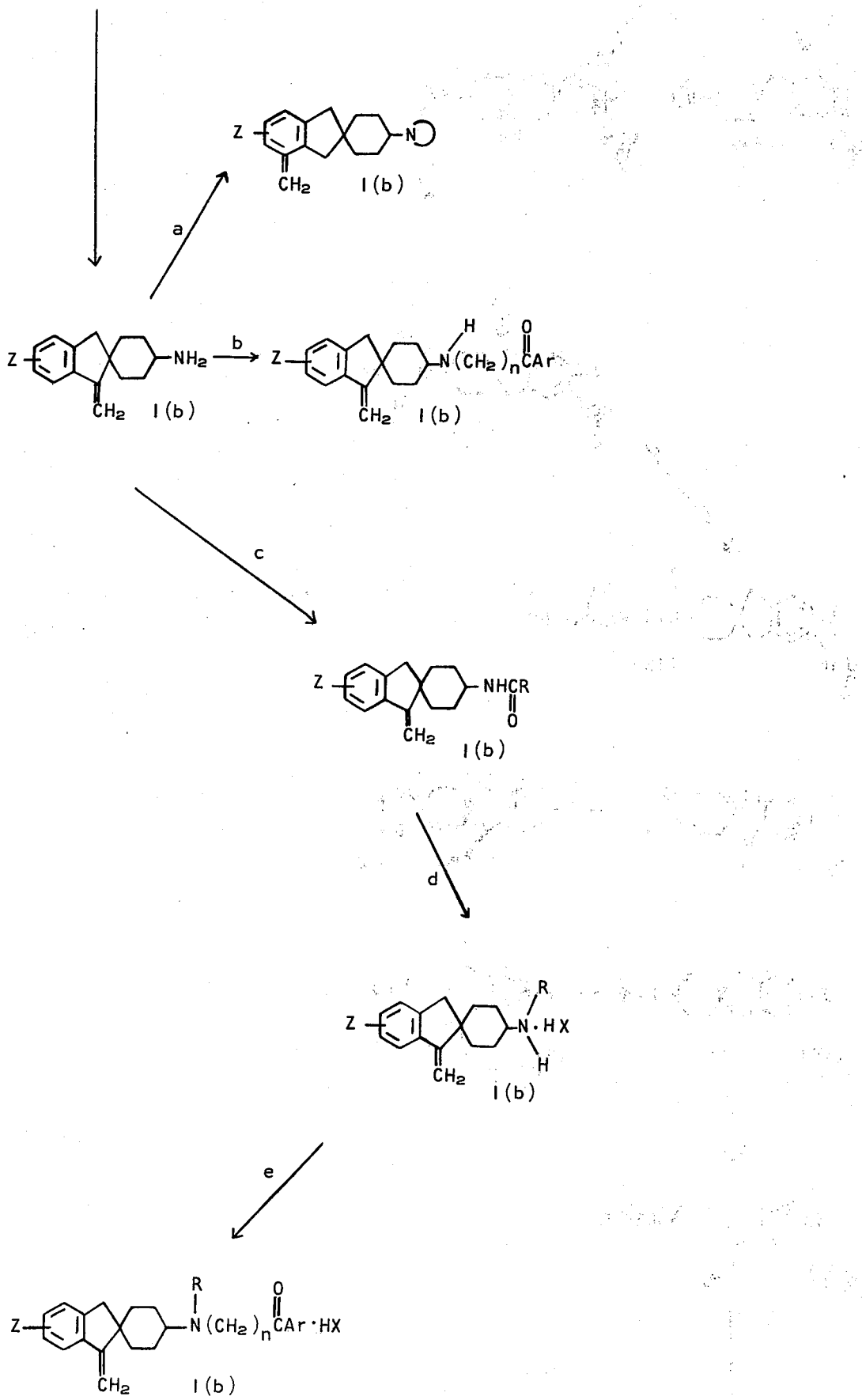

wherein Ar, n, -N◯, R, X and Z have the same meaning as in Process A, above.

The compounds embraced by formula I(b) of the flowsheet designated Process B, above, are prepared by the procedures indicated therein, employing the methods and reactions described below.

1. The first step of the process comprises reducing an alkyl p-hydroxy benzoate [1] (prepared as in Ann. 141, 247), e.g., by hydrogenating it in the presence of a catalyst (such as 5 percent rhodium/aluminum) in a solvent (such as absolute ethanol) at room temperature, to yield a corresponding alkyl-4-hydroxycyclohexane carboxylate [2].

2. An alkyl-4-hydroxycyclohexane carboxylate [2] obtained in step (1) is oxidized at the 4-position, e.g., in acetone with Jones reagent as low temperature (at from about 5° to about 20° C.) to give a corresponding 4-carboalkoxy-1-cyclohexanone [3].

3. A 4-carboalkoxy-1-cyclohexanone [3] prepared in step (2) is ketalized at the 4-position, e.g., by heating (at reflux) in benzene with an alkylene glycol (in the presence of a catalyst such as p-toluenesulfonic acid) for from about 4 to about 8 hours, to yield a corresponding 4-carboalkoxy-1-cyclohexanone alkylene ketal [4].

4. A 4-carboalkoxy-1-cyclohexanone alkylene ketal [4] obtained in step (3) on reaction with lithium diisopropyl amide (prepared by adding butyl lithium in a solvent such as pentane to diisopropylamine in a solvent such as tetrahydrofuran at low temperature) followed by addition of a benzyl halide (such as α-bromotoluene, α-chloro-p-xylene, α-bromo-m-xylene, m-methoxybenzyl chloride, and the like), yields a corresponding 4-benzyl (or substituted benzyl)-4-carboalkoxy-1-cyclohexane alkylene ketal [5].

5. A 4-benzyl (or substituted benzyl)-4-carboalkoxy-1-cyclohexane alkylene ketal [5] obtained in step (4) is saponified, e.g., by heating (at reflux for from about 10 to about 24 hours) in a solvent such as ethylene glycol with an alkali metal hydroxide (such as potassium hydroxide), to give a corresponding 4-benzyl (or substituted benzyl)-4-carboxy-1-cyclohexanone alkylene ketal [6].

6. A 4-benzyl (or substituted benzyl)-4-carboxy-1-cyclohexanone alkylene ketal [6] prepared in step (5) is deketalized, e.g., by stirring it with a dilute aqueous acid (e.g., hydrochloric acid) in acetone at moderate (room) temperature for from about 6 to about 60 hours, to give a corresponding 1-benzyl (or substituted benzyl)-4-cyclohexanone-1-carboxylic acid [7].

7. Reacting a 1-benzyl (or substituted benzyl)-4-cyclohexanone-1-carboxylic acid [7] obtained in step (6) with hydrogen fluoride at room temperature (or with phosphorus pentachloride at reflux temperature, followed by treatment with stannic chloride), gives a corresponding unsubstituted or substituted spiro(cyclohexane-1,2'-indan)-1'4-dione [8].

8. An unsubstituted or substituted spiro(cyclohexane-1,2'-indan)-1'4-dione [8] obtained in step (7) is ketalized at the 4-position, e.g., by heating (at reflux) in benzene with an alkylene glycol (in the presence of a catalyst such as p-toluenesulfonic acid) for from about 3 to 7 hours, to yield a corresponding unsubstituted or substituted spiro(cyclohexane-1,2'-indan)-1',4-dione 4-alkylene ketal [9].

9. A spiro(cyclohexane-1,2'-indan)-1'4-dione 4-alkylene ketal [9] prepared in step (8) on being subjected to Wolff-Kischner reduction, namely, by heating it (at reflux) with hydrazine hydrate and an alkali metal hydroxide (such as potassium hydroxide) in a solvent such as ethylene glycol for from about 8 to about 12 hours, gives a corresponding spiro(cyclohexane-1,2'-indan)-4-one alkylene ketal [10].

10. A spiro(cyclohexane-1,2'-indan)-4-one alkylene ketal [10] obtained in step (9) is deketalized, e.g., by stirring it with a dilute aqueous acid (such as hydrochloric acid) in acetone for from about 3 to about 8 hours, to give a corresponding spiro(cyclohexane-1,2'-indan)-4-one [11].

11. A spiro(cyclohexane-1,2'-indan)-4-one [11] obtained in step (10), on heating at reflux for from about 4 to about 8 hours with an acid addition salt of hydroxylamine and an alkali metal hydroxide such as sodium hydroxide, yields a corresponding spiro(cyclohexane-1,2'-indan)-4-one oxime [12].

12. A spiro(cyclohexane-1,2'-indan)-4-one oxime [12] prepared in step (11), on standing in a solvent such as tetrahydrofuran with an anhydride of a hydrocarbon carboxylic acid in the presence of an esterification catalyst (e.g., pyridine) at moderate (room) temperature for from about 4 to about 8 hours, yields a corresponding spiro(cyclohexane-1,2'-indan)-4-one oxime acylate [13].

13. A spiro(cyclohexane-1,2'-indan)-4-one oxime acylate [13] produced in step (12), on reducing its oxime function, e.g., by reacting said compound with diborane in a solvent such as tetrahydrofuran (preferably at low temperature), yields a corresponding spiro(cyclohexane-1,2'-indan)-4-amine [I(b)] in its free base form, which on extracting with ether and treating said extract with an ethereal solution of a suitable (pharmacologically acceptable) acid, gives the corresponding acid addition salt form.

The compounds embraced by the spiro(cyclohexane-1,2'-indan)-4-amines and their acid addition salts [I(b)], immediately above, can be prepared by another method, as follows:

11'. A spiro(cyclohexane-1,2'-indan)-4-one [11] obtained in step (10) has its 4-keto function reduced, e.g., by mixing said compound in ethanol with sodium borohydride at moderate (room) temperature for from about 3 to about 8 hours, to produce a corresponding spiro(cyclohexane-1,2'-indan)-4-ol [14].

12'. Letting stand (preferably at low temperature for from about 3 to about 18 hours) a mixture of a spiro(cyclohexane-1,2'-indan)-4-ol [14] obtained in step (11') in an amine base (e.g., pyridine) and a lower alkyl sulfonyl halide (such as methanesulfonyl chloride), yields a corresponding spiro(cyclohexane-1,2'-indan)-4-ol lower alkyl sulfonate [15].

13'. A spiro(cyclohexane-1,2'-indan)-4-ol lower alkyl sulfonate [15] obtained in step (12') and sodium azide in a solvent such as dimethylformamide, on heating (at from 65° to about 100° C. for from about 4 to about 20 hours), yields a corresponding spiro(cyclohexane-1,2'-indan)-4-ylazide [16]; on reduction of the azido function of a thus produced compound [16], e.g., by reacting said compound with lithium aluminum hydride in a solvent such as tetrahydrofuran at moderate (room) temperature for from about 3 to about 10 hours, yields a corresponding spiro(cyclohexane-1,2'-indan)-4-amine [I(b)] in its free base form, which on extracting with ether and treating said extract with an ethereal solution of a suitable acid, gives the corresponding acid addition salt form.

The free base or acid addition salt forms of the spiro(cyclohexane-1,2'-indan)-4-amines [I(b)] obtained as in step (13) or (13'), above, are employed as starting materials for preparing a variety of derivatives thereof, for example, in accordance with the methods set forth in (a) through (e) that follow.

a. Heating (e.g., under reflux for from about 8 to about 24 hours) a spiro(cyclohexane-1,2'-indan)-4-amine [I(b)] obtained in step (13) or (13') with a dihaloalkane, yields a corresponding (1-single ring nitrogen containing heterocyclo)-spiro(cyclohexane-1,2'-indan)-4-yl [I(b)], which on dissolving in ether and treating with an ethereal solution of an appropriate acid, gives the corresponding acid addition salt thereof. For example, heating a spiro(cyclohexane-1,2'-indan)-4-amine [I(b)] with 1,5-diiodopentane, 1,4-dibromobutane or 1,6-diiodohexane, yields, respectively, an acid addition salt of a corresponding 1-[spiro(cyclohexane-1,2'-indane)-4-yl]piperidine [I(b)], a 1-[spiro(cyclohexane-1,2'-indane)-4-yl]pyrrolidine [I(b)] or a 1-spiro(cyclohexane-1,2'-indan)-4-yl]hexamethyleneimine [I(b)], which can be converted to their acid addition salts in the manner described in the immediately preceding sentence.

b. The production of a compound selected from the group consisting of the free bases and acid addition salts of a 4-[[spiro[cyclohexane-1,2'-indan]-4-yl]amino]alkanophenone of the formula

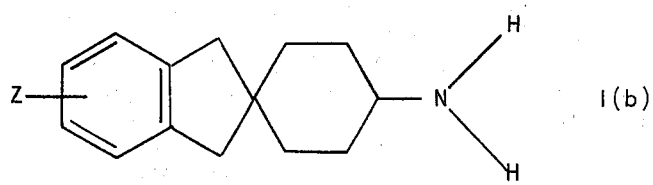

wherein Ar, n and Z have the same meaning as above, comprises reacting (in the presence of an alkali metal iodide and an alkali metal carbonate) a corresponding compound obtained in step (13) or (13') selected from the group consisting of the free bases or acid addition salts of a compound of the formula

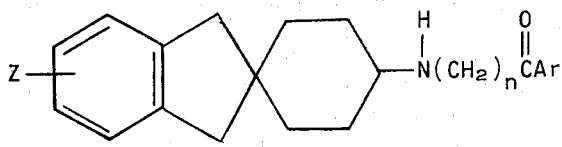

wherein Z has the same meaning as above, with a corresponding compound of the formula

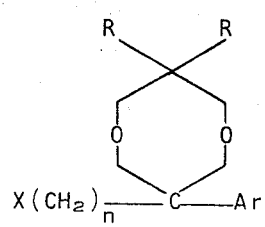

wherein Ar, R and n have the same meaning as above and X is selected from the group consisting of chlorine and bromine, followed by hydrolyzing (i.e., deketalizing) a thus produced compound, e.g., with aqueous acid in an alkanol.

c. Reacting a spiro(cyclohexane-1,2'-indan)-4-amine [I(b)] obtained in step (13) or (13'), haloformate (e.g., ethyl chloroformate, methyl bromoformate or propyl chloroformate) yields a corresponding lower alkyl spiro(cyclohexane-1,2'-indane)-4-carbamate having the formula

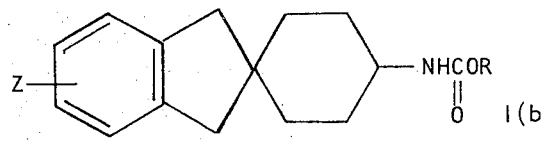

wherein R and Z have the same meaning as above.

d. A lower alkyl spiro(cyclohexane-1,2'-indane)4-carbamate [I(b)], prepared as in (c) immediately above, is reduced, e.g., by heating it (under reflux) in a solvent such as tetrahydrofuran (for from about 8 to about 24 hours) with lithium aluminum hydride, to yield a corresponding spiro(cyclohexane-1,2'-indane)-4-yl-N-methylamine [I(b)], which on dissolving in ether and treating with an ethereal solution of an appropriate acid gives a corresponding acid addition salt thereof.

e. Following the procedure of (b), above, but substituting the free base or acid addition salt of a spiro(cyclohexane-1,2'-indane)-4-yl-N-methylamine [I(b)] obtained as in (d) immediately above as starting material, yields a corresponding [spiro[cyclohexane-1,2'-indan]-2 through 5-yl-N-lower alkylamino]alkanophenone [I(b)], or an acid addition salt thereof.

The unsubstituted and substituted spiro(cyclohexane-1,2'-indan)-1'4-dione alkylene ketals [9] prepared in step (8) of Process B can be employed as starting materials for producing a variety of 1'-hydroxyspiro(cyclohexane-1,2'-indan) compounds [I(b)] by the procedures that follow.

1. A spiro(cyclohexane-1,2'-indan)-1'4-dione alkylene ketal [9] has its 1'-keto function reduced, e.g., by reacting said compound with lithium aluminum hydride in a solvent such as tetrahydrofuran at moderate (room) temperature for from about 3 to about 10 hours, yields a corresponding 1'-hydroxyspiro(cyclohexane-1,2'-indan)-4-one alkylene ketal [17].

2. A 1'-hydroxyspiro(cyclohexane-1,2'-indan)-4-one alkylene ketal [17] produced in step (1) has its ketal protective group removed by hydrolysis, e.g., by allowing said compound to stand for from about 4 to about 20 hours with an acid (such as hydrochloric acid) in a solvent such as acetone) at room temperature, to yield a corresponding 1'-hydroxyspiro(cyclohexane-1,2'-indan)-4-one [18].

3. A 1'-hydroxyspiro(cyclohexane-1,2'-indan)-4-one [18] prepared in step (2), on standing at room temperature for from about 5 to about 10 hours in a solvent such as tetrahydrofuran with an anhydride of a hydrocarbon carboxylic acid in the presence of an esterification catalyst (e.g., pyridine), yields a corresponding 1'-acyloxyspiro(cyclohexane-1,2'-indan)-4-one [19].

4. A 1'-acyloxyspiro(cyclohexane-1,2'-indan)-4-one [19] produced in step (3) has its 4-keto function reduced, e.g., by stirring said compound (in a solvent such as isopropanol) with sodium borohydride at moderate (room) temperature for from about ½ to about 4 hours, to give a corresponding 1'-acyloxyspiro(cyclohexane-1,2'-indan)-4-ol [20].

5. Letting stand (preferably in the cold for from about 4 to about 20 hours) a mixture of a 1'-acyloxyspiro(cyclohexane-1,2'-indan)-4-ol [20] obtained in step (4) in an amine base (e.g., pyridine and a lower alkyl sulfonyl halide (e.g., methanesulfonyl chloride), yield a corresponding 1'-acyloxyspiro(cyclohexane-1,2'-indan)-4-ol lower alkylsulfonate [21].

6. A 1'-acyloxyspiro(cyclohexane-1,2'-indan)-4-ol lower alkylsulfonate [21] obtained in step (5) and sodium azide in a solvent such as dimethylformamide, on heating (at from about 65° to about 100° C. for from about 4 to about 20 hours), yields a corresponding 1'-acyloxyspiro(cyclohexane-1,2'-indan)-4-ylazide [22], which on reduction, e.g., by reaction with lithium aluminum hydride in a solvent such as tetrahydrofuran at room temperature for from 8 to about 16 hours, yields a corresponding 1'-hydroxyspiro(cyclohexane-1,2'-indan)-4-amine [I(b)] in its free base form, which on extracting with ether and treating the extract with an ethereal solution of a suitable acid, (e.g., hydrochloric), gives the corresponding acid addition salt form.

The free base or acid addition salt forms of the 1'-hydroxyspiro(cyclohexane-1,2'-indan)-4-amines [I(b)] obtained in step (6) immediately above, are employed as starting materials for preparing a variety of derivatives thereof, for example, in accordance with the methods set forth in (a) through (e) that follow.

a. Heating (e.g., under reflux for from about 8 to about 24 hours) a 1'-hydroxyspiro(cyclohexane-1,2'-indan)-4-amine [I(b)] obtained in step (6) with a dihaloalkane, yields a corresponding (1-single ring nitrogen containing heterocyclo)-1'-hydroxyspiro(cyclohexane-1,2'-indan)-4-yl [I(b)], which on dissolving in ether and treating with an appropriate acid, gives the corresponding acid addition salt thereof. For example, heating a 1'-hydroxyspiro(cyclohexane-1,2'-indan)-4-amine [I(b)] with 1,5-diiodopentane, 1,4-dibromobutane or 1,6-diiodohexane, yields, respectively, a corresponding 1'-hydroxy-1-[spiro(cyclohexane-1,2'-indan)-4-yl]piperidine [I(b)], a 1'-hydroxy-1-[spiro(cyclohexane-1,2'-indane)-4-yl]pyrrolidine [I(b)] or a 1'-hydroxy-1-[spiro(cyclohexane-1,2'-indan)-4-yl]hexamethyleneimine [I(b)], which are converted to their acid addition salts in the manner described in the immediately preceding sentence.

b. The production of a compound selected from the group consisting of the free bases and acid addition salts of a 4-[(1'-hydrospiro[cyclohexane-1,2'-indan]-4-yl)amino]alkanophenone [I(b)] comprises: reacting (in the presence of an alkali metal iodide and an alkali metal carbonate) a corresponding 1'-hydroxyspiro(cyclohexane-1,2'-indan)-4-amine [I(b)] obtained in step (6) with a corresponding 2,2-dialkyl-1,3-propanediol ketal of a ω-haloalkanophenyl ketone, followed by hydrolyzing a thus produced compound.

c. Reacting a 1'-hydroxy-4-[[spiro[cyclohexane-1,2'-4-amine [I(b)] obtained in step (6) in pyridine in the cold with a lower alkyl haloformate, yields a corresponding lower alkyl-1'-hydroxyspiro(cyclohexane-1,2'-indan)-4-carbamate [I(b)].

d. A lower alkyl-1'-hydroxy-spiro(cyclohexane-1,2'-indane)-4-carbamate [I(b)], prepared as in (c) immediately above, is reduced by heating with lithium aluminum hydride, to yield a corresponding 1'-hydroxyspiro(cyclohexane-1,2'-indan)-4-yl-N-lower alkylamine [I(b)], which on dissolving in ether and treating with an ethereal solution of an appropriate acid give a corresponding acid addition salt thereof.

e. Following the procedure of (b), above, but substituting the free base or acid addition salt of a 1'-hydroxyspiro(cyclohexane-1,2'-indan)-4-yl-N-lower alkylamine [I(b)] obtained as in (d) immediately above as starting material, yields a corresponding 4-[1'-hydroxyspiro[cyclohexane-1,2'-indan]-2 through 5-yl-N-lower alkylamino]-alkanophenone [I(b)], or an acid addition salt thereof.

The unsubstituted and substituted 1'-hydroxy-spiro(cyclohexane-1,2'-indan)-4-one alkylene ketals [17] prepared in step (1) of the process set forth immediately above, can be used as starting materials for producing a variety 1'-acetamido-spiro(cyclohexane-1,2'-indan) compounds by the procedures that follow.

1. A 1'-hydroxy-spiro(cyclohexane-1,2'-indan)-4-one alkylene ketal [17] in a solvent such as tetrahydrofuran is treated in the cold with butyl lithium in a solvent such as pentane and a lower alkyl sulfonyl halide (such as methanesulfonyl chloride) in a solvent (e.g., tetrahydrofuran), to give a corresponding 1'-halospiro(cyclohexan-1,2'-indan)-4-one alkylene ketal [23].

2. A 1'-halospiro(cyclohexan-1,2'-indan)-4-one alkylene ketal [23] produced in step (1) is heated with sodium azide in a solvent such as dimethylformamide at from about 80° to about 100° C. for from about 15 to about 24 hours and the resulting azido intermediate recovered by conventional procedures and then reduced (e.g., with lithium aluminum hydride in a solvent such as tetrahydrofuran), to give a corresponding 1'-aminospiro(cyclohexane-1,2'-indan)-4-one ethylene ketal [24].

3. A 1'-aminospiro(cyclohexane-1,2'-indan)-4-one alkylene ketal [24] prepared in step (2) is acylated, e.g., by treating it with an anhydride of a hydrocarbon carboxylic acid (such as acetic anhydride) in the presence of a catalyst (such as pyridine), to give a corresponding 1'-acylamidospiro(cyclohexane-1,2'-indan)-4-one alkylene ketal [25].

4. A 1'-acylamidospiro(cyclohexane-1,2'-indan)-4-one alkylene ketal [25] produced in step (3), is hydrolyzed, e.g., by standing at room temperature for from about 5 to about 20 hours with an acid such as hydrochloric acid in a solvent such as acetone, to give a corresponding 1'-acylamidospiro(cyclohexane-1,2'- indan)-4-one [26].

5. A 1'-acylamidospiro(cyclohexane-1,2'-indan)-4-one [26] obtained in step (4) has its 4-keto function reduced, e.g., by reacting said compound with sodium borohydride in a solvent such as isopropanol at moderate (room) temperature for from about 3 to about 10 hours, to give a mixture of 1'-acylamidospiro(cyclohexane-1,2'-indan)-4-ols [27], which are separated into their two isomers by conventional procedures, e.g., chromatography or fractional crystallization.

6. Letting either of the isomers of the 1'-acylamidospiro(cyclohexane-1,2'-indan)-4-ols [27] obtained in step (5) stand for from about 3 to about 10 hours in an amine base (e.g., piperidine) with a lower alkyl sulfonyl halide (e.g., methanesulfonyl chloride, yields a corresponding 1'-acylamidospiro(cyclohexane-1,2'-indan)-4-ol lower alkyl sulfonate [28].

7. A 1'-acylamidospiro(cyclohexane-1,2'-indan)-4-ol lower alkylsulfonate [28] obtained in step (6) and sodium azide in a solvent such as dimethylformamide, on heating (at from about 65° to about 100° C. for from about 4 to about 20 hours), yields a corresponding 1'-acylamidospiro(cyclohexane-1,2'-indan)-4-ylazide, which on reduction, e.g., by reaction with lithium aluminum hydride in a solvent such as tetrahydrofuran at room temperature for from about 8 to about 16 hours, yields a corresponding 1'-acylamidospiro(cyclohexane-1,2'-indan)-4-amine [I(b)] in its free base form, which on extracting with ether and treating said extract with an ethereal solution of a suitable acid (e.g., hydrochloric) gives the corresponding acid addition salt form.

The free base or acid addition salt forms of the 1'-acylamidospiro(cyclohexane-1,2'-indan)-4-amines [I(b)] obtained in step (7) immediately above, are employed as starting materials for preparing a variety of derivatives thereof, in the same manner as described above using the corresponding 1'-hydroxyspiro(cyclohexane-1,2'-indan)-4-amines [I(b)] as starting compounds set forth in (a) through (e) following step (6) of the synthesis of said 1'-hydroxyspiro compounds [I(b)]. By utilizing the aforesaid procedures, compounds such as the following are obtained:

a. 1'-acylamido-1-[spiro(cyclohexane-1,2'-indan)-4-yl]piperidines [I(b)], 1'-acylamido-1-[spiro(cyclohexane)-1,2'-indan)-4-yl]pyrrolidines [I(b)] and 1'-acylamido-1-[spiro(cyclohexane-1,2'-indan)-4-yl]hexamethyleneimines [I(b)];

b. 4-[(1'-acylamidospiro[cyclohexane-1,2'-indan]-4-yl)aminoalkanophenones [I(b)] and acid addition salts thereof;

c. lower alkyl-1'-acylamidospiro(cyclohexane-1,2'-indane)-4-carbamates [I(b)];

d. 1'-acylamidospiro(cyclohexane-1,2'-indan)-4-yl-N-lower alkylamines [I(b)]; and e. 4-[1'-acylamidospiro(cyclohexane-1,2'-indan)-4-yl-N-lower alkylamino]alkanophenones [I(b)], and acid addition salts thereof.

The free base or acid addition salt of a 5'-acylamidospiro(cyclohexane-1,2'-indan)-4-amine [I(b)], also named an N-[4-aminospiro[cyclohexane-1,2'-indan]-5'-yl]acylamide [I(b)], is prepared from a spiro(cyclohexane-1,2'-indan)-4-one [11] starting compound, by employing the procedures that follow.

1. A spiro(cyclohexane-1,2'-indan)-4-one [11] [prepared as above in step (10) of the first process for producing the compounds of Process B] in the cold (at about 0° C.) in trifluoroacetic acid, has nitric acid added thereto and the low temperature maintained for from about 1 to about 4 hours, to yield a corresponding 5'-nitrospiro(cyclohexane-1,2'-indan)-4-one [29].

2. A 5'-nitrospiro(cyclohexane-1,2'-indan)-4-one [29] produced in step (1) is catalytically reduced (e.g., with hydrogen in the presence of palladium on carbon, in a solvent such as ethyl acetate), to give a corresponding 5'-aminospiro(cyclohexane-1,2'-indan)-4-one [30].

3. A 5'-aminospiro(cyclohexane-1,2'-indan)-4-one [30] prepared in step (2) is treated in the cold (at about 0° C.) with an amine base such as pyridine and the anhydride of a hydrocarbon carboxylic acid (e.g., acetic anhydride) for from about 3 to about 8 hours, to give a corresponding 5'-acylamidospiro(cyclohexane-1,2'-indan)-4-one [31].

4. A 5'-acylamidospiro(cyclohexane-1,2'-indan)-4-one [31] prepared in step (3) has its 4-keto function reduced, e.g., by reacting said compound with sodium borohydride in a solvent such as isopropanol at moderate (room) temperature for from about 3 to about 10 hours, to give a corresponding 5'-acylamidospiro(cyclohexane-1,2'-indan)-4-ol [32].

Using a thus produced 5'-acylamidospiro(cyclohexane-1,2'-indan)-4-ol [32] as starting material and employing the procedures described in steps (6) and (7) and (a) through (e), above, for preparing the corresponding 1'acylamido compounds, yields 5'-acylamido counterparts such as 6. 5'-acylamidospiro(cyclohexane-1,2'-indan)-4-ol lower alkyl sulfonates [33];

7. 5'-acylamidospiro(cyclohexane-1,2'-indan)-4-ylazides [34] and 5'-acylamidospiro(cyclohexane-1,2'-indan)-4-amines [I(b)] (as free base or acid addition salt);

a. 5'-acylamido-1-[spiro(cyclohexane-1,2'-indan)-4-yl]piperidines [I(b)], 5'acylamido-1-[spiro(cyclohexane-1,2'-indan)-4-yl]pyrrolidines [I(b)] and 5'-acylamido-1-[spiro(cyclohexane-1,2'-indan)-4-yl]hexamethyleneimines [I(b)];

b. 4-[[5'-acylamidospiro[cyclohexane-1,2'-indan]-4-yl]amino]alkanophenones [I(b)] and acid addition salts thereof;

c. lower alkyl-5'-acylamidospiro(cyclohexane-1,2'-indan)-4-carbamates [I(b)];

d. 5'-acylamidospiro(cyclohexane-1,2'-indan)-4-yl-N-lower alkylamines [I(b)]; and e. 4-[5'-acylamidospiro[cyclohexane-1,2'-indan)-4-yl-N-lower alkylamino]alkanophenones [I(b)], and acid addition salts thereof.

The unsubstituted or substituted spiro(cyclohexane-1,2'-indan)-1'4-dione alkylene ketals [9] [prepared as in step (8) of the first process for producing the compounds of Process B] can be employed as starting materials for preparing a variety of 1'-exomethylenespiro(cyclohexane-1,2'-indan) compounds by the procedures that follow.

A spiro(cyclohexane-1,2'-indan)-1'4-dione-4-alkylene ketal (9) in a solvent such as tetrahydrofuran, on addition to a methyl magnesium halide (such as methyl magnesium bromide) in a solvent such as ether, after standing at moderate (room) temperature for from about 6 to about 24 hours, gives a corresponding 1'-hydroxy-1'-methyl-spiro(cyclohexane-1,2'-indan)-4-one alkylene ketal [40].

2. A 1'-hydroxy-1'-methylspiro(cyclohexane-1,2'- indan)-4-one alkylene ketal [40] produced in step (1), on stirring with an acid (such as hydrochloric)

in a solvent (such as acetone) at room temperature for from about 4 to about 20 hours, yields a corresponding 1′-exo-methylenespiro(cyclohexane-1,2′-indan)-4-one [41].

3. A 1′-exo-methylenespiro(cyclohexane-1,2′-indan)-4-one [41] prepared in step (2) has its 4-keto function reduced, e.g., by stirring said compound (in a solvent such as isopropanol with sodium borohydride at moderate (room) temperature for from about 2 to about 10 hours, to give a corresponding 1′-exo-methylenespiro(cyclohexane-1,2′-indan)-4-ol [42].

4. Letting stand (preferably in the cold for from about 4 to about 20 hours) a mixture of a 1′-exo-methylenespiro(cyclohexane-1,2′-indan)-4-ol [42] obtained in step (3) in an amine base (such as pyridine) and a lower alkyl sulfonyl halide (such as methanesulfonyl chloride), yeilds a corresponding 1′-exo-methylenespiro(cyclohexane-1,2′-indan)-4-ol lower alkyl sulfonate [43].

5. A 1′-exo-methylenespiro(cyclohexane-1,2′-indan)-4-ol lower alkylsulfonate [43] obtained in step (4) and sodium azide in a solvent such as dimethylformamide, on heating at from about 65° to about 100°C. for from about 4 to about 20 hours, gives a corresponding 1′-exo-methylenespiro(cyclohexane-1,2′-indan)-4-ylazide [44], which on reduction, e.g., with lithium aluminum hydride in a solvent such as tetrahydrofuran at room temperature for from about 4 to about 16 hours, yields a corresponding 1′-exo-methylenespiro(cyclohexane-1,2′-indan)-4-amine [I(b)] in its free base form, which on extracting with ether and treating said extract with an ethereal solution of a suitable acid (e.g., hydrochloric), gives the corresponding acid addition salt form.

The free base or acid addition salt forms of 1′-exo methylenespiro(cyclohexane-1,2′-indan)-4-amines [I(b)] obtained in step (5) immediately above, are employed as starting materials for preparing a variety of derivatives thereof, in the same manner as described above using the corresponding 1′-hydroxyspiro(cyclohexane-1,2′-indan)-4-amines [I(b)] as starting compounds set forth in (a) through (e) following step (6) of the synthesis of said 1′-hydroxyspiro compounds [I(b)]. By following the aforesaid procedures, there are obtained 1′-exo-methylene counterparts such as a. 1′-exo-methylenespiro(cyclohexane-1,2′-indan)-piperidines [I(b)] 1′-exo-methylenespiro(-cyclohexane-1,2′-indan)pyrrolidines [I(b)] and 1′-exo-methylenespiro(cyclohexane-1,2′-indan)-hexamethyleneimines [I(b)];

b. alkanophenones of 1′-exo-methylenespiro(cyclohexane-1,2′-indan-4-amine [I(b)], also names 4-[[1′-methylenespiro(cyclohexan-1,2′-indan)-4-yl]amino]alkanophenones [I(b)], and acid additon salts thereof;

c. lower alkyl 1′-exo-methylenespiro(cyclohexane-1,2′-indane)-4-carbamates [I(b)];

d. 1′-exo-methylenespiro(cyclohexane-1,2′-indan)-4-yl-N-lower alkylamines [I(b)]; and e. 4-[1′-exo-methylenespiro(cyclohexane-1,2′-indan)-4-yl-N-lower alkylamino]alkanophenones [I(b)] and acid addition salts thereof.

Process C

The following sequence of formulae illustratively represents procedures for the preparation of compounds of Formula I(c).

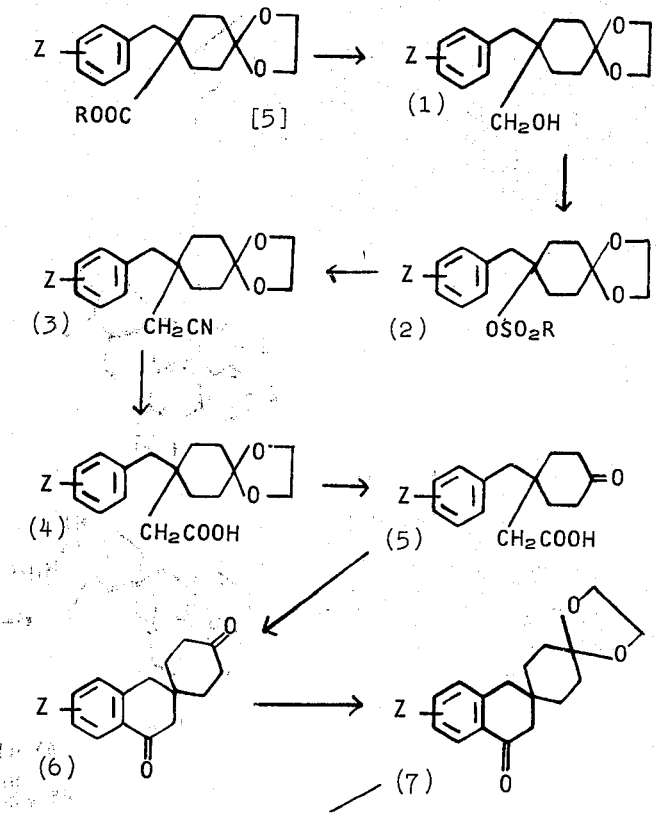

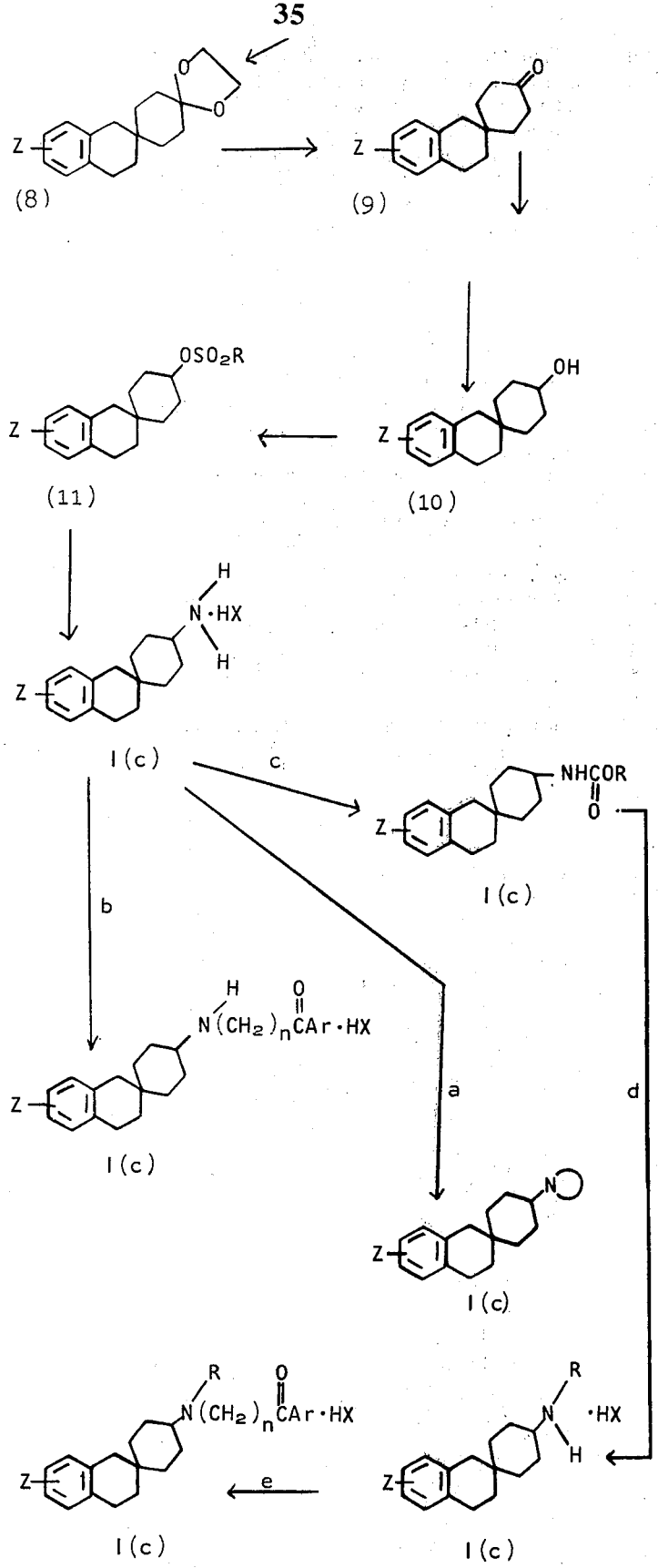
wherein Ar, $n$, —N◯, R, X and Z have the same meaning as in Process A, above.
The compounds embraced by Formula I(c) of the flow-sheet designated Process C, above, are prepared by the procedures indicated therein, employing the methods and reactions described below.

1. The first step of the process comprises reducing a 4-benzyl (or substituted benzyl)-4-carboalkoxy-1-cyclohexanone alkylene ketal [5] [prepared as above in step (4) of the first process for producing the compounds of Process B], for example, by reacting it in a solvent such as tetrahydrofuran with lithium aluminum hydride and heating the reaction mixture (at reflux) for from about 3 to about 8 hours, to give a corresponding 4-benzyl (or substituted benzyl)-4-hydroxymethylcyclohexan-1-one alkylene ketal (1).

2. A 4-benzyl (or substituted benzyl)-4-hydroxymethyl-cyclohexan-1-one alkylene ketal (1) obtained in step (1) in an amine base (such as pyridine) on standing in the cold with a lower alkyl sulfonyl halide (such as methanesulfonyl chloride), yields a corresponding 4-benzyl (or substituted benzyl)-4-hydroxymethylcyclohexan-1-one, alkylene ketal, lower alkyl sulfonate (2).

3. A 4-benzyl (or substituted benzyl)-4-hydroxymethylcyclohexan-1-one, alkylene ketal lower alkyl sulfonate (2) prepared in step (2) on heating for from about 10 to about 18 hours at from about 100° to about 165° C. with potassium cyanide in a solvent such as hexamethylphosphoramide, yields a corresponding 4-benzyl-4-cyanomethylcyclohexan-1-one alkylene ketal (3).

4. A thus produced 4-benzyl-4-cyanomethylcyclohexan-1-one alkylene ketal (3) obtained in step (3) on saponification, e.g., by heating it with an alkali metal hydroxide (such as potassium hydroxide) in a solvent such as an alkalene glycol (e.g., ethylene glycol) for from about 8 to about 18 hours, gives a corresponding 4-benzylcyclohexan-4-acetic acid-1-one alkylene ketal (4).

5. A 4-benzylcyclohexane-4-acetic acid-1-one alkylene ketal (4) prepared in step (4) is deketalized, e.g., by stirring it with a dilute aqueous acid (e.g., hydrochloric) in acetone at moderate (room) temperature for from about 36 to about 72 hours, to give a corresponding 4-benzylcyclohexan-4-acetic acid-1-one (5).

6. A 4-benzylcyclohexane-4-acetic acid-1-one (5) prepared in step (5) is cyclized, e.g., by allowing it to stand at moderate (room) temperature for from about 15 to about 80 hours with liquid hydrogen fluoride, to yield a corresponding 3',4'-dihydroxpiro[cyclohexane-1,2' (1'H)-naphthalene]-4',4-dione (6).

7. A 3',4'-dihydrospiro[cyclohexane-1,2' (1'H)-naphthalene]-4', 4-dione (6) obtained in step (6) is monoketalized at the non-conjugated least hindered carbonyl function, e.g., by heating (at reflux) in a solvent such as benzene with an alkylene glycol (in the presence of a catalyst such as p-toluenesulfonic acid), to yield a corresponding 3', 4', -dihydrospiro[cyclohexane-1,2'(1'H)-naphthalene]-4',4-dione, 4-(ethylene ketal) (7).

8. A 3',4'-dihydrospiro[cyclohexane-1,2'(1'H)-naphthalene]-4',4-dione, 4-(ethylene ketal) (7) prepared in step (7) is reduced at the 1'-position, e.g., by heating (at reflux) for from about ½ to about 3 hours with hydrazine hydrate and a base (e.g., potassium hydroxide) in a solvent such as an alkylene glycol (e.g., ethylene glycol), to give a corresponding 3',4'-dihydrospiro[cyclohexane-1,2'(1'H)-naphthalen]-4-one, ethylene ketal (8).

9. In this step, a 3',4'4-dihydrospiro[cyclohexane-1,2'-(1'H)-naphthalen]-4-one, ethylene ketal (8) obtained in step (8) has its ketal protective group removed by hydrolysis, e.g., by heating it (at reflux) for from about 8 to about 20 hours with an acid (such as hydrochloric) in a solvent (such as acetone), to yield a corresponding 3',4'-dihydrospiro[cyclohexane-1,2'(1'H)-naphththalen]-4-one (9).

10 A 3',4'-dihydrospiro[cyclohexane-1,2'(1'H)-naphthalen]-4-one produced, e.g., by mixing said compound in a solvent such as isopropanol with sodium borohydride at moderate (room) temperature, to give a corresponding 3',4'-dihydrospiro[cyclohexane-1,2'(1'H)-naphthalen]-4-ol (10).

11. A 3',4'-dihydrospiro[cyclohexane-1,2'(1'H)-naphthalen]-4-ol obtained in step (10) on standing in the cold (at about 0° C.) for from about 3 to about 6 hours in an amine base (e.g., pyridine) with a lower alkyl sulfonyl halide (e.g., methanesulfonyl chloride), gives a corresponding 3',4'-dihydrospiro[cyclohexane-1,2'(1'H)-naphthalen]-4-ol lower alkyl sulfonate (11).

12. A 3',4'-dihydrospiro[cyclohexane-1,2'(1'-'H)-naphthalen]-4-ol lower alkyl sulfonate prepared in step (11) and sodium azide in a solvent such as dimethylformamide, on heating (at from about 65° to about 100° C. for from about 4 to about 20 hours); yields a corresponding 3',4'-dihydrospiro[cyclohexane-1,2'(1'H)-naphthalen]-4-ylazide, which on reaction with lithium aluminum hydride in a solvent such as tetrahydrofuran at moderate (room) temperature for from about 3 to about 10 hours, yields a corresponding 3',4'-dihydrospiro(cyclohexane-1,2'(1'-'H)-naphthalen)-4-ylamine [I(c)] in its free base form. On treating an ether extract of a thus produced compound with an ethereal solution of a suitable (pharmacologically acceptable) acid, its acid addition salt form is obtained.

The free base or acid addition salt forms of the 3',4'-dihydrospirol[cyclohexane-1,2'(1'H)-naphthalen]-4-ylamines [I(c)] obtained as in step (12), above, are employed as starting materials for producing a variety of derivatives thereof, for example, in accordance with the methods described in (a) through (e) that follow.

a. Heating (e.g., under reflux for from about 8 to about 24 hours) a 3',4'-dihydrospiro[cyclohexane-1,2'(1'H)-naphthalen]-4-ylamine [I(c)] obtained in step (12) with a dihaloalkane, gives a corresponding (1-single ring nitrogen containing heterocyclo)-3',4'-dihydrospiro[cyclohexane-1,2'(1'H)-naphthalen]-4-yl [I(c)], which on dissolving in ether and treating with an ethereal solution of an appropriate acid, yields the corresponding acid addition salt. For example, heating a 3',4'-dihydrospiro[cyclohexane-1,2'(1'H)-naphthalen]-4-ylamine [I(c)] with 1,5-diiodopentane, 1,4-dibromobutane or 1,6-diiododhexane, yields, respectively, a corresponding 1-[3',4'-dihydrospiro[cyclohexane-1,2'(1'H)-naphthalen]-4-yl]piperidine [I(c)], a 1-[3',4'-dihydrospiro[cyclohexane-1,2'(1'H)-naphthalen]-4-yl]pyrrolidine [I(c)] or a 1-[3',4'-dihydrospiro(cyclohexane-1,2'(1'H)-naphthalen)-4-yl[hexamethyleneimine [I(c)], which can be converted to their acid addition salts in the manner described in the immediately preceding sentence.

b. The production of a compound selected from the group consisting of the free bases and acid addition salts of a 4-[(3',4'-dihydrospiro[cyclohexane-1,2'(-1'H)-naphthalen]-4-yl)amino]alkanophenone of the formula

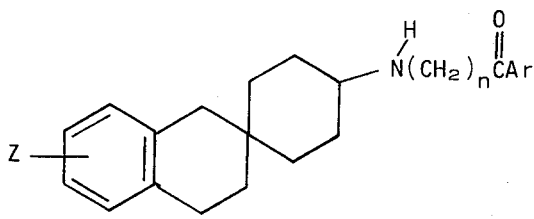

I(c)

wherein Ar, n and Z have the same meaning as above, comprises reacting (in the presence of an alkali metal iodide and an alkali metal carbonate) a corresponding compound obtained as in step (12) selected from the group consisting of the free bases and acid addition salts of a compound of the formula

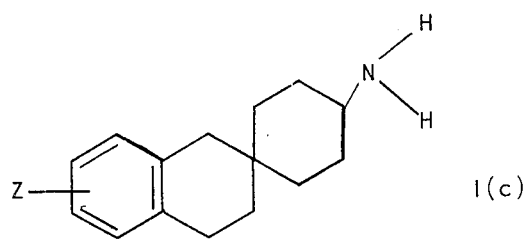

I(c)

wherein Z has the same meaning as above, with the corresponding compound of the formula

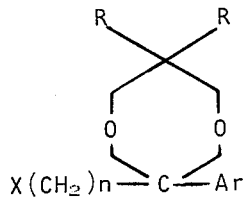

wherein Ar, R and n have the same meaning as above and X is selected from the group consisting of chlorine and bromine, followed by hydrolyzing (i.e., deketalizing) a thus produced compound, e.g., with aqueous acid in an alkanol.

c. Reacting a 3',4'-dihydrospiro[cyclohexane-1,2'(- 1'H)-naphthalen]-4-ylamine [I(c)] obtained as in step (12), in pyridine in the cold with a lower alkyl haloformate (e.g., ethyl chloroformate, methyl bromoformate, propyl chloroformate or isopropyl bromoformate), yields a corresponding lower alkyl 3',4'-dihydrospiro[- cyclohexane-1,2'(1'H)-naphthalene]-4-carbamate of the formula

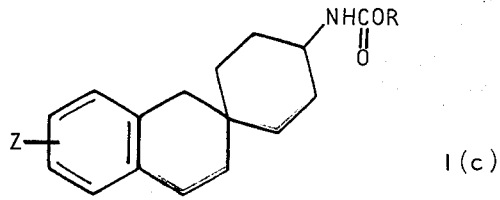

I(c)

wherein R and Z have the same meaning as above.

d. A lower alkyl 3',4'-dihydrospiro[cyclohexane- 1,2'(1'H)-naphthalene]-4-carbamate [I(c)], prepared as in (c) immediately above, is reduced, e.g., by heating it in a solvent such as tetrahydrofuran (under reflux for from about 6 to about 24 hours) with lithium aluminum hydride, to yield a corresponding 3',4'-dihydrospiro[- cyclohexane-1,2'(1'H)-naphthalen]-4-yl-N-methyla- mine [I(c)], which on dissolving in ether and treating with an ethereal solution of an appropriate acid gives a corresponding acid addition salt thereof.

e. Following the procedure of (b), above, but substituting as starting material the free base or acid addition salt of a 3',4'-dihydrospiro[cyclohexane-1,2'(1'H)- naphthalen]-4-yl-N-methylamino [I(c)], obtained as in (d) immediately above, yields a corresponding 4-[(3',- 4'-dihydrospiro[cyclohexane-1,2'(1'H)-naphthalen]-2 through 5-yl-N-methylamino]alkanophenone [I(c)], or an acid addition salt thereof.

All of the compounds included within Formula I (a, b and c) of the flow-sheets, above, can be isolated from their respective reaction mixtures by conventional means, for example, when a water-miscible solvent is used, by pouring the reaction mixture into water rand separating the resulting precipitate by filtration or by extraction with water-immiscible solvents. Additional purification of the products can be accomplished by conventional means, for example, by elution chromatography from an adsorbent column with a suitable solvent such as acetone, ethyl acetate, ether, methylene chloride and Skellysolve B (hexanes), mixtures and combinations of these solvents; also by gradient elution chromatography from an adsorbent column with a suitable mixture of solvents, such as, methylene chloride-Skellysolve B, acetone-Skellysolve B, and the like.

The free bases and acid addition salts of the novel compounds of Formula I are useful as central nervous system (CNS) depressants when administered to humans and animals. They possess tranquilizing activity and are consequently useful in humans for controlling anxiety and schizophrenia; in animals the aforesaid compounds are useful for their calming effects and can be given to reduce aggressive behavior. These compounds have been shown to possess CNS depressing activity (especially tranquilizing activity) via the loss of righting reflex, traction, chimney, dish and pedestal tests carried out in the manner described by Boissier et al. in Medicina Experimentalis 4, 145 (1961).

Tranquilizing effects of compounds of this invention are shown by the following tests in mice:

Chimney test: [Med. Exp. 4, 145 (1961)]: The test determines the ability of mice to back up and out of a verticle glass cylinder within 30 seconds. At the effective dosage, 50 percent of the mice failed doing it.

Dish test: Mice in Petri dishes (10 cm. diameter, 5 cm. high, partially embedded in wood shavings), climb out in a very short time, when not treated. Mice remaining in the dish for more than 3 minutes indicates tranquilization. $ED_{50}$ equals the dose of test compound at which 50 percent of the mice remain in the dish.

Pedestal test: The untreated mouse leaves a standard pedestal in less than a minute to climb back to the floor of the standard mouse box. Tranquilized mice will stay on the pedestal for more than 1 minute.

Nicotine antagonism test: Mice in a group of 6 are injected with the test compound. Thirty minutes later the mice including control (untreated) mice are injected with nicotine salicylate (2 mg./kg.). The control mice show overstimulation, i.e., (1) running convulsions followed by (2) tonic extensor fits; followed by (3) death.

The following compounds typical of this invention have (by intraperitoneal injection) $ED_{50}$ as shown in the table below.

| COMPOUND | | $ED_{50}$ (in mg./kg.) | | |
|---|---|---|---|---|
| | Ch | D | P | Ni |
| 4'-fluoro-4-[(3',4'-dihydro-spiro[cyclohexane-1,1'(2'H)-naphthalen]-4-yl)amino]butyrophenone hydrochloride [I(a)] | 25 | 10 | 16 | 5 |
| 4'-fluoro-4-[methyl(spiro-[cyclohexane-1,2'-indan)-4-yl)amino]butyrophenone hydrochloride [I(b)] | 16 | 3.6 | 9 | 4 |
| 4'-fluoro-4-[(3',4'-dihydro-spiro[cyclohexane-1,2'(1'H)-naphthalen]-4-yl)amino]butyrophenone hydrochloride [I(c)] | 9.9 | 9.9 | 12.5 | 7 |

Ch = chimney test
D = dish test
P = pedestal test
Ni = nicotine antagonism (3) test As tranquilizers, the compounds of Formula I (a, b and c) and their pharmacologically acceptable acid addition salts can be prepared and administered to humans, mammals, birds and animals in a wide variety of oral or parenteral dosage forms, singly or in admixture with other coacting compounds, in doses of from about 10 mg. to about 100 mg./kg., depending on the severity of the condition being treated and the recipient's response to the medication.

The free bases and pharmacologically acceptable acid addition salts of the compounds of Formula I (a, b and c) are also useful in lowering blood pressure when administered to humans and animals. This activity makes them useful in the treatment of essential hypertension. These compounds have been shown to possess hypotensive activity when tested in the manner described by Weeks and Jones, in Proc. Soc. Exp. Biol. and Med. 104, 646 (1960). The following compounds typical of this invention have (by oral administration to rats) $MED_{100}$ (minimal effective dose) as shown in the table below.

| COMPOUND | $MED_{100}$ (in mg./kg.) |
|---|---|
| 4'-fluoro-4-[(spiro[cyclohexane-1,2'-indan]-4-yl)amino]butyrophenone hydrochloride [I(b)] | 50 |
| 4'-fluoro-4-[[1'-hydroxyspiro-[cyclohexane-1,2'-indan]-4-yl]-amino]butyrophenone hydrochloride [I(b)] | 50 |

As hypotensives, the compounds of Formula I (a, b and c) and their pharmacologically acceptable acid addition salts can be prepared and administered to humans, mammals, birds and animals in a wide variety of oral or parenteral dosage forms, singly or in admixture with other coacting compounds in doses of from about 10 mg. to about 100 mg./kg., depending on the severity of the condition being treated and the recipient's response to the medication.

The compounds of Formula I (a, b and c) (used as tranquilizers and/or hypotensives) can be administered with a pharmaceutical carrier which can be solid material or a liquid in which the compound is dissolved, dispersed or suspended. The solid compositions can take the form of tablets, powders, capsules, pills or the like, preferably in unit dosage forms for simple administration or precise dosages. The liquid compositions can take the form of solutions, emulsions, suspensions, syrups, or elixirs.

DETAILED DESCRIPTION

The following examples are illustrative of the manner of making and using the invention and set forth the best mode comtemplated by the inventor of carrying out his invention, but are not to be construed as limiting the scope thereof, as obvious modifications and equivalents will be apparent to those skilled in the art, and the invention is therefore to be limited only by the scope of the appended claims.

EXAMPLE 1A

4-Cyano-4-phenylcyclohexano(b)

To an ice and methanol cooled solution of 4 g. (0.0205 M) of 4-cyano-4-phenylcyclohexanone (a) (prepared as in J. Chem. Soc. 1959, 1446) in 150 ml. of tetrahydrofuran, a suspension of 1 g. of sodium borohydride in 50 ml. of tetrahydrofuran is added in 5 ml. portions in the course of about 10 minutes. The mixture is stirred for about 30 minutes and allowed to stand in the cold for about 18 hours. The bulk of the solvent is removed under vacuum and the residue treated with water. The precipitate is extracted with ether and the organic fraction washed successively with 2.5 N hydrochloric acid solution, saturated aqueous sodium bicarbonate, water and brine and then evaporated to dryness. The residue is recrystallized with benzene to give 1.81 g. (43.8% yield) of 4-cyano-4-phenylcyclohexanol (b) melting at 103° to 111° C.

Anal. Calcd. for $C_{13}H_{15}NO$: C, 77.58; H, 7.51; N, 6.96

Found: C, 77.98; H, 7.34; N, 6.58.

Following the procedure of Example 1A but substituting other 4-cyano-4-phenylcyclohexanones (a) as starting materials, such as 1. 4-cyano-4-(4-bromophenyl)cyclohexanone(a),
2. 4-cyano-4-(3-fluorophenyl)cyclohexanone(a),
3. 4-cyano-4-(3-methylphenyl)cyclohexanone(a),
4. 4-cyano-4-(2-propylphenyl)cyclohexanone(a),
5. 4-cyano-4-(4-ethoxyphenyl)cyclohexanone(a),
6. 4-cyano-4-(3-aminophenyl)cyclohexanone(a),
7. 4-cyano-4-(4-methylaminophenyl)cyclohexanone(a),
8. 4-cyano-4-(5-ethylaminophenyl)cyclohexanone(a),
9. 4-cyano-4-(2-aceylamidophenyl)cyclohexanone(a), and the like, yields, respectively,
1. 4-cyano-4-(4-bromophenyl)cyclohexanol(b),
2. 4-cyano-4-(3-fluorophenyl)cyclohexanol(b),
3. 4-cyano-4-(3-methylphenyl)cyclohexanol(b),
4. 4-cyano-4-(2-propylphenyl)cyclohexanol(b),
5. 4-cyano-4-(4-ethoxyphenyl)cyclohexanol(b),
6. 4-cyano-4-(3-aminophenyl)cyclohexanol(b).

7. 4-cyano-4-(4-methylaminophenyl)cyclohexanol(b),
8. 4-cyano-4-(5-ethylaminophenyl)cyclohexanol(b),
9. 4-cyano-4-(2-acetylamidophenyl)cyclohexanol(b), and the like.

EXAMPLE 2A

4-Hydroxy-1-phenyl-1-cyclohexanecarboxaldehyde(c)

A solution of 2 g. (0.01 M) of 2 g. of 4-cyano-4-phenylcyclohexanol(b) (obtained as in Example 1A) in tetrahydrofuran is added to a suspension of 0.52 g. (0.015 M) of lithium aluminum hydride in 10 ml. of tetrahydrofuran. The mixture is stirred at room temperature for about 15 minutes, at reflux for about 1 hours, and then cooled in an ice bath. To it is added successively 0.52 ml. of water, 0.52 ml. of 15% aqueous sodium hydroxide solution and 1.56 ml. of water. The precipitated inorganic gel is collected on a filter, washed twice with ether and the combined filtrates evaporated to dryness. The residue is treated with 20 ml. of 1:1 acetic acid:water and 2 drops of concentrated sulfuric acid and heated on a steam bath for about 30 minutes. The mixture is cooled to room temperature, extracted thoroughly with methylene chloride, the combined extracts washed successively with water, saturated aqueous sodium bicarbonate solution and brine and then evaporated to dryness. The residual product, 1.37 g. (66% yield) of 4-hydroxy-1-phenyl-1-cyclohexanecarboxaldehyde(c) has a melting point of 74° to 76° C.

Anal. Calcd. for $C_{13}H_{16}O_2$: C, 76.44; H, 7.90. l.
Found: C, 76.06; H, 7.84.

Following the procedure of Example 2A but substituting other 4-cyano-4-phenylcyclohexanols(b) as starting materials, such as
1. 4-cyano-4-(5-chlorophenyl)cyclohexanol(b),
2. 4-cyano-4-(4-ethylphenyl)cyclohexanol(b),
3. 4-cyano-4-(3-propoxyphenyl)cyclohexanol(b),
4. 4-cyano-4-(5-isopropylaminophenyl)cyclohexanol(b),
5. 4-cyano-4-(4-propionylamidophenyl)cyclohexanol(b), and the like,
yields, respectively,
1. 4-hydroxy-1-(5-chlorophenyl)-1-cyclohexanecarboxaldehyde(c),
2. 4-hydroxy-1-(4-ethylphenyl)-1-cyclohexanecarboxaldehyde(c),
3. 4-hydroxy-1-(3-propoxyphenyl)-1-cyclohexanecarboxaldehyde(c),
4. 4-hydroxy-1-(5-isopropylaminophenyl)-1-cyclohexanecarboxaldehyde(c),
5. 4-hydroxy-1-(4-propionylamidophenyl)-1-cyclohexanecarboxaldehyde(c),
and the like.

EXAMPLE 3A

Ethyl-4-hydroxy-1-phenylcyclohexaneacrylate(f)

1. To a partial solution of 3.51 g. (0.017 M) of 4-hydroxy-1-phenyl-1-cyclohexanecarboxaldehyde(c) (obtained as in Example 2A) in 35 ml. of ether, 2 g. of dihydropyan and 0.11 g. of p- toluenesulfonic acid is added. After stirring for a short time at room temperature, complete solution is attained. The reaction mixture after standing at room temperature for about 4 hours is washed first with saturated aqueous sodium bicarbonate solution then with brine and evaporated to dryness. The residue is recrystallized once from petroleum ether to give 4.53 g. of 4-hydroxy-1-phenyl-1-cyclohexanecarboxaldehyde pyranyl ether (d), having a melting point of 43.5° to 54° C.

2. A solution of 3.52 g. (0.158M) of triethyl phosphonacetate in 45 ml. of tetrahydrofuran is prepared and 0.67 g. of 56% sodium hydride added. The mixture is stirred at room temperature for about 30 minutes and a solution of (0.158M) of the 4-hydroxy-1-phenyl-1-cyclohexanecarboxaldehyde pyranyl ether (d) [prepared as in (1), above], in 45 ml. of tetrahydrofuran added. Following about 4 hours of heating at reflux and about 15 hours of standing at room temperature, most of the solvent is removed under vacuum and the residue taken up in ether and water. The organic layer is washed with water and brine and then evaporated to dryness to give methyl-4-hydroxy-1-phenylcyclohexaneacrylate tetrahydropyranyl ether (e).

3. A solution of the methyl-4-hydroxy-1-phenylcyclohexaneacrylate tetrahydropyranyl ether (e) [prepared as in (2), above,] in 75 ml. of methanol and 7.5 ml. of 2.5 N hydrochloric acid is stirred at room temperature for about 1 hour and then most of the methanol removed under vacuum. The residue is dissolved in ether and water and the organic layer washed successively with water, saturated aqueous sodium bicarbonate solution and brine and then evaporated to dryness. The residue is chromatographed on a column of 500 g. of silica gel (silicic acid) with elution first by 5.5 l. of methylene chloride, then 20% ethyl acetate:methylene chloride. The more polar fractions found similar by thin layer chromatography (TLC) are combined to yield 3.5 g. (80% yield) of ethyl-4-hydroxy-1-phenylcyclohexaneacrylate(f) as a gum.

Following the procedure of Example 3A but substituting other 4-hydroxy-1-phenyl-1-cyclohexanecarboxaldehydes(c) as starting materials, such as
1. 4-hydroxy-1-(3-bromophenyl)-1-cyclohexanecarboxaldehyde(c),
2. 4-hydroxy-1-(4-propylphenyl)-1-cyclohexanecarboxaldehyde(c),
3. 4-hydroxy-1-(5-ethoxyphenyl)-1-cyclohexanecarboxaldehyde(c),
4. 4-hydroxy-1-(3-methylaminophenyl)-1-cyclohexanecarboxaldehyde(c),
5. 4-hydroxy-1-(2-formylamidophenyl-1-cyclohexanecarboxaldehyde(c), and the like,
yields, respectively,
1. ethyl-4-hydroxy-1-(3-bromophenyl)cyclohexaneacrylate(f),
2. ethyl-4-hydroxy-1-(4-propylphenyl)cyclohexaneacrylate(f),
3. ethyl-4-hydroxy-1-(5-ethoxyphenyl)cyclohexaneacrylate(f),
4. ethyl-4-hydroxy-1-(3-methylaminophenyl)cyclohexaneacrylate(f),
5. ethyl-4-hydroxy-1-(2-formylamidophenyl)cyclohexaneacrylate(f), and the like.

EXAMPLE 4A

Ethyl-4-hydroxy-1-phenylcyclohexane-3-propionate(g)

A mixture of 3.5 g. (0.0128 M) of ethyl-4-hydroxy-1-phenylcyclohexaneacrylate(f) (prepared in Example 3A), 150 ml. of ethyl acetate and 0.4 g. of palladium on carbon catalyst is hydrogenated until the theoretical amount of hydrogen is consumed. The catalyst is collected on a filter and the filtrate evaporated to dryness to give 3.36 g. (95% yield) of ethyl-4-hydroxy-1- phenylcyclohexane-3-propionate(g) as a gum.

Following the procedure of Example 4A but substituting other alkyl-4-hydroxy-1-phenylcyclohexaneacrylates(f) as starting materials, such as
1. methyl-4-hydroxy-1-(2-chlorophenyl)cyclohexaneacrylate(f),
2. propyl-4-hydroxy-1-(3-methoxyphenyl)cyclohexaneacrylate(f),
3. methyl-4-hydroxy-1-(5-ethylaminophenyl)cyclohexaneacrylate(f),
4. ethyl-4-hydroxy-1-(4-acetylamidophenyl)cyclohexaneacrylate(f), and the like,
yields, respectively,
1. methyl-4-hydroxy-1-(2-chlorophenyl)cyclohexane-3-propionate(g),
2. propyl-4-hydroxy-1-(3-methoxyphenyl)cyclohexane-3-propionate(g),
3. methyl-4-hydroxy-1-(5-ethylaminophenyl)cyclohexane-3-propionate(g),
4. ethyl-4-hydroxy-1-(4-acetylamidophenyl)cyclohexane-3-propionate(g), and the like.

EXAMPLE 5A

4-Hydroxy-1-phenylcyclohexane-3-propionic acid (h)

A solution of 0.68 g. (0.0025 M) of ethyl-4-hydroxy-1-phencyclohexane-3-propionate(g) (obtained in Example 4A) and 1 ml. of 50% sodium hydroxide in 10 ml. of methanol is heated at reflux for about 20 hours. Most of the solvent is removed under vacuum and the residue dissolved in water. The aqueous solution is washed with ether and made acidic with concentrated hydrochloric acid. A solid precipitate is collected on a filter and recrystallized from benzene to give 0.44 g. (71% yield) of 4-hydroxy-1-phenylcyclohexane-3-propionic acid (h) having a melting point of 153.5° to 155° C.

Anal. Calcd. for $C_{15}H_{20}O$: C, 72.55; H, 8.12.
Found: C, 72.47; H, 8.05.

Following the procedure of Example 5A but substituting other alkyl-4-hydroxy-1-phenylcyclohexane-3-propionates (g) as starting materials, such as
1. methyl-4-hydroxy-1-(3-fluorophenyl)cyclohexane-3-propionate(g),
2. isopropyl-4-hydroxy-1-(4-ethoxyphenylcyclohexane-3-propionate(g),
3. ethyl-4-hydroxy-1-(5-ethylaminophenyl)cyclohexane-3-propionate(g),
4. propyl-4-hydroxy-1-(4-acetylamidophenyl)cyclohexane-3-propionate(g), and the like,
yields, respectively,
1. 4-hydroxy-1-(3-fluorophenyl)cyclohexane-3-propionic acid(h),
2. 4-hydroxy-1-(4-ethoxyphenyl)cyclohexane-3-propionic acid(h),
3. 4-hydroxy-1-(5-ethylaminophenyl)cyclohexane-3-propionic acid(h),
4. 4-hydroxy-1-(4-acetylamidophenyl)cyclohexane-3-propionic acid(h), and the like.

EXAMPLE 6A

4-Oxo-1-phenylcyclohexane-3-propionic acid(i)

To a mechanically stirred, ice cooled partial solution of 2.36 g. (0.0095 M) of 4-hydroxy-1-phenylcyclohexane-3-propionic acid(h) (prepared as in Example 5A) in acetone, 5 ml. of Jones reagent (chromium trioxide-sulfuric acid) is added in the course of about 5 minutes. Most of the solvent is removed under vacuum and the residue dissolved in ether and water. The organic layer is washed with water and brine, evaporated to dryness and the residue recrystallized from methylene chloride: Skellysolve B to give 2.13 g. (91.2% yield) of 4-oxo-1-phenylcyclohexane-3-propionic acid(i) having a melting point of 139° to 140.5° C.

Anal. Calcd. for $C_{15}H_{18}O_3$: C, 73.14; H, 7.37.
Found: C, 72.49; H, 7.27.

Following the procedure of Example 6A but substituting other 4-hydroxy-1-phenylcyclohexane-3-propionic acids(h) as starting materials, such as
1. 4-hydroxy-1-(3-bromophenyl) cyclohexane-3-propionic acid(h),
2. 4-hydroxy-1-(3-ethylphenyl)cyclohexane-3-propionic acid(h),
3. 4-hydroxy-1-(5-methylaminophenyl)cyclohexane-3-propionic acid(h), and the like, yields, respectively,
1. 4-oxo-1-(2-bromophenyl)cyclohexane-3-propionic acid(i),
2. 4-oxo-1-(3-ethylphenyl)cyclohexane-3-propionic acid(i),
3. 4-oxo-1-(5-methylaminophenyl)cyclohexane-3-propionic acid(i), and the like.

EXAMPLE 7A

4-Cyano-4-phenylcyclohexanone, ethylene ketal(j)

A mixture of 10 g. (0.05 M) of 4-cyano-4-cyano-4-phenylcyclohexanone(a), 2.85 ml. [3.16 g. (0.51M)] of ethylene glycol and 0.12 g. of p-toluenesulfonic acid in 90 ml. of benzene is heated at reflux under a Dean-Stark trap for about 6 hours. The solution is allowed to cool and then washed successively with sodium bicarbonate solution, water and brine. The organic layer is evaporated to dryness and the residue recrystallized from cyclohexane to give 11.27 g. (92.7% yield) of 4-cyano-4-phenylcyclohexanone, ethylene ketal(j), having a melting point of 120° to 122.5° C.

Anal. Calcd. for $C_{15}H_{17}NO_2$: C, 74.05; H, 7.04; N, 5.76
Found: C, 74.10; H, 6.98; N, 5.77.

Following the procedure of Example 7A but substituting other 4-cyano-4-phenylcyclohexanones(a) as starting materials, such as
1. 4-cyano-4-(4-chlorophenyl)cyclohexanone(a),
2. 4-cyano-4-(4-methoxyphenyl)cylohexanone(a),
3. 4-cyano-4-(3-ethylaminophenyl)cyclohexanone(a),
4. 4-cyano-4-(2-propionylamidophenyl)cyclohexanone(a), and the like,
yields, respectively,
1. 4-cyano-4-(4-chlorophenyl)cyclohexanone, ethylene ketal(j),
2. 4-cyano-4-(4-methoxyphenyl)cyclohexanone, ethylene ketal(j),
3. 4-cyano-4-(3-ethylaminophenyl)cyclohexanone, ethylene ketal (j),
4. 4-cyano-4-(2-propionylamidophenyl)cyclohexanone, ethylene ketal(j), and the like.

EXAMPLE 8A

4-Oxo-1-phenylcyclohexanecarboxaldehyde, 4-ethylene ketal(k)

To a suspension of 0.16 g. (0.0014 M) of lithium aluminum hydride in 10 ml. of tetrahydrofuran, 2 g. (0.0082 M) of 4-cyano-4-phenylcyclohexanone ethylene ketal(j) (prepared as in Example 7A) in 100 ml. of tetrahydrofuran is added in the course of about 15 minutes. The mixture is stirred at room temperature for about 1.75 hours and then cooled in an ice bath, and then 0.16 ml. of water, 0.16 ml. of 15% aqueous sodium hydroxide solution and 0.48 ml. of water added successively, The inorganic gel is collected on a filter, rinsed with ether and the combined filtrates evaporated to dryness. The residue in 30 ml. of tetrahydrofuran and 3 ml. of 2.5 N hydrochloric acid is stirred at room temperature for about 15 minutes, treated with 1 g. of sodium bicarbonate and then evaporated to dryness under vacuum. Ether is added to the residue, the organic portion separated and evaporated to dryness. The residue is chromatographed on silica gel, eluted with 1% ethyl acetate: methylene chloride and the more polar crystalline fractions combined to yield 0.87 g. (86.4 % of theoretical) of 4-oxo-1-phenylcyclohexanecarboxaldehyde, 4-ethylene ketal(k), having a melting point of 56° to 64° C. and nuclear magnetic resonance (NMR) and infrared (IR) spectra in agreement with the expected structure of the compound.

Following the procedure of Example 8A but substituting other 4-cyano-4-phenylcyclohexane ethylene ketals(j) as starting materials, such as 1. 4-cyano-4-(3-fluorophenyl)cyclohexanone, ethylene ketal(j),
2. 4-cyano-4-(2-ethylphenyl)cyclohexanone, ethylene ketal(j),
3. 4-cyano-4-(4-propylaminophenylcyclohexanone, ethylene ketal(j),
4. 4-cyano-4-(5-acetylamidophenyl)cyclohexanone, ethylene ketal(j), and the like, yields, respectively, 1. 4-oxo-1-(3-fluorophenyl)cyclohexanecarboxaldehyde, ethylene ketal(k),
2. 4-oxo-1-(2-ethylphenyl)cyclohexanecarboxaldehyde, ethylene ketal(k),
3. 4-oxo-1-(4-propylaminophenyl)cyclohexanecarboxaldehyde, ethylene ketal(k),
4. 4-oxo-1-(5-acetylamidophenyl)cyclohexanecarboxaldehyde, ethylene ketal(k), and the like.

EXAMPLE 9A

Ethyl -4-oxo-1-phenylcyclohexaneacrylate, ethylene ketal(l)

To a solution of 4.74 g. (0.021 M) of triethyl phosphonoacetate in 60 ml. of tetrahydrofuran, 0.89 g. of 57% sodium hydride is added. Following about 10 minutes of stirring at room temperature a solution of 5.2 g (0.021 M) of 4-oxo-1-phenylcyclohexanecarboxaldehyde 4-ethylene ketal(k) (prepared as in Example 8A) in 60 ml. of tetrahydrofuran is added. The solution is stirred at reflux for about 4 hours and at room temperature for about 18 hours. Most of the solvent is removed under vacuum, and the residue dissolved in ether and water. The organic layer is washed with water and brine and then evaporated to dryness. The residue is chromatographed over a column of 700 ml. of silica gel and eluted, first, with 1,600 ml. of Skellysolve B, then with 4 l. of 5% acetone: Skellysolve B. The ultraviolet absorbing fractions found to be alike by TLC are combined to give 6.38 g. (96% yield) of ethyl-4-oxo-1-phenylcyclohexaneacrylate ethylene ketal(l.) as a gum.

Following the procedure of Example 9A but substituting other 4-oxo-1-phenylcyclohexanecarboxaldehyde 4-ethylene ketals(k) as starting materials, such as 1. 4-oxo-1-(2-bromophenyl)cyclohexanecarboxaldehyde, ethylene ketal(k),
2. 4-oxo-1-(3-ethoxyphenyl)cyclohexanecarboxaldehyde, ethylene ketal(k), and the like, yields, respectively,
1. ethyl-4-oxo-1-(2-bromophenyl)cyclohexaneacrylate, ethylene ketal(1),
2. ethyl-4-oxo-1-(3-ethoxyphenyl)cyclohexaneacrylate, ethylene ketal(l), and the like.

EXAMPLE 10A

Ethyl-4-oxo-1-phenylcyclohexane-3-propionate, ethylene ketal(m)

A mixture of 6.38 g. (0.0202 M) of ethyl-4-oxo-1-phenylcyclohexaneacrylate ethylene ketal(l) (obtained in Example 9A), 0.63 g. of 10% palladium on carbon catalyst and 150 ml. of ethyl acetate is shaken under an atomsphere of hydrogen until the theoretical amount is consumed. The catalyst is collected on a filter and the filtrate evaporated to dryness to give 6.38 g. (about 100% of theoretical yield) of ethyl-4-oxo-1-phenylcyclohexane-3-propionate, ethylene ketal(m) as a crude oil.

Following the procedure of Example 10A but substituting other alkyl-4-oxo-1-phenylcyclohexaneacrylate ethylene ketals(m) as starting materials, such as 1. ethyl-4-oxo-1-(3-methylphenyl)cyclohexaneacrylate, ethylene ketal(l), and the like, yields, 1. ethyl-4-oxo-1-(3-methylphenyl)cyclohexane-3-propionate, ethylene ketal(m), and the like.

EXAMPLE 11A

4-Oxo-1-phenylcyclohexane-3-propionic acid, ethylene ketal(n)

A solution of 6.38 g. (0.020 M) of ethyl-4-oxo-1-phenylcyclohexane-3-propionate ethylene ketal(m) (obtained in Example 10A) and 8 ml. of 50% sodium hydroxide solution in 80 ml. of methanol is heated at reflux for about 20 hours. Most of the methanol is removed under vacuum, water added to the residue and the latter washed with ether. The aqueous layer is then made strongly acidic and the material that precipitates is extracted with ether. The combined ether extracts are washed with brine and evaporated to dryness to give 4-oxo-1-phenylcyclohexane-3-propionic acid, ethylene ketal(n).

Following the procedure of Example 11A but substituting other alkyl-4-oxo-1-phenylcyclohexane-3-propionate ethylene ketals(m) as starting materials, such as 1. propyl-4-oxo-1-(5-ethoxyphenyl)cyclohexane-3-propionate, ethylene ketal(m),
2. methyl-4-oxo-1-(3-acetylamidophenylcyclohexane- 3-propionate, ethylene ketal(m), and the like, yields, respectively, 1. 4-oxo-1-(5-ethoxyphenyl)cyclohexane-3-propionic acid, ethylene ketal(n),
2. 4-oxo-1-(3-acetylamidophenyl)cyclohexane-3-propionic acid, ethylene ketal(n), and the like.

EXAMPLE 12A

4-Oxo-1-phenylcyclohexane-3-propionic acid(i)

The 4-oxo-1-phenylcyclohexane-3-propionic acid ethylene ketal(n) obtained in Example 11A is dissolved in 50 ml. of acetone and 5 ml. of 2.5 N hydrochloric acid and allowed to stand at room temperature for about 48 hours. The solution is evaporated to near dryness under vacuum and the residue dissolved in water and ether. The organic layer is washed with water and brine and evaporated to dryness. The residue is recrystallized from methylene chloride: Skellysolve B to give 1.7 g. (34.5% yield of 4-oxo-1-phenylcyclohexane-3-propionic acid(i) having a melting point of 143° to 144.5° C. This compound is identical to the compound prepared in Example 6A.

Anal. Calcd. for $C_{15}H_{18}O_3$: C, 73.15; H, 7.37.
Found: C, 73.04; H, 7.40.

Following the procedure of Example 12A but substituting other 4-oxo-1-phenylcyclohexane-3-propionic acid alkylene ketals(n) as starting materials, such as
1. 4-oxo-1-(3-chlorophenyl)cyclohexane-3-propionic acid, ethylene ketal(n),
2. 4-oxo-1-(4-isopropylphenyl)cyclohexane-3-propionic acid, ethylene ketal(n),
3. 4-oxo-1-(5-methylaminophenyl)cyclohexane-3-propionic acid, ethylene ketal(n), and the like, yields, respectively,
1. 4-oxo-1-(3-chlorophenyl)cyclohexane-3-propionic acid(i),
2. 4-oxo-1-(4-isopropylphenyl)cyclohexane-3-propionic acid(i),
3. 4-oxo-1-(5-methylaminophenyl)cyclohexane-3-propionic acid(i), and the like.

EXAMPLE 13A

Spiro [cyclohexane-1,1'(2'H)-naphthalene]-4,4'(-3'H)dione(o)

To 5 g. (0.0203 M) of 4-oxo-1-phenylcyclohexane-3-propionic acid(i) (prepared as in Examples 6A or 12A), 5 ml. of hydrogen fluoride is distilled and the solution allowed to stand at room temperature for about 20 hours. The residue is dissolved in ether, washed successively with water, saturated aqueous sodium bicarbonate solution and brine and then evaporated to dryness. The residue is recrystallized from ether to give 0.13 g. (28% of theoretical yield) of spiro[cyclohexane-1,1'(2'H)-naphthalene]-4,4'(3'H)-dione(o) having a melting point of 145.5° to 148° C.

Calcd. for $C_{15}H_{16}O_2$: C, 78.23; H, 7.88
Found: C, 78.39; H, 7.18

Following the procedure of Example 13A but substituting other 4-oxo-1-phenylcyclohexane-3-propionic acids(i) as starting materials, such as
1. 4-oxo-1-(3-propylphenyl)cyclohexane-3-propionic acid(i),
2. 4-oxo-1-(4-ethoxyphenyl)cyclohexane-3-propionic acid(i),
3. 4-oxo-1-(2-ethylaminophenyl)cyclohexane-3-propionic acid(i),
4. 4-oxo-1-(3-acetylamidophenyl)cyclohexane-3-propionic acid(i), and the like, yields, respectively,
1. 6'-propylspiro[cyclohexane-1,1'(2'H)naphthalene]-4,4'(3'H)-dione(o),
2. 7'-ethoxyspiro[cyclohexane-1,1'(2'H)-naphthalene]-4,4'(3'H)-dione(o),
3. 5'-ethylaminospiro[cyclohexane-1,1'(2'H)-naphthalene]-4,4'(3'H)-dione(o),
4. 6'-acetylamidospiro[cyclohexane-1,1'(2'H)-naphthalene]-4,4'(3'H)-dione(o), and the like.

EXAMPLE 14A

Spiro[cyclohexane-1,1'(2'H)-naphthalene]-4,4'(-3'H)-dione, 4-(2,2-dimethyltrimethylene ketal)(p)

A solution of 3.19 g. (0.014 M) of spiro[cyclohexane-1,1'(2'H)-naphthalene]-4,4'(3'H)-dione(o) (prepared as in Example 13A), 1.45 g. (0.014 M) of 2,2-dimethylpropanediol and 0.06 g. of p-toluenesulfonic acid in 57 ml. of benzene is heated under a Dean-Stark trap for about 5.5 hours. The solution is washed with saturated aqueous sodium bicarbonate and brine and then evaporated to dryness. The residue is chromatographed over a column of 400 ml. of Florisil (activated magnesium silicate) and eluted with 7.5% ethyl acetate; Skellysolve B. The crystalline fractions are combined to yield 3.29 g. (75% of theoretical) of spiro[cyclohexane-1,1'(2'H)-naphthalene]4,4'(3'H)-dione, 4-(2,2-dimethyltrimethylene ketal) (p) having a melting point of 136° to 138° C.

Anal. Calcd. for $C_{20}H_{26}O_3$: C, 76.40; H, 8.34
Found: C, 76.49; H, 8.38.

Following the procedure of Example 14A but substituting other spiro[cyclohexane-1,1'(2'H)-naphthalene]-4,4'-(3'H)-diones(o) as starting materials, such as
1. 5'-fluorospiro[cyclohexane-1,1'(2'H)-naphthalene]-4,4'(3'H)-dione(o),
2. 6'-methylspiro[cyclohexane-1,1'(2'H)-naphthalene]-4,4'(3'H)-dione(o), and the like, yields, respectively,
1. 5'-fluorospiro[cyclohexane-1,1'(2'H)-naphthalene]-4,4'(3'H)-dione, 4-(2,2-dimethyltrimethylene ketal)(p),
2. 6'-methylspiro[cyclohexane-1,1'(2'H)-naphthalene]-4,4'(3'H)-dione, 4-(2,2-dimethyltrimethylene ketal)(p), and the like.

EXAMPLE 15A

3',4'-Dihydrospiro[cyclohexane-1,1'(2'H)-naphthalen]-4-one, 2,2-dimethyltrimethylene ketal(q)

A solution of 3.63 g. (0.0115 M) of spiro[cyclohexane-1,1'(2'H)-naphthalene]-4,4'(3'H)-dione, 4-(2,2-dimethyltrimethylene ketal(p) (prepared as in Example 14A), 1.54 ml. of hydrazine hydrate and 2.23 g. of potassium hydroxide in 28 ml. of ethylene glycol is heated to reflux. Distillate is collected until the pot temperature rises to 200° C. and refluxing is continued for about 18 hours. The mixture is poured into water and a precipitated material is extracted with ether. The combined extracts are washed with water and brine and then evaporated to dryness. The residue is recrystallized from petroleum ether to give 2.39 g. (69.5% yield) of 3',4'-dihydrospiro[cyclohexane-1,1'(2'H)-naphthalene]-4-one, 2,2-dimethyltrimethylene ketal(q) having a melting point of 109° to 111° C.

Anal. Calcd. for $C_{20}H_{28}O_2$: C, 79.95; H, 9.39
Found: C, 79.95; H, 9.51.

Following the procedure of Example 15A but substituting other 3',4'-dihydrospiro[cyclohexane-1,1'(-2'H)-naphthalene]-4,4'(3'H)-dione, 4-(2,2-dimethyltrimethylene ketals) (p) as starting materials, such as
1. 5'-fluorospiro[cyclohexane-1,1'(2'H)-naphthalene]-4,4'(3'H)-dione, 4-(2,2-dimethyltrimethylene ketal)(p),
2. 6'-nitrospiro[cyclohexane-1,1'(2'H)-naphthalene]-4,4'(3'H)-dione, 4-(2,2-dimethyltrimethylene ketal)(p), and the like, yields, respectively,
1. 5'-fluorospiro[cyclohexane-1,1'(2'H)-naphthalen]-4-one, 2,2-dimethyltrimethylene ketal(q),
2. 6'-nitrospiro[cyclohexane-1,1'(2'H)-naphthalen]-4-one, 2,2-dimethyltrimethylene ketal(q), and the like.

EXAMPLE 16A

3',4'-Dihydrospiro[cyclohexane-1,1'(2'H)-naphthalen]-4-one(r)

A mixture of 2.39 g. (0.008 M) of 3',4'-dihydrospiro[cyclohexane-1,1'(2'H)-naphthalen]-4-one, 2,2-dimethyltrimethylene ketal(q) and 2.4 ml. of 2.5 N hydrochloric acid in 24 ml. of acetone is stirred at room temperature for about 6 hours. To the reaction mixture, 15 ml. of water is added and most of the acetone removed under vacuum. Ether is added to the residue, the organic layer washed successively with water, saturated aqueous sodium bicarbonate solution and brine and then evaporated to dryness. The residue is recrystallized from petroleum ether to give 1.19 g. (70% yield) of 3',4'-dihydrospiro[cyclohexane-1,1'(2'H)-naphthalen]-4-one(r) having a melting point of 115° to 120° C.

Following the procedure of Example 16A but substituting other 3',4'-dihydrospiro[cyclohexane-1,1'(-2'H)-naphthalen]-4-one, 2,2-dimethyltriethylene ketals(q) as starting materials, such as 1. 2'-chlorospiro[cyclohexane-1,1'(2'H)-naphthalen]-4-one, 2,2-dimethyltrimethylene ketal(q),
2. 3'-methoxyspiro[cyclohexane-1,1'(2'H)-naphthalen]-4-one, 2,2-dimethyltrimethylene ketal(q),
3. 4'-acetylamidospiro[cyclohexane-1,1'(2'H)-naphthalen]-4-one, 2,2-dimethyltrimethylene ketal(q), and the like, yields, respectively, 1. 2'-chlorospiro[cyclohexane-1,1'(2'H)-naphthalen]-4-one(r),
2. 3'-methoxyspiro[cyclohexane-1,1'(2'H)-naphthalen]-4-one(r),
3. 4'-acetylamidospiro[cyclohexane-1,1'(2'H)-naphthalen]-4-one(r), and the like.

EXAMPLE 17A

3',4'-Dihydrospiro[cyclohexane-1,1'(2'H)-naphthalen]-4-ol(s)

To a partial solution of 5.10 g. (0.038 M) of 3',4'-dihydrospiro[cyclohexane-1,1'(2'H)-naphthalen-4-one(r) (prepared as in Example 16A) in 105 ml. of 95% ethanol, 2.59 g. of sodium borohydride is added and the mixture stirred at room temperature for about 4 hours. Most of the solvent is removed under vacuum and water added to the residue. The material that precipitates is extracted with ether and the combined extracts washed with water and brine and evaporated to dryness. The residue is recrystallized once from Skellysolve B and then chromatographed over a column containing 500 ml. of silica gel with elution by 10% acetone:Skellysolve B. On the basis of TLC the less polar fractions are combined and recrystallized from benzene:cyclohexane to give a small amount of 3',4'-dihydrospiro[cyclohexane-1,1'(2'H)-naphthalen]-4-ol(s), having a melting point of 144.5° to 146° C., and an NMR spectrum suggesting that the compound has the hydroxy substituent in the axial position.

Anal. Calcd. for $C_{15}H_{20}O$: C, 83.28; H, 9.32
Found: C, 83.53; H, 9.61.

On the basis of melting point the more polar fractions are combined and recrystallized from Skellysolve B to give 3.89 g. (75.6% yield) of 3',4'-dihydrospiro[cyclohexane-1,1'(2'H)-naphthalen]-4-ol(s) having a melting point of 80° to 83° C., and an NMR spectrum suggesting that the compound has the hydroxy substituent in the equatorial position.

Anal. Calcd. for $C_{15}H_{20}O$: C, 83.28; H, 9.32
Found: C, 83.47; H, 9.55.

Following the procedure of Example 17A but substituting other 3',4'-dihydrospiro[cyclohexane-1,1'(-2'H)-naphthalen]-4-ones(r) as starting materials, such as 1. 5'-bromospiro[cyclohexane-1,1'(2'H)-naphthalen]-4-one(r),
2. 6'-ethylspiro[cyclohexane-1,1'(2'H)-naphthalen]-4-one(r), and the like, yields, respectively, 1. trans and cis 5'-bromospiro[cyclohexane-1,1'(-2'H)-naphthalen]-4-ol(s),
2. trans and cis 6'-ethylspiro[cyclohexane-1,1'(2'H)-naphthalen]-4-ol(s), and the like.

EXAMPLE 18A

3',4'-Dihydrospiro[cyclohexane-1,1'(2'H)-naphthalen]-4-ol, methane sulfonate(t)

To an ice-cooled solution of 3.89 g. (0.018 M) of 3',4'-dihydrospiro[cyclohexane-1,1'(2'H)-naphthalen]-4ol (obtained in Example 17A) in 40 ml. of pyridine, 4 ml. of methane sulfonyl chloride is added. The mixture is allowed to stand in the cold for about 6 hours and then diluted with water. The material that precipitates is extracted with ether and the combined extracts washed successively with ice cold 2.5 N hydrochloric acid, water, saturated aqueous sodium bicarbonate solution and brine and then evaporated to dryness. The residue is recrystallized from cyclohexane to give 5 g. (94.3% yield) of 3',4'-dihydrospiro[cyclohexane-1,1'(2'H)-naphthalen]-4-ol methane sulfonate(t), having a melting point of 118° to 120° C.

Anal. Calcd. for $C_{16}H_{22}O_3S$: C, 65.27; H, 7.53; S, 10.89
Found: C, 65.17; H, 7.61; S, 10.70

Following the procedure of Example 18A but substituting other 3',4'-dihydrospiro[cyclohexane-1,1'(-2'H)-naphthalen]-4-ols(s) as starting materials, such as 1. 6'-fluorospiro[cyclohexane-1,1'(2'H)-naphthalen]-4-ol(s),
2. 8'-propoxyspiro[cyclohexane-1,1'(2'H)-naphthalen]-4-ol(s), and the like, yields, respectively, 1. 6'-fluorospiro[cyclohexan-1,1'(2'H)-naphthalen]-4-ol methane sulfonate(t),
2. 8'-propoxyspiro[cyclohexane-1,1'(2'H)-naphthalen]-4-ol methane sulfonate(t), and the like.

EXAMPLE 19A

3',4'-Dihydrospiro[cyclohexane-1,1'(2'H)-naphthalen]-4-yiazide(u)

A mixture of 5 g. (0.017 M) of 3',4'-dihydrospiro[cyclohexane-1,1'(2'H)-naphthalen]-4-ol methane sulfonate(t) (obtained in Example 18A) and 5 g. of sodium azide in 50 ml. of dimethylformamide is heated in an oil bath at 90° C. for about 20 hours. Most of the solvent is removed under vacuum and the residue dissolved in water and benzene. The organic layer is washed with water and brine and evaporated to dryness to yield crude 3',4'-dihydrospiro[cyclohexane-1,1(2'H)-naphthalen]-4-ylazide(u) as an oil.

Following the procedure of Example 19A but substituting other 3',4'-dihydrospiro[cyclohexane-1,1'(-2'H)-naphthalen]-4-ylazides(t) as starting materials, such as 1. 5'-ethylspiro[cyclohexane-1,1'(2'H)-naphthalen]-4-ol methanesulfonate(t), 2. 6'-acetylamidospiro[cyclohexane-1,1'(2'H)-naphthalen]-4-ol methanesulfonate(t), and the like, yields, respectively,
1. 5'-ethylspiro[cyclohexane-1,1'(2'H)-naphthalen]-4-ylazide(u),
2. 6'-acetylamido[cyclohexane-1,1'(2'H)-naphthalen]-4-ylazide(u), and the like.

EXAMPLE 20A

3',4'-Dihydrospiro[cyclohexane-1,1'(2'H)-naphthalen]-4-ylamine hydrochloride[I(a)]

A solution of the 3',4'-dihydrospiro[cyclohexan-1,1'-(2'H)-naphthalen]-4-ylazide(u) obtained in Example 19A in 75 ml. of tetrahydrofuran, is added to suspension of 0.65 g. of lithium aluminum hydride in 8 ml. of tetrahydrofuran, stirred at room temperature for about 5.5 hours and cooled in an ice bath. To this, 0.65 ml. of water, 0.65 ml. of 15% aqueous sodium hydroxide and 1.95 ml. of water are added successively. The resulting gel is collected on a filter, washed with ether and the filtrates evaporated to dryness. The residue is dissolved in a small amount of ether and an excess of 6.4 N hydrogen chloride in ether added. The precipitate is collected on a filter and recrystallized from methanol:ethyl acetate to yield 1.76 g. of 3',4'-dihydro[cyclohexane-1,1'(2'H)-naphthalen]-4-yl-amine hydrochloride[I(a)] melting at 271° to 273° C.

Following the procedure of Example 20A but substituting for hydrogen chloride another suitable (pharmacologically acceptable) acid, such as hydrobromic, sulfuric, phosphoric, nitric, benzoic, naphthoic, salicylic, tartaric, nicotinic, cyclohexanesulfamic, hexynoic, lactic, palmitic, glutaric, acetic, propionic, phenylbutyric acid, and the like, yields a corresponding acid addition salt of 3',4'-dihydrospiro[cyclohexane-1,1'(2'H)-naphthalen]-4-ylamine [I(a)].

Following the procedure of Example 20A but substituting another 3',4'-dihydrospiro[cyclohexane-1,1'(-2'H)-naphthalen]-4-ylazide(u) as starting material, such as
1. 5'-chlorospiro[cyclohexane-1,1'(2'H)-naphthalen]-4-ylazide(u),
2. 6'-methoxyspiro[cyclohexane-1,1'(2'H)-naphthalen]-4-ylazide(u), and the like, yields, respectively,
1. 5'-chlorospiro[cyclohexane-1,1'(2'H)-naphthalen]-4-ylamine hydrochloride[I(a)],
2. 6'-methoxyspiro[cyclohexane-1,1'(2'H)-naphthalen]-4-ylamine hydrochloride[I(a)], and the like.

EXAMPLE 21A

1-[3',4'-Dihydrospiro(cyclohexane-1,1'(2'H)-naphthlen)-4-yl]piperidine[I(a)]

The amine prepared from 1.5 g. of 3',4'-dihydrospiro[cyclohexane-1,1'(2'H)-naphthalen]-4-ylamine hydrochloride [I(a)] (obtained as in Example 20A), 1.9 g. of 1.5-diiodopentane and 1.6 g. of potassium carbonate in 18 ml. of ethanol is stirred at reflux for about 18 hours. The mixture is allowed to cool, diluted with water, the solid collected on a filter and recrystallized from methanol to give 1-[3',4'-dihydrospiro(cyclohexane-1,1'(2'H)-naphthalen4-yl]piperidine[I(a)].

Following the procedure of Example 21A but substituting the same and other (a) acid addition salts of 3',4'-dihydrospiro[cyclohexane-1,1'(2'H)-naphthalen]-4-ylamines[I(a)] and (b) dihaloalkanes in stoichiometrically appropriate amounts as starting materials, such as
1. 3',4'-dihydrospiro[cyclohexane-1,1'(2'H)-naphthalen]-4-ylamine[I(a)] and 1,4-dibromobutane,
2. 3',4'-dihydrospiro[cyclohexane-1,1'(2'H)-naphthalen]-4-ylamine[I(a)] and 1,6-diiodohexane,
3. 5'-bromospiro[cyclohexane-1,1'(2'H)-naphthalen]-4-ylamine[I(a)] and 1,5-diiodopentane,
4. 6'-ethylspiro[cyclohexane-1,1'(2'H)-naphthalen]-4-ylamine[I(a)] and 1,4-diiodobutane,
5. 7'-propoxyspiro[cyclohexane-1,1'(2'H)-naphthalen]-4-ylamine[I(a)] and 1,6-diiodohexane, and the like, yields, respectively,
1. 1-[3',4'-dihydrospiro(cyclohexane-1,1'(2'H)-naphthalen)-4-yl]pyrrolidine[I(a)],
2. 1-[3',4'-dihydrospiro(cyclohexane-1,1'(2'H)-naphthalen)-4-yl]hexamethyleneimine[I(a)],
3. 1-[5'-bromospiro(cyclohexane-1,1'(2'H)-naphthalen)-4-yl]piperidine[I(a)],
4. 1-[6'-ethylspiro(cyclohexane-1,1'(2'H)-naphthalen)-4-yl]pyrrolidine[I(a)],
5. 1-[7'-propoxyspiro(cyclohexane-1,1'-(2'H)-naphthalen)-4-yl]hexamethyleneimine[I(a)], and the like.

EXAMPLE 22A

4'-Fluoro-4-[3',4'-dihydrospiro[cyclohexane-1,1'(-2'H)-naphthalen]-4-ylamino]butyrophenone hydrochloride [I(a)]

A mixture of the free base prepared from 1 g. (0.00397 M) of 3',4'-dihydrospiro[cyclohexane-1,1'(-2'H)-naphthalen]-4-ylamine hydrochloride [I(a)] (obtained as in Example 20A), 0.81 g. of potassium iodide, 1.24 g. of potassium carbonate and 1.4 g. of the 2,2-dimethyl-1,3-propanediol ketal of 4-chloro-4'-fluorobutyrophenone in 20 ml. of dimethylformamide is heated together in an oil bath at about 90° C. for about 20 hours. The solvent is removed under vacuum and the residue dissolved in water and benzene. The organic layer is washed with water and brine and evaporated to dryness. A mixture of the residue, 8 ml. of 2.5 N hydrochloric acid and 16 ml. of methanol is stirred at room temperature for about 2 hours and most of the methanol removed under vacuum. The residual suspended solid is collected on a filter, washed with ether and recrystallized from methanol:ethyl acetate to give 0.65 g. (39.5% yield) of 4'-fluoro-4-[3',4'-dihydrospiro[cyclohexane-1,1'(2'H)-naphthalen]-4-yl-amino]butyrophenone hydrochloride[I(a)], having a melting point of 194° to 197° C.

Anal. Calcd. for $C_{25}H_{31}ClFNO$: C, 72.18; H, 7.51; N, 3.37,

Found: C, 72.42; H, 7.66; N, 3.14.

Following the procedure of Example 22A but substituting another 3',4'-dihydrospiro[cyclohexane-1,1'(-2'H)-naphthalen]-4-ylamine hydrochloride [I(a)] as starting material, such as
1. 5'-chlorospiro[cyclohexane-1,1'(2'H)-naphthalen]-4-ylamine hydrochloride[I(a)],
2. 6'-ethoxyspiro[cyclohexane-1,1'(2'H)-naphthalen]-4-ylamine hydrochloride[I(a)],
3. 7'-acetylamidospiro[cyclohexane-naphthalen]-4-ylamine hydrochloride[I(a)], and the like, yields, respectively,
1. 4'-fluoro-4-[5'-chlorospiro[cyclohexane-1,1'(-2'H)-naphthalen]-4-ylamino]butyrophenone hydrochloride[I(a)], 2. 4'-fluoro-4-[6'-ethoxyspiro[cyclohexane-1,1'(-2'H)-naphthalen]-4-ylamino]butyrophenone hydrochloride[I(a)],
3. 4'-fluoro-4-[7'-acetylamidospiro[cyclohexane-1,1'(2'H)-naphthalen]-4-ylamino]butyrophenone hydrochloride [I(a)], and the like.

Following the procedure of Example 22A but substituting another 3',4'-dihydrospiro[cyclohexane-1,1'(-2'H)-naphthalen]-4-ylamine[I(a)] as starting material and the 2,2-dimethyl-1,3-propanediol ketal of another ω-haloalkanaryl ketone, such as 1. 5'-chlorospiro[cyclohexane-1,1'(2'H)-naphthalen]-4-ylamine hydrochloride[I(a)] and the 2,2-dimethyl-1,3-propanediol ketal of 4'-bromo-4-chlorobutyrophenone,
2. 6'-methylspiro[cyclohexane-1,1'(2'H)-naphthalen]-4-ylamine hydrochloride[I(a)] and the 2,2-dimethyl-1,3-propanediol ketal of 4-chloro-4'-ethoxybutyrophenone,
3. 7'-nitrospiro[cyclohexane-1,1'(2'H)-naphthalen]-4-ylamine hydrochloride[I(a)] and the 2,2-dimethyl-1,3-propanediol ketal of 3',4-dichlorobutyrophenone,
4. 6'-propionylamidospiro[cyclohexane-1,1'(2'H)-naphthalen]-4-ylamine hydrochloride[I(a)] and the 2,2-dimethyl-1,3-propanediol ketal of 5-chloro-4'-ethylvalerophenone, and the like, yields, respectively, 1. 4'-bromo-4-[5'-chlorospiro[cyclohexane-1,1'(-2'H)-naphthalen]-4-ylamino]butyrophenone hydrochloride[I(a)],
2. 4'-ethoxy-4-[6'-methylspiro[cyclohexane-1,1'(-2'H)-naphthalen]-4-ylamino]butyrophenone hydrochloride[I(a)],
3. 3'-chloro-4-[7'-nitrospiro[cyclohexane-1,1'(2'H)-naphthalen]-4-ylamino]butyrophenone hydrochloride [I(a)],
4. 4'-ethyl-5-[6'-propionylamido[cyclohexane-1,1'(-2'H)-naphthalen]-4-ylamino]valerophenone[I(a)], and the like.

EXAMPLE 23A

Ethyl 3',4'-dihydrospiro[cyclohexane-1,1'(2'H)-naphthalene]-4-carbamate[I(a)]

To an ice cooled solution of the free base prepared from 1.53 g. (0.0061 M) of 3',4'-dihydrospiro[cyclohexane-1,1'(2'H)-naphthalen]-4-ylamine hydrochloride[I(a)] (obtained as in Example 20A) in 12 ml. of pyridine, 0.95 ml. of ethyl chloroformate is added. The mixture is allowed to stand in the cold for about 5 hours and then poured in ice water. The solid that precipitates is collected on a filter and recrystallized from methylene chloride:benzene to give 1.36 g. (77.7% yield) of ethyl 3',4'-dihydrospiro[cyclohexane-1,1'(2'H)-naphthalen]-4-carbamate[I(a)], melting at 163.5° to 165° C.

Anal. Calcd. for $C_{18}H_{25}NO_2$: C, 75.22; H, 8.77; N, 4.87

Found: C, 74.91; H, 8.77; N, 4.83.

Following the procedure of Example 23A but substituting another 3',4'-dihydrospiro[cyclohexane-1,1'(-2'H)-naphthalen]-4-ylamine[I(a)] as starting material and another lower alkyl haloformate, such as 1. 5'-bromospiro[cyclohexane-1,1'(2'H)-naphthalen]-4-ylamine[I(a)] and methyl chloroformate,
2. 6'-ethoxyspiro[cyclohexane-1,1'(2'H)-naphthalen]-4-ylamine[I(a)] and propyl bromoformate, and the like, yields, respectively,
1. methyl 5'-bromospiro[cyclohexane-1,1'(2'H)-naphthalene]-4-carbamate[I(a)],
2. propyl 6'-ethoxyspiro[cyclohexane-1,1'(2'H)-naphthalene]-4-carbamate[I(a)], and the like.

EXAMPLE 24A

3',4'-Dihydrospiro[cyclohexane-1,1'(2'H)-naphthalen]-4-yl-N-methylamine hydrochloride [I(a)]

To a suspension of 0.22 g. (0.0058 M) of lithium aluminum hydride in 10 ml. of tetrahydrofuran, a tetrahydrofuran solution of 1.3 g. (0.0045 M) of ethyl 3',4'-dihydrospiro[cyclohexane-1,1'(2'H)-naphthalene]-4-carbamate[I(a)] (prepared as in Example 23A) is added. The mixture is stirred to reflux for about 6 hours, at room temperature for about 18 hours, and then cooled in an ice bath. To this is added successively, 0.22 ml. of water, 0.22 ml. 15% aqueous sodium hydroxide solution and 0.66 ml. of water. The resulting inorganic gel is collected on a filter, rinsed with ether and the filtrates evaporated to dryness. The residue is dissolved in a small amount of ether and treated with an excess of 6.4 N hydrochloric acid in ether. The resulting precipitate is collected on a filter and recrystallized from methanol:ethyl acetate to give 0.81 g. (52.7% yield) of 3',4'-dihydrospiro[cyclohexane-1,1'(2'H)-naphthalen]- 4-yl-N-methylamine hydrochloride[I(a)], having a melting point of 285° to 286° C.

Anal. Calcd. for $C_{16}H_{24}ClN$: C, 72.29; H, 9.10; N, 5.25;

Found: C, 72.60; H, 9.16; N, 5.35.

Following the procedure of Example 24A but substituting another lower alkyl 3',4'-dihydrospiro[cyclohexane-1,1'(2'H)-naphthalene]-4-carbamate[I(a)] as starting material, such as
1. ethyl 5'-fluorospiro[cyclohexane-1,1'(2'H)-naphthalen]-4-carbamate[I(a)],
2. propyl 6'-propylspiro[cyclohexane-1,1'(2'H)-naphthalene]-4-carbamate[I(a)], and the like, yields, respectively,
1. 5'-fluorospiro[cyclohexane-1,1'(2'H)-naphthalen]-4-yl-N-methylamine hydrochloride[I(a)],
2. 6'-propylspiro[cyclohexane-1,1'(2'H)-naphthalen]-4-yl-N-methylamine hydrochloride[I(a)], and the like.

EXAMPLE 25A

4'-Fluoro-4-[3',4'-dihydrospiro[cyclohexane-1,1'(-2'H)-naphthalen]-4-yl-N-methylamino]-butyrophenone hydrochloride[I(a)]

A mixture of the free base prepared from 0.81 g. (0.00306 M) of 3',4'-dihydrospiro[cyclohexane-1,1'(-2'H)-naphthalen-4-yl-N-methylamine hydrochloride[I(a)] (obtained as in Example 24A), 0.63 g. of potassium iodide, 0.96 g. of potassium carbonate and 0.87 g. of the 2,2-dimethyl-1,3-propanediol ketal of 4-chloro-4'-fluorobutyrophenone in 15 ml. of dimethylformamide is heated together in an oil bath at about 90° C. for about 20 hours. The solvent is removed under vacuum and the residue dissolved in water and benzene. The organic layer is washed with water and brine and evaporated to dryness. A mixture of the residue, 6 ml. of 2.5 N hydrochloric acid and 12 ml. of methanol is stirred at room temperature for about 1.5 hours and most of the methanol removed under vacuum. The residual suspended solid is collected on a filter, washed with ether and recrystallized from methanol:ethyl acetate to give 0.59 g. (44.8% yield) of 4'-fluoro-4-[3',4'-dihydrospiro[cyclohexane-1,1'(2'H)-naphthalen]-4-yl-N-methylamino]-butyrophenone hydrochloride[I(a)], having a melting point of 204° to 205.5° C.

Anal. Calcd. for $C_{26}H_{33}ClFNO$: C, 72.62; H, 7.74; N, 3.26,

Found: C, 72.69; H, 7.93; N, 3.03.

Following the procedure of Example 25A but substituting another 3',4'-dihydrospiro[cyclohexane-1,1'(2'H)-naphthalen]-4-yl-N-lower alkylamine[I(a)] as starting material and the 2,2-dimethyl-1,3-propanediol ketal of another ω-haloalkyanaryl ketone, such as 1. 5'-chlorospiro[cyclohexane-1,1'(2'H)-naphthalen]-4-yl-N-methylamine[I(a)] and the 2,2-dimethyl-1,3-propane-diol of 4'-butoxy-4-chlorobutyrophenone,
2. 6'-ethoxyspiro[cyclohexane-1,1'(2'H)-naphthalen]-4-yl-N-ethylamine[I(a)] and the 2,2-dimethyl-1,3-propanediol ketal of 4-chloro-2'-methylbutyrophenone,
3. 7'-nitrospiro[cyclohexane-1,1'(2'H)-naphthalen]-4-yl-N-methylamine[I(a)] and the 2,2-dimethyl-1,3-propanediol ketal of 3-bromo-3'-chloropropiophenone,
4. 8'-acetylamidospiro[cyclohexane-1,1'(2'H)-naphthalen]-4-yl-N-ethylamine[I(a)] and the 2,2-dimethyl-1,3-propanediol ketal of 5-fluoro-4'-propylvalerophenone, and the like, yields, respectively, 1. 4'-butoxy-4-[5'-chloropsiro[cyclohexane-1,1'(2'H)-naphthalen]-4-yl-N-methylamino]butyrophenone hydrochloride [I(a)],
2. 2'-methyl-4-[6'-ethoxyspiro[cyclohexane-1,1'(2'H)-naphthalen]-4-yl-N-ethylamino]butyrophenone hydrochloride [I(a)],
3. 3'-chloro-3-[7'-nitrospiro[cyclohexane-1,1'(2'H)-naphthalen]-4-yl-N-methylamino]propiophenone hydrochloride [I(a)],
4. 4'-propyl-5-[8'-acetylamidospiro[cyclohexane-1,1'-(2'H)-naphthalen]-4-yl-N-ethylamino]-valerophenone hydrochloride[I(a)], and the like.

EXAMPLE 1B

Methyl-4-hydroxycyclohexane carboxylate[2]

A solution of 200 g. of methyl-p-hydroxybenzoate[1] (prepared as in Ann. 141, 247) in 1700 ml. of absolute ethanol has 66 g. of 5% rhodium/aluminum catalyst added thereto and then hydrogenated until no further uptake of hydrogen is observed. The catalyst is collected on a filter and the filtrate evaporated to dryness to yield 216 g. of crude methyl-4-hydroxycyclohexane carboxylate(2), as an oil.

EXAMPLE 2B

4-Carbomethoxy-1-cyclohexanone[3]

The methyl-4-hydroxycyclohexane carboxylate prepared in Example 1B is dissolved in acetone with mechanical stirring and cooled in an ice bath to about 5° C. Jones reagent is added at a rate to keep the reaction temperature below about 20° C. for about 10 minutes. Most of the solvent is removed on a rotary evaporator and the residue taken up in 500 ml. of ether and 150 ml. of water. The organic layer is separated, washed successively with water, saturated aqueous sodium bicarbonate solution, and brine and evaporated to dryness to yield an oil, which on distillation under vacuum gives 47.4 g. of 4-carbomethoxy-1-cyclohexanone[3] having a boiling point of 82° to 85° C. at 0.55 to 0.75 mm. of Hg.

EXAMPLE 3B

4-Carbomethoxy-1-cyclohexanone ethylene ketal[4]

A mixture of 189.7 g. of 4-carbomethoxy-1-cyclohexanone[3] (obtained as in Example 2B) in 2000 ml. of benzene, 67.5 ml. of ethylene glycol and 2.7 g. of p-toluenesulfonic acid is heated at reflux under a Dean-Stark trap for about 5 hours. After cooling, the solution is washed with saturated aqueous sodium bicarbonate and brine. The oily residue remaining when the organic solvent is evaporated to dryness is distilled under vacuum to give 231.8 g. of 4-carbomethoxy-1-cyclohexanone ethylene ketal[4] having a boiling point of 95° to 100° C. at 0.30 mm. of Hg.

EXAMPLE 4B

4-Benzyl-4-carbomethoxy-1-cyclohexanone ethylene ketal[5]

To a solution of 5 g. (0.05 M) of diisopropyl amine in 50 ml. of tetrahydrofuran cooled in ice:methanol, 32 ml. of 1.57 N butyl lithium in pentane is added over the course of about 5 minutes. There is then added, first, 10 g. (0.05 M) of 4-carbomethoxy-1-cyclohexanone ethylene ketal [4] (obtained as in Example 3B) in 50 ml. of tetrahydrufuran in the course of about 15 minutes, and then 8.5 g. (0.05 M) of α-bromotoluene (also named benzyl bromide) in 15 ml. of tetrahydrofuran in about 5 minutes. The clear solution is stirred at room temperature for about 1 hour, cooled in ice and treated with 50 ml. of saturated ammonium chloride solution. The organic layer is separated, diluted with benzene and washed successively with water, ice cold N hydrochloric acid solution, sodium bicarbonate solution and brine. The organic layer is evaporated to dryness and the oil that remains is distilled under vacuum to give 13.57 g. (93.5% of theoretical yield) of 4-benzyl-4-carbomethoxy-1-cyclohexanone ethylene ketal[5] as a viscous oil having a boiling point of 155° to 156° C. at 0.25 mm. of Hg.

Anal. Calcd. for $C_{17}H_{22}O_4$: C, 70.32; H, 7.64;

Found : C, 69.94; H, 7.60.

EXAMPLE 5B 4-(p-Methylbenzyl)-4-carbomethoxy-1-cyclohexanone ethylene ketal[5]

To a solution of 11.7 g. (0.112 M) of diisopropylamine in 115 ml. of tetrahydrofuran cooled in ice:methanol, 75 ml. of 1.67 N butyl lithium in pentane is added over the course of about 12 minutes. There is then added, first, 23.1 g. (0.112 M) of 4-carbomethoxy-1-cyclohexanone ethylene ketal[5] (obtained as in Example 3B) in 115 ml. of tetrahydrofuran in the course of about 15 minutes, and then 14 g. (0.112 M) of α-chloro-p-xylene in 115 ml. of tetrahydrofuran. The mixture is stirred in the cold for about 1 hour and at room temperature for about 2 hours, and then 100 ml. of saturated aqueous ammonium chloride solution and benzene added. The organic layer is separated, washed successively with water, 2.5 N hydrochloric acid solution, water and brine, and then evaporated to dryness. The residue is distilled under vacuum to give 21.47 g. (64% yield) of 4-(p-methylbenzyl)-4-carbomethoxy-1-cyclohexanone ethylene ketal[5] as a viscous oil having a boiling point of 166° to 168.5° C. at 0.3 mm. of Hg.

Anal. Calcd. for $C_{18}H_{24}O_2$: C, 71.02; H, 7.95; M.W. 304

Found: C, 71.23; H, 8.03; m/e 304.

EXAMPLE 6B 4-(m-Methylbenzyl)-4-carbomethoxy-1-cyclohexanone ethylene ketal[5]

To a solution of 10.1 g. (0.101 M) of diisopropylamine in 100 ml. of tetrahydrofuran cooled in ice:methanol, 62 ml. of 1.61 N butyl lithium in pentane is added. There is then added, first 20 g. (0.10 M) of 4-carbomethoxy-1-cyclohexanone ethylene ketal[4] (obtained as in Example 3B) in 100 ml. of tetrahydrofuran in the course of about 12 minutes, and then 18.5 g. of α-bromo-m-xylene in 100 ml. of tetrahydrofuran in about 12 minutes. The mixture is stirred in the cold for about 1 hour and at room temperature for about 1 hour, and then 100 ml. of saturated ammonium chloride solution and benzene added. The organic layer is separated, washed successively with water, 2.5 N hydrochloric acid solution, water, sodium bicarbonate solution and brine, and then evaporated to dryness. The residue is distilled under vacuum to give 21.32 g. (70% yield) of 4-(m-methylbenzyl)-4-carbomethoxy-1-cyclohexanone ethylene ketal[5] as a viscous oil having a boiling point of 160° to 163° C. at 0.4 mm. of Hg.

Anal. Calcd. for $C_{18}H_{24}O_4$: C, 71.02; H, 7.95; M.W. 304;

Found: C, 71.05; H, 8.12; m/e 304;

EXAMPLE 7B 4-(m-Methoxybenzyl)-4-carbomethoxy-1-cyclohexanone ethylene ketal[5]

To an ice cooled solution of 10.25 g. (0.102 M) of diisopropylamine in 100 ml. of tetrahydrofuran, 66 ml. of 1.67 N butyl lithium in pentane is added. There is then added, first, 19.6 g. (0.0995 M) of 4-carbomethoxy-1-cyclohexane ethylene ketal[4] (obtained as in Example 3B) in 100 ml. of tetrahydrofuran in the course of about 10 minutes, and then 15.3 g. of m-methoxylbenzyl chloride in 100 ml. of tetrahydrofuran in about 17 minutes. The mixture is stirred at room temperature for about 2 hours and treated with 100 ml. of saturated ammonium chloride solution and benzene. The organic layer is washed successively with water, 2.5 N hydrochloric acid, water and brine, and then evaporated to dryness. The residue is distilled under vacuum to give 22.32 g. (70% yield) of 4-(m-methoxybenzyl)-4-carbomethoxy-1-cyclohexanone ethylene ketal [5] having a boiling point of 159° to 165° C. at 0.2 mm. of Hg.

Anal. Calcd. for $C_{18}H_{24}O_2$: C, 67.48; H, 7.55

Found: C, 67.71; H, 7.81.

Following the procedures of Examples 4B through 7B but substituting other halides, such as 1. p-acetylamidobenzyl bromide,
2. m-chlorobenzyl bromide,
3. p-propylbenzyl bromide, and the like, yields, respectively, 1. 4-(p-acetylamidobenzyl)-4-carbomethoxy-1-cyclohexanone ethylene ketal [5],
2. 4-(m-chlorobenzyl)-4-carbomethoxy-1-cyclohexanone ethylene ketal [5],
3. 4-(p-propylbenzyl)-4-carbomethoxy-1-cyclohexanone ethylene ketal [5], and the like.

EXAMPLE 8B

1-Benzyl-4-cyclohexanone-1-carboxylic acid [7]

1. A mixture of 16.64 g. (0.057 M) of 4-benzyl-4-carbomethoxy-1-cyclohexane ethylene ketal[5] (prepared as in Example 4B) and 2.5 g. of postassium hydroxide in 100 ml. ethylene glycol is stirred at reflux for about 16 hours. The mixture is then allowed to cool and diluted with water. The solution is washed once with water and then made strongly acid with concentrated hydrochloric acid. The precipitated gum is extracted with ether and this solution washed first with water, then brine, and evaporated to dryness to give 4-benzyl-4-carboxy-1-cyclohexanone ethylene ketal [6].

2. A solution of the residue [6] and 13 ml. of 2.5 N hydrochloric acid in 130 ml. of acetone is stirred at room temperature for about 20 hours, most of the solvent removed under vacuum and the residue dissolved in ether. The organic layer is washed with water and brine and evaporated to dryness. The residual gum is chromatographed on a column of 800 ml. of acid washed silica gel with elution by 4% acetic acid in methylene chloride. The crystalline fractions are combined and recrystallized twice from methylene chloride:cyclohexane to give 5.62 g. (42% yield) of 1-benzyl-4-cyclohexanone-1-carboxylic acid[7] having a melting point of 120° to 123° C.

Anal. Calcd. for $C_{14}H_{16}O_2$: C, 72.39; H, 6.94

Found: C, 72.24; H, 6.86

EXAMPLE 9B 1-(p-Methylbenzyl)-4-cyclohexanone-1-carboxylic acid [7]

1. A mixture of 21.47 g. (0.0706 M) of 4-(p-methylbenzyl)-4-carbomethoxy-1-cyclohexanone ethylene ketal [5] (prepared in Example 5B) and 2.5 g. of potassium hydroxide in 100 ml. of ethylene glycol is stirred at reflux for about 16 hours. The mixture is then allowed to cool and diluted with water. The solution is washed once with water and then made strongly acidic with concentrated hydrochloric acid. The precipitated gum is extracted with ether and this solution washed with brine and evaporated to dryness to give 4-(p-methylbenzyl)-4-carboxy-1-cyclohexanone ethylene ketal[6].

2. A solution of the residue[6] and 25 ml. of 2.5 N hydrochloric acid in 200 ml. of acetone is stirred at room temperature for about 24 hours, most of the solvent removed under vacuum and the residue dissolved in ether. The organic layer is washed with brine and evaporated to dryness. The residue is chromatographed on a column of 1,500 ml. of silica gel with elution by 3% acetic acid in methylene chloride. The crystalline fractions are combined to give 6.8 g. (39% yield) of 1-(p-methoxybenzyl)-4-cyclohexanone-1-carboxylic acid[7] as a waxy solid. A small sample is recrystallized from ether: petroleum ether to give crystals[7] having a melting point of 120° to 123° C.

Anal. Calcd. for $C_{15}H_{18}O_3$: C, 73.14; H, 7.37

Found: C, 73.20; H, 7.60

EXAMPLE 10B 1-(m-Methylbenzyl)-4-cyclohexanone-1-carboxylic acid[7]

1. A solution of 21.31 g. (0.0701 M) of 4-(m-methylbenzyl)-4-carbomethoxy-1-cyclohexanone ethylene ketal[5] (prepared in Example 6B) and 3.4 g. of potassium hydroxide in 140 ml. of ethylene glycol is heated at reflux for about 20 hours. The mixture is then allowed to cool, diluted with water and extracted with ether. The aqueous layer is then made strongly acidic and the precipitated gum extracted with ether. This extract is washed with water and brine and evaporated to dryness to yield 4-(m-methylbenzyl)-4-carboxy-1-cyclohexanone ethylene ketal[6].

2. A solution of the residue[6] and 25 ml. of 2.5 N hydrochloric acid in 200 ml. of acetone is stirred at room temperature for about 16 hours, the solvent removed under vacuum and the residue extracted with ether. The extract is washed with water and brine and evaporated to dryness. The residue is chromatographed on 2000 ml. of acid washed silica gel with elution by 4% acetic acid in methylene chloride. The fractions found similar by thin layer chromatography are combined to give 14.8 g. (56% yield) of 1-(m-methylbenzyl)-4-cyclohexanone-1-carboxylic acid[7] as a waxy solid.

EXAMPLE 11B 1-(m-Methoxybenzyl)-4-cyclohexanone-1-carboxylic acid[7]

1. A mixture of 24.3 g. (0.076 M) of 4-(m-methoxybenzyl)-4-carbomethoxy-1-cyclohexanone ethylene ketal[5] (prepared as in Example 7B) and 4.35 g. of sodium hydroxide in 155 ml. of ethylene glycol is heated at reflux for about 42 hours. The mixture is then diluted with water and washed with ether. The organic layer is made acidic with hydrochloric acid the precipitated gum dissolved in ether. The ether solution is washed with brine and evaporated to dryness to give 4-(m-methoxybenzyl)-4-carboxy-1-cyclohexanone ethylene ketal[6].

2. A solution of the residue and 27 ml. of 2.5 N hydrochloric acid in 220 ml. of acetone is allowed to stand at room temperature for about 18 hours, then most of the solvent removed under vacuum and the residue dissolved in ether. The organic layer is washed with brine and evaporated to dryness. The residue is chromatographed on a column of acid washed silica gel with elution first by 0.5% acetic acid:methylene chloride then 2% acetic acid:methylene chloride. Those fractions found similar by thin layer chromatography are combined, the solvent evaporated and the resulting solid recrystallized twice from ether: Skellysolve B to give 7.18 g. (36% of theoretical yield) of 1-(m-methoxy-benzyl)-4-cyclohexanone-1-carboxylic acid[7] having a melting point of 109 to 112.5° C. An additional 3.82 g. (19% yield) of product [7] melting at 109° to 111° C. is obtained from the mother liquor.

Anal. Calcd. for $C_{15}H_{18}O_4$: C, 68.68; H, 6.92
Found: C, 68.30; H, 6.92.

Following the procedures of Example 8B through 11B but substituting other 4-benzyl-4-carbomethoxy-1-cyclohexanone ethylene ketals[5] as starting materials, such as 1. 4-(o-methylbenzyl)-4-carbomethoxy-1-cyclohexanone ethylene ketal[5], yields, 1. 1-(o-methylbenzyl)-4-cyclohexanone-1-carboxylic acid[7].

EXAMPLE 12B

Spiro(cyclohexane-1,2'-indan)-1',4-dione[8]

To 100 ml. of freshly distilled hydrogen fluoride, (14.63 M) of 1-benzyl-4-cyclohexanone-1-carboxylic acid[7] (prepared as in Example 8B) is added. The solution is allowed to stand at room temperature for about 18 hours and then poured cautiously into saturated aqueous sodium bicarbonate solution. The precipitated gum is extracted with benzene. The organic layer is washed successively with water, aqueous sodium bicarbonate solution and brine, and then evaporated to dryness. The residue is chromatographed on a column of 1,500 ml. of silica gel with elution by 20% acetone in Skellysolve B. There is first obtained a small amount of by-product followed by 10.5 g. (78%) of spiro(cyclohexane-1,2'-indan)-1',4-dione[8], having a melting point of 70.5° to 72° C.

Anal. Calcd. for $C_{14}H_{14}O_2$: C, 78.48; H, 6.59
Found: C, 78.43; H, 6.59.

The less polar by-product is recrystallized from petroleum ether to give 0.28 g. of a compound, which in view of its mass spectrum and elemental analysis is spiro(cyclohexane-1,2'-indan)-4,4-difluoro-1'-one.

EXAMPLE 13B

5'-Methylspiro(cyclohexane-1,2'-indan)-1',4-dione[8]

To 50 ml. of freshly distilled hydrogen fluoride, 6.8 g. (0.026 M) of 1-(p-methylbenzyl)-4-cyclohexanone-1-carboxylic acid [7] (prepared in Example 9B) is added. The solvent is allowed to evaporate over a period of about 3 days. The residue is dissolved in ether and this solution washed successively with water, aqueous sodium bicarbonate solution and brine. The solution is evaporated to dryness and the gum that remains is chromatographed on a column of 700 ml. of silica gel with elution by 20% acetone: Skellysolve B. The fractions found similar by thin layer chromatography are combined and rechromatographed on a column of 400 ml. of silica gel with elution by 20% acetone: Skellysolve B. The crystalline fractions are combined and recrystallized from acetone; Skellysolve B to give 2.06 g. (35% yield) of 5'-methylspiro(cyclohexane-1,2'-indan)-1',4-dione[8] having a melting point of 110° to 113° C.

Anal. Calcd. for $C_{15}H_{16}O_2$: C, 78.92; H, 7.06; M.W. 228.
Found: C, 78.92; H, 7.13; m/e 228.

EXAMPLE 14B

6'-Methylspiro(cyclohexane-1,2'-indan)-1',4-dione[8]

Onto 14.8 g. (0.060 M) of 1-(m-methylbenzyl)-4-cyclohexanone-1-carboxylic acid[7] (prepared in Example 10B), 100 ml. of hydrogen fluoride is distilled. Following about 2 days of standing at room temperature the solution is poured into saturated aqueous sodium bicarbonate solution. The precipitate is dissolved in ether and the organic washed successively with water, saturated aqueous sodium bicarbonate solution and brine and evaporated to dryness. The residue is chromatographed on a column of 1200 ml. of Florisil with elution by 10% acetone: Skellysolve B. The crystalline fractions are combined and recrystallized from acetone: Skellysolve B to give 7.3 g. (53% yield) of 6'-methylspiro(cyclohexane-1,2'-indan)-1',4-dione[8] having a melting point of 121° to 122.5° C.

Anal. Calcd. for $C_{15}H_{16}O_2$: C, 78.92; H, 7.01.
Found: C, 78.79; H, 7.22.

EXAMPLE 15B

5'-Methoxyspiro(cyclohexane-1,2'-indan)-1',4-dione[8]

A suspension of 15.63 g. (0.060 M) of 1-(m-methoxy-benzyl)-4-cyclohexanone-1-carboxylic acid [7] (prepared as in Example 11B) and 12.5 g. of phosphorus pentachloride in 190 ml. of monochlorobenzene is stirred mechanically under reflux for about 1.5 hours and at room temperature for about 1.5 hours. The mixture is then cooled in ice and treated with 6.85 ml. of stannic chloride. After about 0.5 hours of stirring in the cold and about 18 hours at room temperature, 96 ml. of 2.5 N hydrochloric acid is added in the course of about ten minutes. After about an additional hour of stirring, the organic layer is separated, washed successively with water, aqueous sodium bicarbonate solution and brine and evaporated to dryness. The residue is chromatographed on a column of 1200 ml. of silica gel with elution by 10% ethyl acetate in methylene chloride. The crystalline fractions are combined to give 7.51 g. (51% yield) of 5'-methoxyspiro[cyclohexane-1,2'-indan]-1',4-dione [8] having a melting point of 105° to 107° C., and an analytic sample melting at 110° to 112° C.

Anal. Calcd. for $C_{15}H_{16}O_3$: C, 73.75; H, 6.60; M.W. 244.

Found: C, 73.75; H, 6.65; m/e 244.

Following the procedures of Examples 12B through 15B but substituting other 1-benzyl-4-cyclohexanone-1-carboxylic acids [7] as starting materials, such as
1-(p-ethylbenzyl)-4-cyclohexanone-1-carboxylic acid-[7], and the like, yields,
5'-ethylspiro(cyclohexane-1,2'-indan)-1',4-dione[8], and the like.

EXAMPLE 16B

Spiro(cyclohexane-1,2'-indan)-1',4-dione 4-ethylene ketal[9]

A mixture of 1.77 g. (0.0083 M) of spiro(cyclohexane-1,2'-indan)-1',4-dione[8] (prepared as in Example 12B) 0.51 g. (0.46 ml; 0.0082 M) of ethylene glycol and 0.1 g. of p-toluenesulfonic acid in 50 ml. of benzene is heated at reflux under a Dean-Stark trap for about 4 hours. The mixture is allowed to cool, washed successively with aqueous sodium bicarbonate solution, water and brine and evaporated to dryness. The residual solid is recrystallized from cyclohexane to give 1.67 g. (75% yield) of spiro(cyclohexane-1,2'-indan)-1',4-dione 4-ethylene ketal[9], having a melting point of 158° to 160.5° C; $\nu_{max}$. 1690 $cm^{-1}$.

Anal. Calcd. for $C_{16}H_{18}O_3$: C, 74.39; H, 7.02; M.W. 258.

Found: C, 73.99; H, 6.98; m/e 258.

EXAMPLE 17B

5'-Methylspiro(cyclohexane-1,2'-indan)-1',4-dione 4-ethylene ketal [9]

A mixture of 2.06 g. (0.00905 M) of 5'-methylspiro(-cyclohexane-1,2'-indan)-1',4-dione [8] (prepared in Example 13B), 0.56 g. (0.50 ml.) of ethylene glycol and 0.1 g. of p-toluenesulfonic acid in 50 ml. of benzene is heated at reflux under a Dean-Stark trap for about 2 hours. The mixture is allowed to cool, washed with aqueous sodium bicarbonate solution then water and evaporated to dryness. The residual solid is recrystallized from methylene chloride: cyclohexane to give 1.96 g. (86%) of 5'-methyl-spiro(cyclohexane-1,2'-indan)-1',4-dione 4-ethylene ketal-[9], melting at 124° to 127° C.

Anal. Calcd. for $C_{17}H_{20}O_3$: C, 74.97; H, 7.40.
Found: C, 74.97; H, 7.51.

EXAMPLE 18B

6'-Methylspiro(cyclohexane-1,2'-indan)-1',4-dione 4-ethylene ketal [9]

A mixture of 7.3 g. (0.032 M) of 6'-methylspiro(cyclohexane-1,2'-indan)-1',4-dione [8] (prepared in Example 14B), 2.15 g. (1.95 ml.) of ethylene glycol and 0.5 g. of p-toluenesulfonic acid in 200 ml. of benzene is heated at reflux under a Dean-Stark trap for about 5 hours. The mixture is allowed to cool, washed successively with aqueous sodium bicarbonate solution, water and brine and evaporated to dryness. The residual solid is recrystallized from methylene chloride: Skellysolve B to give 7.94 g. (91% yield) of 6'-methylspiro(cyclohexane-1,2'-indan)-1',4-dione 4-ethylene ketal [9] melting at 116° to 118° C.

Anal. Calcd. for $C_{17}H_{20}O_3$: C, 74.97; H, 7.40.
Found: C, 75.33; H, 7.65.

EXAMPLE 19B

5'-Methoxyspiro(cyclohexane-1,2'-indan)-1', 4-dione 4-ethylene ketal [9]

A mixture of 4.89 g. (0.0196 M) of 6'-methoxyspiro(cyclohexane-1,2'-indan)-1',4-dione [8] (prepared as in Example 15B), 1.21 g. of ethylene glycol and 0.2 g. of p-toluenesulfonic acid in 100 ml. of benzene is heated at reflux under a Dean-Stark trap for about 5 hours. The mixture is allowed to cool, washed with aqueous sodium bicarbonate solution and evaporated to dryness. The residue is recrystallized twice from methylene chloride: Skellysolve B to give 4.13 g. (73% yield) of 5'-methoxyspiro(cyclohexane-1,2'-indan)-1',4-dione 4-ethylene ketal [9] having a melting point of 142° to 144° C.

Anal. Calcd. for $C_{17}H_{20}O_4$: C, 70.81; H, 6.99.
Found: C, 71.06; H, 7.19.

Following the procedures of Examples 16B through 19B but substituting other spiro(cyclohexane-1,2'-indan)-1',4-diones [8] as starting materials, such as
1. 7'-acetylamidospiro(cyclohexane-1,2'-indan)-1',4-dione[8],
2. 5'-ethoxyspiro(cyclohexane-1,2'-indan)1', 4-dione [8], and the like,
yields, respectively,
1. 7'-acetylamidospiro(cyclohexane-1,2'-indan)- 1', 4-dione 4-ethylene ketal [9],
2. 5'-ethoxyspiro(cyclohexane-1,2'-indan)-1'4-dione 4-ethylene ketal [9], and the like.

EXAMPLE 20B

Spiro(cyclohexane-1,2'-indan)-4-one ethylene ketal [10]

A mixture of 5g. (0.0194 M) of spiro(cyclohexane 1,2'-indan)-1',4-dione 4-ethylene ketal [9] (prepared as in Example 16B), 2.6ml. of hydrazine hydrate and 3.76 g. of potassium hydroxide in 50 ml. of ethylene glycol is heated at reflux for about 1.5 hours. Material is then removed by distillation to bring the pot temperature to 200° C. After about 5 hours of additional heating at reflux, the mixture is allowed to cool and diluted with water. The precipitated solid is collected on a filter, dried and recrystallized from petroleum ether to give 4 g. (85% yield) of spiro(cyclohexane-1,2'-indan)-4-one ethylene ketal [10], having a melting point of 70° to 74° C.

Anal. Calcd. for $C_{16}H_{20}O_2$: C, 78.65; H, 8.25.
Found: C, 78.39; H, 8.19.

EXAMPLE 21B

5'-Methylspiro(cyclohexane-1,2'-indan)-4-one ethylene ketal [10]

A mixture of 7.3 g. (0.027 M) of 5'-methylspiro-(cyclohexane-1,2'-indan)-1', 4-dione 4-ethylene ketal [9] (prepared as in Example 17B), 3.8 ml. of hydrazine hydrate and 5.52 g. of potassium hydroxide in 70 ml. of ethylene glycol is heated at reflux for about 1 hour. Material is then removed by distillation to bring the pot temperature to 200° C. Following about 18 hours of heating at reflux the mixture is allowed to cool and poured into water and extracted with ether. The organic extract is washed with water and brine and evaporated to dryness, to give 5'-methylspiro(cyclohexane-1,2'-indan)-4-one ethylene ketal [10].

EXAMPLE 22B

6'-Methylspiro(cyclohexane-1,2'-indan)-4-one ethylene ketal [10]

A mixture of 7.3 g. (0.027 M) of 6'-methylspirocyclohexane-1,2'-indan)-1', 4-dione 4-ethylene ketal [9] (prepared as in Example 18B), 3.8 ml. of hydrazine hydrate and 5.52 g. of potassium hydroxide in 70 ml. of ethylene glycol is heated at reflux for about 1 hour. Material is then removed by distillation to bring the pot temperature to 200° C. Following about 18 hours of heating at reflux the mixture is allowed to cool and poured into water. The precipitated oil is extracted with ether. This organic extract is washed with water and brine and evaporated to dryness, to give 7.01 g. (about 99% yield) of 6'-methylspiro(cyclohexane-1,2'-indan)-4-one ethylene ketal [10] having a melting point of 37+ to 41° C. This material, having a nuclear magnetic resonance (NMR) spectrum in agreement with the expected structure, is not satisfactorily recrystallized.

EXAMPLE 23B

5'-Methoxyspiro(cyclohexane-1',2-indan)-4-one ethylene ketal [10]

A mixture of 4.57 g. (0.0158 M) of 5'-methoxyspiro-(cyclohexane-1,2'-indan)-1',4 -dione 4-ethylene ketal [9] (prepared as in Example 19B), 2.45 g. of hydrazine hydrate and 3.15 g. of potassium hydroxide in 40 ml. of ethylene glycol is heated at reflux for about 1 hour. Solvent is removed by distillation to bring the reaction mixture to 200° C. Following about 1.5 hours at this temperature the mixture is poured into water and well extracted with ether. The ether extracts are combined and evaporated to dryness. The residue is chromatographed on a 250 ml. column of silica gel with elution by 10% acetone in Skellysolve B to give 2.07 g. (48% yield) of 5'-methoxyspiro(cyclohexane-1',2-indan)-4-one ethylene ketal [10] having a melting point of 59° to 61° C. The analytical sample from an earlier experiment melted at 65° to 66.5° C.

Anal. Calcd. for $C_{17}H_{22}O_3$: C, 74.22; H, 8.08.

Found: C, 74.57; H, 8.24.

The aqueous portion (i.e., not extracted by ether), above, is "acidified" with solid carbon dioxide. The precipitated solid is collected on a filter and recrystallized from methanol to give 0.51 g. of by-product, 5''-hydroxydispiro [1,3-dioxolane-2,1'-cyclohexane-4', 2''-indan]-1''-one hydrazone, having melting ranges of 243° to 246° C. and 285° to 290° C.

Anal. Calcd. for $C_{16}H_{20}N_2O_3$: C, 66.69; H, 6.99; N, 9.71; M.W. 288.

Found: C, 66.16; H, 7.14; N, 9.96; m/e 288.

Following the procedures of Example 20B through 23B but substituting other spiro(cyclohexane-1,2'-indan)-1', 4-dione 4-ethylene ketals [9] as starting materials, such as 5'-chlorospiro(cyclohexane-1,2'-indan)-1',4-dione 4-ethylene ketal [9], and the like, yields, 5'-chlorospiro(cyclohexane-1,2'-indan)-4-one ethylene ketal [10], and the like.

Example 24B

Spiro(cyclohexane-1,2'-indan)-4-one, oxime [12]

1. A mixture of 4g. (0.016 M) of spiro(cyclohexane-1,2'-indan)-4-one ethylene ketal [10] (prepared in Example 20B) and 8 ml. of 2.5 N hydrochoric acid in 80 ml. of acetone is heated at reflux for about 4 hours. Most of the solvent is removed under vacuum and ether added. The organic layer is separated, washed with water and brine and evaporated to dryness. The residue is chromatographed on a 350 ml. column of silica gel with elution by methylene chloride. Those fractions similar by thin layer chromatography are combined to give spiro(cyclohexane-1,2'-indan)-4-one [11] as an amorphous gum.

2. A mixture of the gum [11] obtained in (1), above, 3 g. of hydroxylamine hydrochloride and 10 ml. of water in 100 ml. of tetrahydrofuran is heated at reflux for about 15 hours. Most of the solvent is removed under vacuum and the residue diluted with water. The precipitated solid is recrystallized from cyclohexanone to give 3.1 g. (90% yield) of spiro(cyclohexane-1,2'-indan)-4-one oxime [12] having a melting point of 120° to 122° C.

Anal. Calcd. for $C_{14}H_{17}NO$: C, 78.10; H, 7.96; N, 6.51.

Found: C, 78.08; H, 7.85; N, 6.50.

Following the procedure of Example 24B but substituting other spiro(cyclohexane-1,2'-indan)-4-one ethylene ketals [10] as starting materials, such as 1. 7'-bromospiro(cyclohexane-1,2'-indan)-4-one, ethylene ketal [10],
2. 6'-ethylspiro(cyclohexane-1,2'-indan)-4-one, ethylene ketal [10],
3. 5'-methoxyspiro(cyclohexane-1,2'-indan)-4-one, ethylene ketal [10], and the like, yields, respectively, 1. 7'-bromospiro(cyclohexane-1,2'-indan)-4-one [11] and its oxime [12],
2. 6'-ethylspiro(cyclohexane-1,2'-indan)-4-one [11] and its oxime [12],
3. 5'-methoxyspiro(cyclohexane-1,2'-indan)-4-one- [11] and its oxime [12], and the like.

EXAMPLE 25B

Spiro(cyclohexane-1,2'-indan)-4-one, oxime acetate [13]

A solution of 3.1 g. spiro(cyclohexane-1,2'-indan)-4-one oxime [12] (prepared in Example 24B) and 6 ml. of acetic anhydride in 25 ml. of pyridine is allowed to stand at room temperature for about 6 hours. The reaction mixture is then poured into ice: water and the solid collected on a filter. The solid is recrystallized from Skellysolve B to give 2.94 g. (88% yield) of spiro(cyclohexane-1,2'-indan)-4-one, oxime acetate [13] having a melting point of 91° to 94° C.

Anal. Calcd. for $C_{16}H_{19}NO_2$: C, 74.68; H, 7.44; N, 5.44.

Found: C, 74.43; H, 7.35; N, 5.49.

Following the procedure of Example 25B but substituting other spiro(cyclohexane-1,2'-indan)-4-one oximes [12] as starting materials, such as
1. 6'-chlorospiro(cyclohexane-1,2'-indan)-4-one, oxime [12],
2. 7'-ethoxyspiro(cyclohexane-1,2'-indan)-4-one, oxime [12], and the like,
yields, respectively,
1. 6'-chlorospiro(cyclohexane-1,2'-indan)-4-one, oxime acetate [13],
2. 7'-ethoxyspiro(cyclohexane-1,2'-indan)-4-one, oxime acetate [13], and the like.

EXAMPLE 26B

Sprio(cyclohexane-1,2'-indan)-4-amine hydrochloride-[I (b)]

To an ice-cooled solution of 2.94 g. (0.0114 M) of spiro(cyclohexane-1,2'-indan)-4-one oxime acetate [13] (prepared in Example 25B) in 50ml. of tetrahydrofuran, 15 ml. of N diborane in tetrahydrofuran is added dropwise. Following about 6 hours of standing in the cold, 1 ml. of water is added. The solvent is then removed under vacuum and the residue stirred for about 1 hour at room temperature with 90 ml. of 2.5 N hydrochloric acid covered by ether. The aqueous layer is then made strongly basic, the organic layer washed with water and brine and evaporated to dryness. The residue is dissolved in ether and this solution treated with 5 N hydrochloric acid in ether. The resulting precipitate is recrystallized from methanol: ethyl acetate to give 1.12 g. (41% yield) of spiro(cyclohexane-1,2'-indan)-4-amine hydrochloride [I (b)], having a melting point of 270° to 273° C.

Anal. Calcd. for $C_{14}H_{20}$ ClN: C, 70.71; H, 8.48; N, 5.89.

Found: C, 70.68; H, 8.55; N, 5.69.

Following the procedure of Example 26B but substituting other spiro(cyclohexane-1,2'-indan)-4-one acetate oximes [13] as starting materials, such as
1. 5'-bromospiro(cyclohexane-1,2'-indan)-4-one, oxime acetate [13],
2. 6'-ethylspiro(cyclohexane-1,2'-indan)-4-one, oxime acetate [13],
3. 7'-methoxyspiro(cyclohexane-1,2'-indan)-4-one, oxime acetate [13], and the like,
yields, respectively,
1. 5'-bromospiro(cyclohexane-1,2'-indan)-4-amine [I (b)],
2. 6'-ethylspiro(cyclohexane-1,2'-indan)-4-amine [I (b)],
3. 7'-methoxyspiro(cyclohexane-1,2'-indan)-4-amine [I (b)], and the like.

EXAMPLE 27B

Spiro(cyclohexane-1,2'-indan)-4-ol [14]

To a solution of 8.33 g. (0.042 M) of crude spiro(cyclohexane-1,2'-indan)-4-one[11] [obtained as in (1) of Example 23B] in 85 ml. of ethanol, 1.6 g. of sodium borohydride is added. Following about 6 hours of stirring at room temperature, most of the solvent is removed under vacuum. The residue is suspended in ether and water. The organic layer is washed with water and brine and evaporated to dryness. The residue is chromatographed on a column of 800 ml. of silica gel with elution by 10% acetone in methylene chloride. The crystalline fractions are combined and recrystallized from petroleum ether to give 5.52 g. (66% yield) of spiro(cyclohexane-1,2'-indan)-4-ol [14] having a melting point of 76° to 78° C.

Anal. Calcd. for $C_{14}H_{18}O$: C, 83.12; H, 8.97.

Found: C, 83.33; H, 8.92.

Following the procedure of Example 27B but substituting other spiro(cyclohexane-1,2'-indan)-4-ones [11] as starting materials, such as
1. 5'-chlorospiro(cyclohexane-1,2'-indan)-4-one [11],
2. 6'-ethoxyspiro(cyclohexane-1,2'-indan)-4-one [11], and the like,
yields, respectively,
1. 5'-chlorospiro(cyclohexane-1,2'-indan)-4-ol [14],
2. 6'-ethoxyspiro(cyclohexane-1,2'-indan)-4-ol [14], and the like.

EXAMPLE 28B

5'-Methylspiro(cyclohexane-1,2'-indan)-4-ol [14]

1. A solution of 7.01 g. (0.027 M) of 5'-methylspiro(cyclohexane-1,2'-indan)-4-one ethylene ketal [10] (obtained as in Example 21B) and 10 ml. of 2.5 N hydrochloric acid in 100 ml. of acetone is allowed to stand at room temperature for about 17 hours. The solvent is then removed under vacuum and the residue suspended in water and ether. The organic layer is washed with water and brine and evaporated to dryness. The residue is chromatographed on a column of silica gel with elution by 10% acetone: Skellysolve B. The crystalline fractions are combined and recrystallized from petroleum ether to give 4.43 g. (76% yield) of 5'-methyl(cyclohexane-1,2'-indan)-4-one [11], melting at 68° to 70° C.

Anal. Calcd. for $C_{15}H_{18}O$: C, 84.07; H, 8.47.

Found: C, 83.92; H, 8.79.

2. To a solution of 4.43 g. of the 5'-methylspiro(cyclohexane-1,2'-indan)-4-one [11] obtained in (1), above, in 100 ml. of 95% isopropanol, 0.8 g. of sodium borohydride is added. Following about 5.5 hours of standing at room temperature most of the solvent is removed under vacuum. The residue is dissolved in water and ether. The organic layer is washed with water and brine and then evaporated to dryness, to give 4.55 g. (97%) of 5'-methylspiro(cyclohexane-1,2'-indan)-4-ol[14] as a gum which showed a single spot on thin layer chromatography.

EXAMPLE 29B

5'-Methoxyspiro(cyclohexane-1,2'-indan)-4-ol[14]

1. A solution of 2.87 g. (0.0105 M) of 5'-methoxyspiro(cyclohexane-1,2'-indan)-4-one ethylene ketal[10] (obtained as in Example 23B) and 6.5 ml. of 2.5 N hydrochloric acid in 60 ml. of acetone is allowed to stand at room temperature for about 18 hours. Most of the solvent is removed under vacuum and the residue dissolved in water and ether. The organic layer is washed with water and brine and evaporated to dryness. The residue is recrystallized from Skellysolve B to give 1.95 g. (81% yield) of 5'-methoxyspiro(cyclohexane-1,2'-indan)-4-one[11] melting at 89° to 91° C.

Anal. Calcd. for $C_{15}H_{18}O_2$: C, 78.23; H, 7.88.

Found: C, 77.96; H, 7.96.

2. A suspension of 1.95 g. of the 5'-methoxyspiro(cyclohexane-1,2'-indan)-4-one[11] obtained in (1), above, in 100 ml. of isopropanol is warmed to bring the solid into solution. There is then added 0.35 g. of sodium borohydride and the mixture stirred at room temperature for about 7 hours. Most of the solvent is removed under vacuum and the residue dissolved in water and ether. The residue is washed with water and brine and evaporated to dryness. The product, 1.86 g. of 5'-methoxyspiro(cyclohexane-1,2'-indan)-4-ol[14], is an oil having a nuclear magnetic resonance (NMR) spectrum in agreement with the expected structure.

Following the procedures of Examples 28B and 29B but substituting other spiro(cyclohexane-1,2'-indan)-4-one ethylene ketals[10] as starting materials, such as 7'-fluorospiro(cyclohexane-1,2'-indan)-4-one ethylene ketal[10], and the like, yields,
7'-fluorospiro(cyclohexane-1,2'-indan)-4-ol[14], and the like.

EXAMPLE 30B

Spiro(cyclohexane-1,2'-indan)-4-ol methanesulfonate[15]

A mixture of 5.52 g. (0.027 M) of spiro(cyclohexane-1,2'-indan)-4-ol[14] (obtained in Example 27B) in 50 ml. of ice cold pyridine is treated with 5.5 ml. of methane sulfonyl chloride. After standing for about 7 hours in the cold the mixture is diluted with ice: water. The precipitated solid is recrystallized from acetone: Skellysolve B to give 7.15 g. (93% yield) of spiro(cyclohexane-1,2'-indan)-4-ol methanesulfonate[15], melting at 100° to 102° C.

Anal. Calcd. for $C_{15}H_{20}O_3S$: C, 64.25; H, 7.19.
Found; C, 63.87; H, 7.50.

EXAMPLE 31B

5'-Methylspiro(cyclohexane-1,2'-indan)-4-ol methanesulfonate[15]

To an ice cold solution of 4.55 g. (0.021 M) of 5'-methylspiro(cyclohexane-1,2'-indan)-4-ol[14] (obtained in Example 28B) in 40 ml. of pyridine, 4.5 ml. of methanesulfonyl chloride is added. After standing about 5 hours in the cold the mixture is poured into ice: water. The precipitated gum is extracted with ether and the extract washed successively with water, 2.5 N hydrochloric acid, water and brine. The extract is evaporated to dryness and the solid that remains is recrystallized from ether: petroleum ether to give 5.38 g. (83%) of 5'-methylspiro(cyclohexane)-1,2'-indan)-4-ol methanesulfonate[15], melting at 64° to 66° C.

Anal. Calcd. for $C_{16}H_{22}O_3S$: C, 65.27; H, 7.53.
Found: C, 65.41; H, 7.69.

EXAMPLE 32B

5'-Methoxyspiro(cyclohexane-1,2'-indan)-4-ol methanesulfonate[15 ]

An ice cold solution of 1.86 g. (0.008 M) of 5'-methoxyspiro(cyclohexane-1,2'-indan)-4-ol[14] (obtained in Example 29B) in 18 ml. of pyridine is treated with 2 ml. of methane sulfonyl chloride. After standing for about 5 hours in the cold the mixture is poured onto ice: water. The precipitated solid is recrystallized from methylene chloride: Skellysolve B to give 2.1 g. (85% yield) of 5'-methoxyspiro(cyclohexane-1,2'-indan)-4-ol methanesulfonate[15], melting at 63° to 67° C.

Anal. Calcd. for $C_{16}H_{22}O_4S$: C, 61.91; H, 7.14.
Found: C, 61.80; H, 7.14.

Following the procedures of Example 30B through 32B but substituting other spiro(cyclohexane-1,2'-indan)-4-ols[14] as starting materials, such as
1. 5'-bromospiro(cyclohexane-1,2'-indan)-4-ol[14],
2. 6'-ethylspiro(cyclohexane-1,2'-indan)-4-ol[14],
3. 7'-isopropoxyspiro(cyclohexane-1,2'-indan)-4-ol[14], and the like,
yields, respectively, 1. 5'bromospiro(cyclohexane-1,2'-indan)-4-ol methanesulfonate[15],
2. 6'-ethylspiro(cyclohexane-1,2'-indan)-4-ol methanesulfonate [15],
3. 7'-isopropoxyspiro(cyclohexane-1,2'-indan)-4-ol methanesulfonate[15], and the like.

EXAMPLE 33B

Spiro(cyclohexane-1,2'-indan)-4-amine hydrochloride I(b)]

1. A mixture of 7.15 g. (0.0256 M) of spiro(cyclohexane-1,2'-indan)-4-ol methanesulfonate[15] (obtained in Example 30B) and 7 g. of sodium azide in 70 ml. of dimethylformamide is stirred in an oil bath at about 90° C. for about 17 hours. The solvent is then removed under vacuum and the residue dissolved in benzene and water. The organic layer is washed with water and brine to give spiro(cyclohexane-1,2'-indan)-4-ylazide[16].

2. A solution of the crude spiro(cyclohexane-1,2'-indan)-4ylazide[16] obtained in (1), above, in 75 ml. of tetrahydrofuran is added to a well stirred suspension of 1 g. of lithium aluminum hydride in 25 ml. of tetrahydrofuran. Following about 5 hours of stirring at room temperature the mixture is cooled in ice and treated successively with 1 ml. of water, 1 ml. of 15% aqueous sodium hydroxide solution and 3 ml. of water. The inorganic gel is removed by filtration and the filtrate evaporated to dryness. The residue is dissolved in ether and this solution treated with 5 N hydrogen chloride in ether. The precipitated solid is recrystallized from methanol: ethyl acetate to give 4.58 g. (76% yield) of spiro(cyclohexane-1,2'-indan)-4-amine hydrochloride[I(b)], melting at 280° to 282° C.

EXAMPLE 34B

5'-Methylspiro(cyclohexane-1,2'-indan)-4-amine hydrochloride[I(b)]

1. A mixture of 5.38 g. (0.0183 M) of 5'-methylspiro(cyclohexane-1,2'-indan)-4-ol methanesulfonate[15] (prepared in Example 31B) and 5.4 g. of sodium azide in 55 ml. of dimethylformamide is stirred in an oil bath at about 100° C. for about 18 hours. The solvent is removed under vacuum and the residue dissolved in benzene and water. The organic layer is washed with water and brine and evaporated to dryness to give 5'-methylspiro(cyclohexane-1,2'-indan)-4-ylazide[16].

2. A solution of the 5'-methylspiro(cyclohexane-1,2'-indan)-4-ylazide[16] obtained in (1), above, in 60 ml. of tetrahydrofuran is added to a well stirred suspension of 0.75 g. of lithium aluminum hydride in 20 ml. of tetrahydrofuran in the course of about 30 minutes. After about 4 hours the mixture is cooled in ice and treated successively with 0.75 ml. water, 0.75 ml. of 15% aqueous sodium hydroxide solution and 2.25 ml. of water. The inorganic gel is removed by filtration, rinsed with methylene chloride and ether and the filtrate evaporated to dryness. The residue is dissolved in ether and the solution treated with 5 N hydrogen chloride in ether. The precipitated solid is recrystallized from methylene chloride: ethyl acetate to give 3.89 g. (85%) of 5'-methylspiro(cyclohexane-1,2'-indan)-4-amine hydrochloride[I(b)], melting at 248° to 252° C.

Anal. Calcd. for $C_{15}H_{22}ClN$: C, 71.54; H, 8.81; N, 5.56.
Found: C, 71.19; H, 8.85; N, 5.42.

EXAMPLE 35B

5'-Methoxyspiro(cyclohexane-1,2'-indan)-4-amine hydrochloride[I(b)]

1. A mixture of 2.1 g. (0.0068 M) of 5'-methoxyspiro(cyclohexane-1,2'-indan)-4-ol methanesulfonate[15] (obtained in Example 32B) and 2.1 g. of sodium azide in 20 ml. of dimethylformamide is stirred in an oil bath at about 90° C. for about 16 hours. The solvent is removed under vacuum and the residue dissolved in benzene and water. The organic layer is washed with water and brine and evaporated to dryness to give 5'-methoxyspiro(cyclohexane-1,2'-indan)-4-ylazide[16].

2. A solution of the 5'-methoxyspiro(cyclohexane-1,2'-indan)-4-ylazide[16] obtained in (1), above, in 50 ml. of tetrahydrofuran to 0.26 g. of lithium aluminum hydride in 8 ml. of tetrahydrofuran in the course of about 10 minutes. Following about 4.5 hours of stirring at room temperature the mixture is cooled in ice and there is added successively 0.26 ml. of water, 0.26 ml. of 15% aqueous sodium hydroxide solution and 0.78 ml. of water. The inorganic gel is collected on a filter and the filtrate evaporated to dryness. A solution of the residue in ether is treated with 6 N hydrogen chloride in ether. The precipitated solid is recrystallized from methanol: methylene chloride: ethyl acetate to give 0.69 g. (38% yield) of 5'-methoxyspiro(cyclohexane-1,2'-indan)-4-amine hydrochloride[I(b)], having a melting point of 274° to 277° C.

Anal. Calcd. for $C_{15}H_{22}ClNO$: C, 67.27; H, 8.28; N, 5.23.

Found: C, 67.25; H, 8.18; N, 4.98.

Concentration of the mother liquors gives 0.43 g. (23%) of an apparently polymorphic form of the product [I(b)], having a melting point of 246° to 248° C.

Anal. Found: C, 66.98; H, 8.50; N, 4.87; m/e 231.

Following the procedures of Examples 33B through 35B but substituting other spiro(cyclohexane-1,2'-indan)-4-ol methanesulfonates[15] as starting materials, such as 1. 5'-fluorospiro(cyclohexane-1,2'-indan)-4-ol methanesulfonate[15],
2. 6'-isopropylspiro(cyclohexane-1,2'-indan)-4-ol methanesulfonate[15], and the like, yields, respectively, 1. 5'-fluorospiro(cyclohexane-1,2'-indan)-4-amine hydrochloride[I(b)],
2. 6'-isopropylspiro(cyclohexane-1,2'-indan)-4-amine hydrochloride[I(b)], and the like.

Following the procedures of the immediately preceding paragraph and of Examples 33B through 35B but substituting other pharmacologically acceptable acids for hydrogen chloride, e.g., sulfuric, nitric, acetic, citric, benzoic, nicotinic, and the like, yields corresponding spiro(cyclohexane-1,2'-indan)-4-amine acid addition salts[I(b)].

EXAMPLE 36B

1-Spiro(cyclohexane-1,2'-indan)-4-yl piperidine hydrochloride[I(b)]

To a suspension of 1.53 g. (0.0065 M) of spiro(cyclohexane-1,2'-indan)-4-amine hydroxhloride[I(b)] (prepared as in Example 33B) in 30 ml. of ethanol, there is added 1.58 ml. of 4.2 N sodium methoxide in methanol. Following about 1 hour of stirring, 1.62 g. of potassium carbonate and 0.97 ml. of 1,5-diiodopentane is added and the mixture heated to reflux. After about 18 hours the mixture is allowed to cool and most of the solvent removed under vacuum. The residue is partitioned between ether and water, the organic layer washed with water and brine and then evaporated to dryness. The residual solid is dissolved in ether and this solution treated with 5 N hydrogen chloride in ether. The resulting precipitate is recrystallized from methylene chloride: ethyl acetate to give 1.53 g. (77% of theoretical yield of 1-spiro(cyclohexane-1,2'-indan)-4-yl piperidine hydrochloride[I(b)], having a melting point of 282° to 286° C.

Anal. Calcd. for $C_{19}H_{28}ClN$: C, 74.60; H, 9.23; N, 4.58.

Found: C, 74.13; H, 9.27; N, 4.71.

Following the procedure of Example 36B but substituting the same and other (a) acid addition salts of spiro(cyclohexane-1,2'-indan)-4-amines[I(b)] and (b) the same and other dihaloalkanes in stoichiometrically appropriate amounts as starting materials, such as 1. spiro(cyclohexane-1,2'-indan)-4-amine hydrochloride [I(b)] and 1,4-dibromobutane,
2. spiro(cyclohexane-1,2'-indan)-4-amine hydrobromide [I(b)] and 1,6-diiodohexane,
3. 5'-chlorospiro(cyclohexane-1,2'-indan)-4-amine hydrochloride[I(b)] and 1,5-diiodopentane,
4. 6'-ethylspiro(cyclohexane-1,2'-indan)-4-amine nitrate[I(b)] and 1,4-diiodobutane, and the like, yields, respectively, 1. 1-spiro(cyclohexane-1,2'-indan)-4-yl pyrrolidine hydrochloride[I(b)],
2. 1-spiro(cyclohexane-1,2'-indan)-4-yl hexamethyleneimine hydrochloride[I(b)],
3. 1-[5'-chlorospiro(cyclohexane-1,2'-indan)-4-yl] piperidine hydrochloride[I(b)],
4. 1-[6'-ethylspiro(cyclohexane-1,2'-indan)-4-yl]-pyrrolidine hydrochloride[I(b)], and the like.

EXAMPLE 37B

4'-Fluoro-4-[[spiro[cyclohexane-1,2'-indan]-4-yl]amino]butyrophenone hydrochloride[I(b)]

To a solution of 1.12 g. (0.0047 M) of spiro(cyclohexan-1,2'-indan)-4-amine hydrochloride[I(b)] (prepared as in Example 33B) in 30 ml. of dimethylformamide, there is added 0.22, g. of sodium hydride. Following about 1 hour of stirring at room temperature, 0.81 g. of potassium iodide, 1.32 g. of potassium carbonate and 1.14 g. of the 2,2-dimethyl-1,3-propanediol ketal of 4-chloro-4'-fluorobutyrophenone are added. The mixture is then stirred in an oil bath for about 18 hours at about 90° C. The solvent is removed under vacuum and the residue dissolved in benzene and water. The organic layer is washed with water and brine and evaporated to dryness. The residue is then stirred with 15 ml. of methanol and 7.5 ml. of 2.5 N hydrochloric acid for about 2 hours. Most of the methanol is removed under vacuum and the solid collected on a filter. Two recrystallizations from methylene chloride: ethyl acetate give 0.84 g. (46% yield) of 4'-fluoro-4-[[spiro[cyclohexane-1,2'-indan]-4-yl]aminobutyrophenone hydrochloride[I(b)], having a melting point of 195° to 198° C.

Anal. Calcd. for $C_{24}H_{29}ClFNO$: C, 71.71; H, 7.27.

Found: C, 71.68; H, 7.14.

EXAMPLE 38B

4'-Fluoro-4-[[5'-methylspiro[cyclohexane-1,2'-indan]-4-yl]amino]butyrophenone hydrochloride[I(b)]

A suspension of 1.5 g. (0.0049 M) of 5'-methylspiro(cyclohexane-1,2'-indan)-4-amine hydrochloride[I(b)] (prepared as in Example 34B) in 30 ml. of methylene chloride is shaken with 25 ml. of N sodium hydroxide solution until all the solid is dissolved. The organic layer is separated and evaporated to dryness. To a solution of the residue in 25 ml. of dimethylformamide, 1 g. of potassium iodide, 1.53 g. of potassium carbonate and 1.41 g. of the 2,2-dimethyl-1,3-propanediol ketal of 4-chloro-4'-fluorobutyrophenone are added. Following about 18 hours of heating in an oil bath at about 90° C., the solvent is removed under vacuum. The residue is dissolved in benzene and water, the organic layer washed with water and brine and then evaporated to dryness. A mixture of the residue in 10 ml. of 2.5 N hydrochloric acid and 20 ml. of methanol is stirred for about 2 hours at room temperature. Most of the methanol is then removed under vacuum and the solid collected on a filter. This is recrystallized from methanol: ethyl acetate to give 0.61 g. (30% yield) of 4'-fluoro-4-[[5'-methylspiro[cyclohexane-1,2'-indan]-4-yl]-amino]butyrophenone hydrochlorde[I(b)], melting at 204° to 206° C.

Anal. Calcd. for $C_{25}H_{31}ClFNO$: C, 72.18; H, 7.51; N, 3.37.

Found: C, 72.28; H, 7.73; N, 3.29.

EXAMPLE 39B

4'-Fluoro-4-[[5'-methoxyspiro[cyclohexane-1,2'-indan]-4-yl]amino]butyrophenone hydrochloride[I(b)]

A suspension of 0.69 g. (0.0026 M) of 5'-methoxyspiro(cyclohexane-1,2'-indan)-4-amine hydrochloride[I(b)] (prepared in Example 35B) in 15 ml. of methylene chloride is shaken with 10 ml. of N sodium hydroxide solution until all of the solid is dissolved. The organic layer is separated and evaporated to dryness. To a solution of the residue in 15 ml. of dimethylformamide, 0.52 g. of potassium iodide, 0.81 g. of potassium carbonate and 0.75 g. of the 2,2-dimethyl-1,3-propanediol ketal of 4-chloro-4'-fluorobutyrophenone are added. After about 18 hours of heating at about 90° C., the solvent is removed under vacuum. The residue is dissolved in benzene and water, the organic layer washed with water and brine and evaporated to dryness. The residue is dissolved in 5 ml. of 2.5 N hydrochloric acid and 10 ml. of methanol. After standing for about 3 hours at room temperature most of the methanol is removed under vacuum. The solid that precipitates is recrystallized from methylene chloride: ethyl acetate to give 0.52 g. (46%) of 4'-fluoro-[[5'-methoxyspiro[cyclohexane-1,2'-indan]-4-yl]amino]-butyrophenone hydrochloride[I(b)], melting at 190° to 193° C.

Anal. Calcd. for $C_{25}H_{31}ClFNO_2$: C, 69.51; H, 7.23; N, 3.24.

Found: C, 69,62; H, 7.20; N, 3.11.

Following the procedures of Examples 37B through 39B but substituting the same and other (a) acid addition salts of spiro(cyclohexane-1,2'-indan)-4-amines-[I(b)] and (b) the 2,2-dimethyl-1,3-propanediol ketals of the same and other ω-haloalkanaryl ketones in stoichiometrically appropriate amounts as starting materials, such as 1. spiro(cyclohexane-1,2'-indan)-4-amine hydrochloride [I(b)] and the 2,2-dimethyl-1,3-propanediol ketal of 3-bromo-4'-ethylpropiophenone,
2. 7'-chlorospiro(cyclohexane-1,2'-indan)-4-amine hydrobromide[I(b)] and the 2,2-dimethyl-1,3-propanediol ketal of 3',4-dichlorobutyrophenone,
3. 6'-ethylspiro(cyclohexane-1,2'-indan)-4-amine hydrochloride[I(b)] and the 2,2-dimethyl-1,3-propanediol ketal of 4-chloro-2'-ethoxybutyrophenone,
4. 4'-acetylamidospiro(cyclohexane-1,2'-indan)-4-amine hydrochloride[I(b)] and the 2,2-dimethyl-1,3-propanediol ketal of 5-chloro-4'-ethylvalerophenone, and the like, yields, respectively, 1. 4'-ethyl-3[[spiro[cyclohexane-1,2'-indan]-4-yl]amino]propiophenone hydrochloride[I(b)],
2. 3'-chloro-4-[[7'-chlorospiro[cyclohexane-1,2'-indan]-4-yl]amino]butyrophenone hydrochloride[I(b)],
3. 2'-ethoxy-4-[[6'-ethylspiro[cyclohexane-1,2'-indan]-4-yl]amino]butyrophenone hydrochloride[I(b)],
4. 4'-ethyl-5-[[4'-acetylamidospiro[cyclohexane-1,2'-indan]-4-yl]amino]valerophenone hydrochloride[I(b)], and the like.

EXAMPLE 40B

Ethyl spiro(cyclohexane-1,2'-indan)-4-carbamate[I(b)]

A suspension of 3.03 g. (0.0128 M) of spiro(cyclohexane-1,2'-indan)-4-amine hydrochloride[I(b)] (prepared as in Example 33B) in 65 ml. of methylene chloride is shaken with 50 ml. of N sodium hydroxide solution until the solid is completely dissolved. The organic layer is separated and evaporated to dryness. To an ice cooled solution of the residue in 25 ml. of pyridine, 2 ml. of ethyl chloroformate is added dropwise. After about 5 hours in the cold the mixture is poured onto ice: water. The precipitated solid is recrystallized from Skellysolve B to give 2.9 g. (83%) of ethyl spiro(cyclohexane-1,2'-indan)-4-carbamate[I(b)], melting at 70° to 73° C.

EXAMPLE 41B

Ethyl 5'-methylspiro(cyclohexane-1,2'-indan)-4-carbamate[I(b)]

A solution of the amine free base prepared from 1.97 g. (0.00785 M) of 5'-methylspiro(cyclohexane-1,2'-indan)-4-amine hydrochloride[I(b)] (obtained as in Example 34B), in 16 ml. of pyridine, is cooled in an ice bath. After the addition of 1.25 ml. of ethyl chloroformate the mixture is allowed to stand in the cold for about 5.5 hours and then poured into ice water. The gum that precipitates is extracted with ether. The combined extracts are washed successively with water, ice cold 2.5 N hydrochloric acid, water, aqueous sodium bicarbonate solution and brine, and evaporated to dryness. The residue is chromatographed over a 250 ml. column of silica gel with elution by 5% ethyl acetate: methylene chloride. The fractions shown alike by TLC are combined to give 2.19 g. of ethyl 5'-methylspiro(-cyclohexane-1,2'-indan)-4-carbamate[I(b)], having a melting point of 55° to 60.5° C.

EXAMPLE 42B

Ethyl 5'-methoxyspiro(cyclohexane-1,2'-indan)-4-carbamate[I(b)]

To an ice cooled solution of the amine free base prepared from 2.38 g. (0.00926 M) of 5'-methoxyspiro(cyclohexane-1,2'-indan)-4-amine hydrochloride[I(b)] (obtained as in Example 35B), in 0.82 ml. of triethylamine and 40 ml. of tetrahydrofuran, 0.87 ml. of ethyl chloroformate is added. The mixture is kept in the cold for about 6 hours and then evaporated to dryness under vacuum. The residue is dissolved in water and ether and the organic layer washed with water and brine and then evaporated to dryness. The residue is chromatographed on a 250 ml. column of silica gel with elution by 10% acetone: Skellysolve B. The fractions shown alike by TLC are combined to yield 2.22 g. (79%) of ethyl 5'-methoxyspiro(cyclohexane-1,2'-indan)-4-carbamate[I(b)] as a waxy solid.

Following the procedures of Examples 40B through 42B but substituting another spiro(cyclohexane-1,2'-indan -4-amine[I(b)] and another lower alkyl haloformate, such as
1. 5'-chlorospiro(cyclohexane-1,2'-indan)-4-amine hydrochloride[I(b)] and methyl chloroformate,
2. 4'-ethylspiro(cyclohexane-1,2'-indan)-4-amine hydrochloride[I(b)] and propyl chloroformate, and the like, yields, respectively,
1. methyl 5'-chlorospiro(cyclohexane-1,2'-indan)-4-carbamate[I(b)],
2. propyl 4'-ethylspiro(cyclohexane-1,2'-indan)-4-carbamate[I(b)], and the like.

EXAMPLE 43B

Spiro(cyclohexane-1,2'-indan)-4-methylamine hydrochloride[I(b)]

A solution of 2.9 g. (0.0106 M) of ethyl spiro(cyclohexane-1,2'-indan)-4-carbamate[I(b)] (prepared in Example 40B) in 50 ml. of tetrahydrofuran, is added to a well stirred suspension of 0.5 g. of lithium aluminum hydride in 25 ml. of tetrahydrofuran. The mixture is heated at reflux for about 6 hours and then cooled in ice. There is added successively 0.5 ml. of water, 0.5 ml. of 15% aqueous sodium hydroxide solution and 1.5 ml. of water. The inorganic gel is collected on a filter and the filtrate evaporated to dryness. An ether solution of the residue is treated with 6 N hydrochloric acid to give 1.8 g. (66%) of spiro(cyclohexane-1,2'-indan)-4-methylamine hydrochloride[I(b)], melting at 251° to 254° C.

Anal. Calcd. for $C_{15}H_{22}ClN.1/3H_2O$: C, 69.88; H, 9.22; N, 5.43.
Found: C, 69.99; H. 8.55; N, 5.25.

EXAMPLE 44B

5'-Methylspiro(cyclohexane-1,2'-indan)-4-methylamine[I(b)]

To a well stirred suspension of 0.33 g. of lithium aluminum hydride in 8 ml. of tetrahydrofuran, a solution of 2.19 g. (0.00764 M) of ethyl 5'-methylspiro(cyclohexane-1,2'-indan)-4-carbamate[I(b)] (prepared in Example 41B) in 50 ml. of tetrahydrofuran is added. The mixture is stirred at room temperature for about 6 hours. After cooling in an ice bath, there is added successively 0.33 ml. of water, 0.33 ml. of 15% sodium hydroxide solution and 0.99 ml. of water. The resulting inorganic gel is collected on a filter, rinsed well with ether and the filtrate evaporated to dryness. A solution of the residual gum in 35 ml. of tetrahydrofuran is added to a well stirred suspension of 0.33 g. of lithium aluminum hydride in 5 ml. of tetrahydrofuran. After about 6 hours of stirring at room temperature the reaction mixture is treated as above. The residual gum is dissolved in a small amount of ether and extracted 3 times with 20 ml. of 2.5 N hydrochloric acid. The combined extracts are washed with ether and made basic. The material that precipitates is extracted with ether and the extracts evaporated to dryness to give 5'-methylspiro(cyclohexane-1,2'-indan)-4-methylamine[I(b)] as gum.

EXAMPLE 45B

5'-Methoxyspiro(cyclohexane-1,2'-indan)-4-methylamine hydrochloride[I(b)]

To a well stirred suspendion of 0.32 g. of lithium aluminum hydride in 8 ml. of tetrahydrofuran, a solution of 2.22 g. (0.00732 M) of ethyl 5'-methoxyspiro(cyclohexane-1,2'-indan)-4-carbamate[I(b)] (prepared in Example 42B) in 50 ml. of tetrahydrofuran is added. After about 18 hours of stirring at room temperature the mixture is cooled in an ice bath and there is added successively 0.32 ml. of water, 0.32 ml. of 15% aqueous sodium hydroxide solution and 96 ml. of water. The resulting precipitate is collected on a filter and the filtrate evaporated to dryness. A solution of the residue in a small amount of ether is extracted with 2.5 N hydrochloric acid. A precipitate suspended in the acid layer is extracted with methylene chloride and evaporated to dryness. The acid portion is made basic, extracted with ether and evaporated to dryness. A solution of the latter residue in ether is treated with an excess of ethereal hydrochloric acid. A precipitate is collected on a filter, combined with the residue from the methylene chloride extract, and recrystallized from methanol: ether to give 0.56 g. (35.1% yield) of 5'-methoxyspiro(cyclohexane-1,2-indan)-4-methylamine hydrochloride-[I(b)], melting at 225° to 229° C.

Anal. Calcd. for $C_{16}H_{24}ClNO.1/2CH_3OH$: C, 66.53; H, 8.80; N, 4.70
Found: C, 66.74; H, 8.54; N, 4.82.

Following the procedures of Examples 34B through 45B but substituting another lower alkyl spiro(cyclohexane-1,2'-indan)-4-carbamate[I(b)] as starting material, such as
1. ethyl 5'-bromospiro(cyclohexane-1,2'-indan)-4-carbamate[I(b)],
2. propyl 4'-ethoxyspiro(cyclohexane-1,2'-indan)-4-carbamate[I(b)], and the like, yields, respectively,
1. 5'-bromospiro(cyclohexane-1,2'-indan)-4-methylamine hydrochloride[I(b)],
2. 4'-ethoxyspiro(cyclohexane-1,2'-indan)-4-methylamine hydrochloride[I(b)], and the like.

EXAMPLE 46B

4'-Fluoro-4-[methyl[spiro[cyclohexane-1,2'-indan]-4-yl]amino]butyrophenone hydrochloride[I(b)]

To a suspension of 1 g. (0.0040 M) of spiro(cyclohexane-1,2'-indan)-4-methylamine hydrochloride[I(b)] (prepared as in Example 43B) in 20 ml. of dimethylformamide, 0.17 g. of sodium hydride is added. After about 1 hour, 0.8 g. of potassium iodide, 1.25 g. of potassium carbonate and 1.15 g. of the 2,2-dimethyl-1,3-propandiol ketal of 4-chloro-4'-fluorobutyrophenone is added to the mixture. The mixture is heated in an oil bath at about 110° C. for about 17 hours and allowed to cool. The solvent is then removed under vacuum and the residue dissolved in benzene and water. The organic layer is washed with water and brine and evaporated to dryness. A mixture of the residue and 7.5 ml. of 2.5 N hydrochloric acid in 15 ml. of methanol is stirred at room temperature for about 2 hours. Most of the methanol is removed under vacuum and the precipitated solid collected on a filter. This is recrystallized twice from methylene chloride: [ethyl acetate to give 0.77 g] (45%) of 4'-fluoro-4-[methyl[spiro[cyclohexane-1,2'-indan]-4-yl]amino]butyrophenone hydrochloride[I(b)], melting at 195° to 197° C., and also named 4'-fluoro-4-[spiro[cyclohexane-1,2'-indan)-4-yl-N-methylamino]butyrophenone hydrochloride.

Anal. Calcd. for $C_{25}H_{31}ClFNO·½H_2O$: C, 70.65; H, 7.35; N, 3.29.
Found: C, 71.10; H, 7.44; N, 3.20.

EXAMPLE 47B

4'-Fluoro-4-[methyl[5'-methylspiro[cyclohexane-1,2'-indan]-4-yl]amino]butyrophenone hydrochloride[I(b)]

A mixture of 0.72 g. (0.00314 M) of 5'-methylspiro(cyclohexane-1,2'-indan)-4-methylamine[I(b)] (prepared in Example 44B), 0.99 g. of potassium carbonate, 0.65 g. of potassium iodide and 0.9 g. of the 2,2-dimethyl-1,3-propanediol ketal of 4-chloro-4'-fluorobutyrophenone in 16 ml. of dimethylformamide is heated in an oil bath at about 90° C. for about 18 hours. Most of the solvent is removed under vacuum and the residue dissolved in benzene and water. The organic layer is washed with water and brine and evaporated to dryness. The residue is stirred with 12 ml. of methanol and 6 ml. of 2.5 N hydrochloric acid for about 3 hours at room temperature. Most of the methanol is removed under vacuum and the residue extracted with methylene chloride. The extract is washed with N sodium hydroxide solution and evaporated to dryness. The residue is chromatographed on a 200 ml. column of silica gel with elution by 30% Skellysolve B: methylene chloride saturated with ammonium hydroxide. Those fractions found alike by TLC are dissolved in methylene chloride. The latter solution is washed with 2.5 N hydrochloric acid, evaporated to dryness and recrystallized from methanol: ether to yield 0.25 g. (18.5%) of 4'-fluoro-4-[methyl[5'-methylspiro[cyclohexane-1,2'-indan]butyrophenone hydrochloride[I(b)], melting at 212.5° to 214° C.

Anal. Calcd. for $C_{26}H_{33}ClFNO$: C, 72.62; H, 7.74; N, 3.26.
Found: C, 72.17; H, 7.79; N, 3.26.

EXAMPLE 48B

4'-Fluoro-4-[methyl[5'-methoxyspiro[cyclohexane-1,2'-indan]-4-yl]amino]butyrophenone hydrochoride[I(b)]

A mixture of the amine free base prepared from 0.84 g. (0.0030 M) of 5'-methoxyspiro(cyclohexane-1,2'-indan)-4-methylamine hydrochloride[I(b)] (obtained as in Example 45B), 0.95 g. of potassium carbonate, 0.62 g. of potassium iodide and 0.86 g. of the 2,2-dimethyl-1,3-propane-diol ketal of 4-chloro-4'-fluorobutyrophenone in 15 ml. of dimethylformamide is heated in an oil bath at about 90° C. for about 18 hours. Most of the solvent is removed under vacuum and the residue dissolved in benzene and water. The organic layer is washed with water and brine and then evaporated to dryness. A solution of the residue in 12 ml. of methanol and 6 ml. of 2.5 N hydrochloric acid is stirred at room temperature for about 3 hours. Most of the methanol is removed under vacuum and the residue extracted with methylene chloride. The residue is washed with N aqueous sodium hydroxide solution and evaporated to dryness. The residue is chromatographed on a 200 ml. of column of silica gel with elution by 30% Skellysolve B: methylene chloride saturated with ammonium hydroxide. Those fractions found alike by TLC are pooled and evaporated to dryness. The residue is streaked onto 3 preparative TLC plates and eluted with methylene chloride saturated with ammonium hydroxide. The band having the strongest ultraviolet absorbtion is eluted and evaporated to dryness to give 0.45 g. (33.6% yield) of p-fluoro-4-[methyl]5'-methoxyspiro[cyclohexane-1,2'-indan]-4-yl]amino]-butyrophenone hydrochlorede[I(b)] as an amorphous foam.

Following the procedures of Example 46B through 48B but substituting the same and other (a) acid addition salts of spiro(cyclohexane-1,2'-indan)-4-lower alkylamines [I(b)] and (b) the 2,2-dimethyl-1,3-propanediol ketal of ω-haloalkanaryl ketones in stoichiometrically appropriate amounts as starting materials, such as 1. spiro(cyclohexane-1,2'-indan)-4-methylamine hydrochloride[I(b)] and the 2,2-dimethyl-1,3-propanediol ketal of 3'-bromo-3-chloropropiophenone,
2. 6'-ethylspiro(cyclohexane-1,2'-indan)-4-methylamine hydrochloride[I(b)] and the 2,2-dimethyl-1,3-propanediol ketal of 4-chloro-2'-ethoxybutyrophenone,
3. 5'-propionylamidospiro(cyclohexane-1,2'-indan)-4-methylamine hydrochloride[I(b)] and the 2,2-dimethyl-1,3-propanediol ketal of 5-chloro-4'-propylvalerophenone and the like, yields, respectively,
1. 3'-bromo-3-[methyl[spiro[cyclohexane-1,2'-indan]-4-yl]amino]propiophenone hydrochloride[I(b)],
2. 2'-ethoxy-4-[methyl[6'-ethylspiro[cyclohexane-1,2'-indan]-4-yl]amino]butyrophenone hydrochloride[I(b)],
3. 4'-propyl-5-[methyl[5'-propionylamidospiro[cyclohexane-1,2'-indan]-4-yl]amino]valerophenone hydrochloride[I(b)], and the like.

EXAMPLE 49B

1'-Hydroxyspiro(cyclohexane-1,2'-indan)-4-one ethylene ketal[17]

A solution of 2.6 g. (0.01 M) of spiro(cyclohexane-1,2'-indan)-1',4-dione ethylene ketal[9] (prepared as in Example 16B) in 50 ml. of tetrahydrofuran is added to a well stirred suspension of 0.5 g. of lithium aluminum hydride in 10 ml. of tetrahydrofuran. The mixture is stirred at room temperature for about 5 hours, cooled in ice and treated successively with 0.5 ml. of water, 0.5 ml. of 15% aqueous sodium hydroxide solution and 1.5 ml. of water. The inorganic gel is removed by filtration and the filtrate evaporated to dryness. The residue is recrystallized from cyclohexane to give 2.45 g. (95%) of 1'-hydroxyspiro(cyclohexane-1,2'-indan)-4-one ethylene ketal[17], having a melting point of 125° to 128° C.

Anal. Calcd. for $C_{16}H_{20}O_3$: C, 73.82; H, 7.74.
Found: C, 73.48; H, 7.78.

Following the procedure of Example 49B but substituting other spiro(cyclohexane-1,2'-indan)-1,4-dione alkylene ketals[9] as starting materials, such as
5'-methoxyspiro(cyclohexane-1,2'-indan)-1',4-dione ethylene ketal[9] yields, 1'-hydroxy-5'-methoxyspiro(cyclohexane-1,2'-indan)-4-one ethylene ketal[17].

EXAMPLE 50B

1'-Acetoxyspiro(cyclohexane-1,2'-indan)-4-one[19]

1. A solution of 2.45 g. (0.0094 M) of 1'-hydroxyspiro(cyclohexane-1,2'-indan)-4-one ethylene ketal[17] (prepared in Example 49B) and 5 ml. of 2.5 N hydrochloric acid in 50 ml. of acetone is allowed to stand for about 17 hours at room temperature. Most of the solvent is removed under vacuum and the residue dissolved in water and ether. The organic layer is washed with water and brine and evaporated to dryness to give 1'-hydroxyspiro(cyclohexane-1,2'-indan)-4-one[18], as a gum.

2. A solution of the 1'-hydroxyspiro(cyclohexane-1,2'-indan)-4-one[18] obtained in (1), above, and 4 ml. of acetic anhydride in 16 ml. of pyridine is allowed to stand at room temperature for about 7 hours and then poured into ice:water. The precipitate is extracted with ether. This extract is washed successively with water, ice cold 2.5 N hydrochloric acid, water and saturated aqueous sodium bicarbonate solution and then evaporated to dryness. The residual solid is recrystallized from Skellysolve B to give 1.82 g. (75% yield) of 1'-acetoxyspiro(cyclohexane-1,2'-indan)-4-one[19], melting at 87° to 89° C.

Anal. Calcd. for $C_{16}H_{18}O_3$: C, 74.39; H, 7.02.
Found: C, 73.93; H, 6.95.

Following the procedure of Example 50B but substituting other 1'-hydroxyspiro(cyclohexane-1,2'-indan)-4-one alkylene ketals[17] and an anhydride of another hydrocarbon carboxylic acid for acetic anhydride, such as
1. 1'-hydroxy-4'-acetylamidospiro(cyclohexane-1,2'-indan)-4-one ethylene ketal[17] and propionic anhydride,
2. 1'-hydroxy-5'-ethylspiro(cyclohexane-1,2'-indan)-4-one ethylene ketal[17] and isopropionic anhydride, and the like, yields, respectively,
1. 1'-propionyloxy-4'-acetylamidospiro(cyclohexane-1,2'-indan)-4-one[19],
2. 1'-isopropionyloxy-5'-ethylspiro(cyclohexane-1,2'-indan)-4-one[19], and the like.

EXAMPLE 51B

1'-Acetoxyspiro(cyclohexane-1,2'-indan)-4-ol methanesulfonate[21]

1. To a solution of 1.82 g. (0.0071 M) of 1'-acetoxy(-cyclohexane-1,2'-indan)-4-one[19] (prepared in Example 50B) in 25 of 95% isopropanol, 0.32 g. of sodium borohydride is added. Following about 1 hour of stirring at room tempeerature most of the solvent is removed under vacuum. The residue is dissolved in ether and water, the organic layer is washed with water and brine and evaporated to dryness to give 1'-acetoxyspiro(cyclohexane-1,2'-indan)-4-ol[20].

2. The residual gummy 1'-acetoxyspiro(cyclohexane-1,2'-indan)-4-ol[20] obtained in (1), above, is dissolved in pyridine. This solution is cooled in ice and treated with 1.7 ml. of methanesulfonyl chloride. After standing in the cold for about 17 hours the mixture is poured into ice and water. The gum that precipitates is extracted with ether. The organic layer is washed successively with water, 2.5 N hydrochloric acid, water and brine and evaporated to dryness. The residue is recrystallized twice from a mixture of ether and petroleum ether to give 1.54 g. (65% yield) of 1'-acetoxyspiro(cyclohexane-1,2'-indan-4-ol methanesulfonate[21] having a melting point of 97° to 100° C.

Anal. Calcd. for $C_{17}H_{20}O_5S$: C, 60.69; H, 5.99; M.W. 338.
Found: C, 60.60; H, 6.58; m/e 338.

Following the procedure of Example 51B but substituting other 1'-acyloxyspiro(cyclohexane-1,2'-indan)-4-ones[19] and other lower alkylsulfonyl halides, such as
1. 1'-propionyloxy-5'-chlorospiro(cyclohexane-1,2'-indan)-4-one[19] and ethanesulfonyl bromide,
2. 1'-butyroyloxy-7'-ethoxyspiro(cyclohexane-1,2'-indan)-4-one[19] and butanesulfonyl chloride, and the like, yields respectively.
1. 1'-propionyloxy-5'-chlorospiro(cyclohexane-1,2'-indan)-4-ol ethanesulfonate[21],
2. 1'-butyryloxy-7'-ethoxyspiro(cyclohexane-1,2'-indan)-4-ol butanesulfonate[21], and the like.

EXAMPLE 52B

1'-Hydroxyspiro(cyclohexane-1,2'-indan)-4-amine[I(b)]; also named 4-aminospiro(cyclohexane-1,2'-indan)-1'-ol[I(b)]

A mixture of 5 g. (0.015 M) of 1'-acetoxyspiro(cyclohexane-1,2'-indan)-4-ol methanesulfonate[21] (obtained as in Example 51B) and 5 g. of sodium azide in 50 ml. of dimethylformamide is stirred for about 17 hours in an oil bath at about 90° C. The solvent is then removed under vacuum and the residue dissolved in benzene and water. The organic layer is washed with water and brine and then evaporated to dryness to give 1'-acetoxyspiro(cyclohexane1,2'-indan)-4-ylazide[22].

A solution of the crude azide[22] in 80 ml. of tetrahydrofuran is added to 1.2 g. of lithium aluminum hydride in 20 ml. of tetrahydrofuran. After about 4.5 hours of stirring at room temperature the mixture is cooled in ice and treated successively with 1.2 ml. of water, 1.2 ml. of 15% aqueous sodium hydroxide solution and 3.6 ml. of water. The inorganic gel is collected on a filter and the filtrate evaporated to dryness. The residue is recrystallized from a small amount of ethyl acetate to give 1.71 g. (53% of theoretical yield) of 1'-hydroxyspiro(cyclohexane-1,2'-indan)-4-amine[I(b)], melting at 156° to 160° C. the analytical sample melts at 158° to 161° C.

Anal. Calcd. for $C_{14}H_{19}NO$: C, 77.38; H, 8.81; N, 6.45.
Found: C, 76.98; H, 8.79; N, 6.41.

Extracting the thus obtained free base form of the compound with ether and treating the extract with the an ethereal solution of a suitable acid (e.g., hydrochloric), gives the corresponding acid addition salt form of 1'-hydroxyspiro(cyclohexane-1,2'-indan)-4-amine[I(b)].

Following the procedure of Example 52B but substituting other 1'-acyloxyspiro(cyclohexane-1,2'-indan)-4-ol lower alkylsulfonates[21] as starting mateials, such as
1. 1'-acetoxy-4'-ethylspiro(cyclohexane-1,2'-indan)-4-ol propanesulfonate[21],
2. 1'-propionyloxy-5'-fluorospiro(cyclohexane-1,2'-indan)-4-ol ethanesulfonate[21], and the like, yields, respectively, 1. 1'-hydroxy-4'-ethylspiro(cyclohexane-1,2'-indan)-4-amine[I(b)],
2. 1'-hydroxy-5'-fluorospiro(cyclohexane-1,2'-indan)-4-amine[I(b)], and the like.

EXAMPLE 53B

4'-Fluoro-4-[[1'-hydroxyspiro[cyclohexane-1,2'-indan]-4-yl]amino]butyrophenone hydrochloride[I(b)]

A mixture of 1.71 g. (0.0079 M) of 1'-hydroxyspiro(-cyclohexane-1,2'-indan)-4-amine[I(b)] (prepared in Example 51B), 1.58 g. of potassium iodide, 4.25 g. of potassium carbonate and 2.28 g. of the 2,2-dimethyl-1,3-propanediol of 4-chloro-p-fluorobutyrophenone in 40 ml. of dimethylformamide is stirred for about 17 hours in an oil bath at about 90° C. The solvent is then removed under vacuum and the residue partitioned between water and benzene. The organic layer is washed with water and brine and evaporated to dryness. A mixture of the residue and 7.5 ml. of 2.5 N hydrochloric acid in 15 ml. of methanol is stirred at room temperature for about 4 hours. Most of the methanol is removed under vacuum and the precipitated solid collected on a filter. This material is recrystallized to give 1.03 g. (33% yield) of 4'-fluoro-4-[[1'-hydroxyspiro[cyclohexane-1,2'-indan]-4-yl]amino]-butyrophenone hydrochloride[I(b)], having a melting point of 190° to 193° C.

Anal. Calcd. for $C_{24}H_{29}ClFNO_2$: C, 68.97; H, 6.99 N, 3.35.

Found: C, 69.37; H, 7.77 N, 3.11.

Following the procedure of Example 53B but substituting the same and other (a) 1'-hydroxyspiro(cyclohexane-1,2'-indan)-4-amines[I(b)] and (b) the 2,2-dimethyl-1,3-propanediol ketals of ω-haloalkanaryl ketones in stoichiometrically appropriate amounts as starting materials, such as 1. 1'-hydroxyspiro(cyclohexane-1,2'-indan)-4-amine[I(b)] and the 2,2-dimethyl-1,3-propanediol ketal of 2-bromo-4-ethylpropiophenone,
2. 1'-hydroxy-7'-fluorospiro(cyclohexane-1,2'-indan)-4-amine[I(b)] and the 2,2-dimethyl-1,3-propanediol ketal of 3',4-dichlorobutyrophenone,
3. 1'-hydroxy-6'-ethoxyspiro(cyclohexane-1,2'-indan)-4-amine[I(b)] and the 2,2-dimethyl-1,3-propanediol ketal of 4-chloro-3-ethoxybutyrophenone, and the like, yields, respectively, 1. 4'-ethyl-3-[[1'-hydroxyspiro[cyclohexane-1,2'-indan]-4-yl]amino]propiophenone hydrochloride[I(b)],
2. 3'-chloro-4-[[7'-fluoro-1'-hydroxyspiro[cyclohexane-1,2'-indan]-4-yl]amino]butyrophenone hydrochloride-[I(b)],
3. 3'-ethoxy-4-[[6'-ethoxy-1'-hydroxyspiro[cyclohexane-1,2'-indan]-4-yl]amino]butyrophenone hydrochloride[I(b)], and the like.

EXAMPLE 54B

Ethyl 1'-hydroxyspiro(cyclohexane-1,2'-indan)-4-carbamate[I(b)]

A suspension of 3.5 g. of 1'-hydroxyspiro(cyclohexane-1,2'-indan)-4-amine hydrochloride[I(b)] (obtained as in the paragraph immediately following Example 52B) in 65 ml. of methylene chloride is shaken with 50 ml. of N sodium hydroxide solution until the solid is completely dissolved. The organic layer is separated and evaporated to dryness. To an ice cooled solution of the residue in 25 ml. of pyridine, 2 ml. of ethyl chloroformate is added dropwise. After about 5 hours in the cold the mixture is poured into ice and water. The precipitated solid is recrystallized from Skellysolve B to give ethyl 1'-hydroxyspiro(cyclohexane-1,2'-indan)-4-carbamate[I(b)].

EXAMPLE 55B

1'-Hydroxyspiro(cyclohexane-1,2'-indan)-4-methylamine hydrochloride[I(b)]

A solution of 3 g. of ethyl 1'-hydroxyspiro(cyclohexane-1,2'-indan)-4-carbamate[I(b)] (prepared as in Example 54B) in 50 ml. of tetrahydrofuran, is added to a well stirred suspension of 0.5 g. of lithium aluminum hydride in 25 ml. of tetrahydrofuran. The mixture is heated at reflux for about 6 hours and then cooled in ice. There is added successively 0.5 ml. of water, 0.5 ml. of 15% aqueous sodium hydroxide solution and 1.5 ml. of water. The inorganic gel is separated by filtration and the filtrate evaporated to dryness. An ether solution of the residue is treated with 6 N hydrochloric acid to give 1'-hydroxyspiro(cyclohexane-1,2'-indan)-4-methylamine hydrochloride[I(b)].

EXAMPLE 56B

1-[1'-Hydroxyspiro(cyclohexane-1,2'-indan)-4-yl]piperidine hydrochloride[I(b)]

Following the procedure of Example 36B but substituting a stoichiometrically appropriate amount of 1'-hydroxyspiro(cyclohexane-1,2'-indan)-4-amine hydrochloride[I(b)] (prepared as in the first paragraph following Example 52B) as starting material, yields 1-[1'-hydroxyspiro(cyclohexane-1,2'-indan)-4-yl]piperidine hydrochloride[I(b)].

Following the procedure of Example 56B but substituting other 1'-hydroxyspiro(cyclohexane-1,2'-indan)-4-amine acid addition salts[I(b)] and other dihaloalkanes in stoichiometrically appropriate amounts as starting materials, such as 1. 5'-chloro-1'-hydroxyspiro(cyclohexane-1,2'-indan)-4-amine hydrochloride[I(b)] and 1,6-diiodohexane,
2. 1'-hydroxy-4'-propoxyspiro(cyclohexane-1,2'-indan)-4-amine hydrochloride[I(b)] and 1,4-dibromobutane, and the like, yields, respectively, 1. 1-[5'-chloro-1'-hydroxyspiro(cyclohexane-1,2'-indan)-4-yl]hexamethyleneimine hydrochloride[I(b)],
2. 1-[1'-hydroxy-4'-propoxyspiro(cyclohexane-1,2'-indan)-4-yl]pyrrolidine hydrochloride[I(b)], and the like.

EXAMPLE 57B

4'-fluoro-4-[methyl[1'-hydroxyspiro[cyclohexane-1,2'-indan]-4-yl]amino]butyrophenone hydrochloride[I(b)]

Following the procedure of Examples 46B through 48B but substituting a stoichiometrically appropriate amount of 1'-hydroxyspiro(cyclohexane-1,2'-indan)-4-methylamine hydrochloride[I(b)] (prepared as in Example 55B) as starting material, yields 4'-fluoro-4-[methyl[1'-hydroxyspiro[cyclohexane-1,2'-indan]-4-yl]amino]butyrophenone hydrochloride[I(b)].

Following the procedure of Example 57B but substituting other 1'-hydroxyspiro(cyclohexane-1,2'-indan)-4-lower alkylamines[I(b)] and the 2,2-dimethyl-1,3-propanediol ketals of ω-haloalkanaryl ketones in stoichiometrically appropriate amounts as starting materials, such as 4′-ethoxy-1′-hydroxyspiro(cyclohexane-1,2′-indan)-4-propylamine hydrochloride[I(b)] and the 2,2-dimethyl-1,3-propanediol ketal of 4-chloro-3′-ethylbutyrophenone, yields, 3′-ethyl-4-[propyl[4′-ethoxy-1′-hydroxyspiro[cyclohexane-1,2′-indan]-4-yl]amino]butyrophenone hydrochloride[I(b)].

EXAMPLE 58B

1′-Chlorospiro(cyclohexane-1,2′-indan)-4-one ethylene ketal[23]

A solution of 6.5 g. (0.025 M) of 1′-hydroxyspiro(cyclohexane-1,2′-indan)-4-one ethylene ketal[17] (prepared as in Example 49B) in 86 ml. of tetrahydrofuran is cooled in ice: methanol. To this there is added dropwise 15.6 ml. of 1.64 N butyl lithium in pentane, and after about 5 minutes, 2.04 ml. (3.03 g.) of methane sulfonyl chloride in 43 ml. of tetrahydrofuran. After standing for about 4 hours in the cold, the solvent is removed under vacuum. The residue is treated with ether and the inorganic solid collected on a filter. The filtrate is evaporated to dryness and the residue recrystallized from petroleum ether to give 6.06 g. (87%) of 1′-chlorospiro(cyclohexane-1,2′-indan)-4-one ethylene ketal[23], having a melting point of 103.5 to 108° C.

Anal. Calcd. for $C_{16}H_{19}ClO_2$: Calcd. M.W. 278.
Found: m/e 278.

Following the procedure of Example 58B but substituting other 1′-hydroxyspiro(cyclohexane-1,2′-indan)-4-one ethylene ketals and other lower alkyl sulfonyl halides, such as 1. 1′-hydroxy-4′-chlorospiro(cyclohexane-1,2′indan)-4-one ethylene ketal[17] and ethane sulfonyl bromide,
2. 1′-hydroxy-6′-propoxyspiro(cyclohexane-1,2′indan)-4-one ethylene ketal[17] and ethane sulfonyl chloride, and the like, yields, respectively, 1. 1′-bromo-4′-chlorospiro(cyclohexane-1,2′-indan)-4-one ethylene ketal[23],
2. 1′-chloro-6′-propoxyspiro(cyclohexane-1,2′-indan)-4-one ethylene ketal[23], and the like.

EXAMPLE 59B

1′-Aminospiro(cyclohexane-1,2′-indan)-4-one ethylene ketal[24]

A mixture of 3.5 g. (0.013 M) of 1′-chlorospiro(cyclohexane-1,2′-indan)-4-one ethylene ketal[23] (prepared as in Example 58B) and 3.5 g. of sodium azide in dimethylformamide is stirred in an oil bath at about 90° C. for about 17 hours. The solvent is removed under vacuum and the solid dissolved in benzene and water. The organic layer is washed with water and brine and evaporated to dryness. A solution of the residue in 60 ml. of tetrahydrofuran is added to 0.5 g. of lithium aluminum hydride in 10 ml. of tetrahydrofuran. After standing for about 4.5 hours the mixture is cooled in ice and treated successively with 0.5 ml. of water, 0.5 ml. of 15% aqueous sodium hydroxide solution and 1.5 ml. of water. The inorganic gel is collected on a filter and the filtrate evaporated to dryness. The residual gum is dissolved in ether and treated with 5 N hydrochloric acid in ether, to give 2.42 g. (81% yield) of 1′-aminospiro(cyclohexane1,2′-indan)-4-one ethylene ketal[24], having a melting point of 224° to 227° C.

Anal. Calcd. for $C_{16}H_{22}ClNO_2$: M.W. 259
Found: m/e 259.

Following the procedure of Example 59B but substituting other 1′-halospiro(cyclohexane-1,2′-indan)-4-one ethylene ketals[23] as starting materials, such as 1. 1′-bromo-5′-fluorospiro(cyclohexane-1,2′-indan)-4-one ethylene ketal[23],
2. 1′-chloro-6′-nitrospiro(cyclohexane-1,2′-indan)-4-one ethylene ketal[23], and the like, yields, respectively, 1. 1′-amino-5′-fluorospiro(cyclohexane-1,2′-indan)-4-one ethylene ketal[24],
2. 1′-amino-6′-nitrospiro(cyclohexane-1,2′-indan)-4-one ethylene ketal[24], and the like.

EXAMPLE 60B

1′-acetamidospiro(cyclohexane-1,2′-indan)-4-one[26]

1. A solution of 7 g. of 1′-aminospiro(cyclohexane-1,2′-indan)-4-one ethylene ketal[24] (prepared as in Example 59B) and 30 ml. of acetic anhydride in 60 ml. of pyridine is allowed to stand at room temperature for about 5 hours. The mixture is poured into ice: water and the precipitated gum extracted with ether. The organic layer is washed successively with watere, 2.5 N hydrochloric acid and brine and evaporated to dryness to give 1′-acetamidospiro(cyclohexane-1,2′-indan)-4-one ethylene ketal[25].

2. The residual 1′-acetamidospiro(cyclohexane-1,2′indan)-4-one ethylene ketal[25], obtained in (1), above, and 10 ml. of 2.5 N hydrochloric acid are dissolved in 100 ml. acetone. After about 20 hours at room temperature most of the solvent is removed under vacuum. The residue is dissolved in methylene chloride and water. The organic layer is washed with water and brine and evaporated to dryness. The residual gum is chromatographed on a 600 ml. column of silica gel with elution by 25% acetone in methylene chloride. The crystalline fractions are eluted with ethyl acetate: cyclohexane to give 3.81 g. of 1′-acetamidospiro(cyclohexane-1,2′-indan)-4-one[26], having a melting point of 113° to 116° C.

Following the procedure of Example 60B but substituting another 1′-aminospiro(cyclohexane-1,2′-indan)-4-one ethylene ketal[24] and another anhydride of a hydrocarbon carboxylic acid, such as 1. 1′-amino-4′-ethylspiro(cyclohexane-1,2′-indan)-4-one ethylene ketal[24] and propionic anhydride,
2. 1′-amino-6′-propoxyspiro(cyclohexane-1,2′-indan)-4-one ethylene ketal[24] and isopropionic anhydride, and the like, yields, respectively, 1. 4′-ethyl-1′-propionylamidospiro(cyclohexane-1,2′-indan)-4-one [26],
2. 1′-isopropionylamido-6′-propoxyspiro(cyclohexane-1,2′-indan)-4-one[26], and the like.

EXAMPLE 61B

1′-Acetamidospiro(cyclohexane-1,2′-indan)-4-ols[27]

To 3.81 g. of 1′-acetamidospiro(cyclohexane-1,2′-indan)-4-one[26] (prepared in Example 60B) in 100 ml. of isopropanol, 0.6 g. of sodium borohydride is added. After about 5 hours most of the solvent is removed under vacuum and the residue suspended in water. The resulting solid is collected on a filter and recrystallized from aqueous methanol. There is obtained first 0.9 g. (24% yield) of 1'-acetamidospiro(cyclohexane-1,2'-indan)-4-ol(isomer A)-[27], having a melting point of 247° to 250° C.

Anal. Calcd. for $C_{16}H_{21}NO_2$: C, 74.10; H, 8.16; N, 5.40.

Found: C, 73.70; H, 8.19; N, 5.01.

On standing, there is obtained from the mother liquors 1.21 g. (32%) of 1'-acetamidospiro(cyclohexane1,2'-indan)-4-ol (isomer B)[27], having a melting point of 184° to 186° C.

Anal. Found: C, 73.91; H, 8.23; N, 5.30.

Following the procedure of Example 61B but substituting other 1'-acylamidospiro(cyclohexane-1,2'-indan)-4-ones[26], such as
1. 1'-propionylamidospiro(cyclohexane-1,2'-indan)-4-one[26],
2. 1'-isopropionylamido-5'-propylspiro(cyclohexane-1,2'-indan)-4-one[26], and the like, yields, respectively,
1. 1'-propionylamidospiro(cyclohexane-1,2'-indan)-4-ols[27],
2. 1'-isopropionylamido-5'-propylspiro(cyclohexane-1,2'-indan)-4-ols[27], and the like.

EXAMPLE 62B

1'-Acetamidospiro(cyclohexane-1,2'-indan)-4-ol methanesulfonate (isomer A)[28]

A mixture of 0.9 g. of 1'-acetamidospiro(cyclohexane-1,2'-indan-4-ol (isomer A) [27] (prepared in Example 61B) in 20 ml. of pyridine is warmed until all the solid has dissolved. There is then added 1 ml. of methane sulfonyl chloride. Follwoing about 4 hours of standing at room temperature, most of the solvent is removed under vacuum. The residue is then dissolved in water and methylene chloride, and the organic layer washed successively with water, 2.5 N hydrochloric acid, water and brine. The solution is evaporated to dryness and the residue recrystallized from acetone: Skellysolve B to give 0.72 g. of 1'-acetamidospiro(cyclohexane-1,2'-indan)-4-ol methanesulfonate (isomer A)[28], having a melting point of 137° to 139° C.

Anal. Calcd. for $C_{17}H_{23}NO_4S$: C, 60.51; H, 6,87; N, 4.15.

Found: C, 60.10; H, 6.85; N, 4.00.

EXAMPLE 63B

1'-Acetamidospiro(cyclohexane-1,2'-indan)-4-ol methanesulfonate (isomer B) [28]

To an ice cold solution of 1.21 g. of 1'-acetamidospiro(cyclohexane-1,2'-indan)-4-ol (isomer B) [27 ] (prepared in Example 61B) in 12 ml. of pyridine, 1.2 ml. of methane sulfonyl chloride is added. After about 5 hours in the cold the mixture is poured into ice: water. The solid that precipitates is recrystallized from acetone: Skellysolve B to give 1.21 g. of 1'-acetamidospiro(cyclohexane-1,2'-indan-4-ol methanesulfonate (isomer B) [28], melting at 161° to 163° C.

Anal. Calcd. for $C_{17}H_{23}NO_4S$: C, 60.61; H, 6.87; N, 4.15; M.W. 337.

Found: C, 60.40; H, 6.97; N, 4.21; m/e 337.

Following the procedures of Examples 62B and 63 but substituting other 1'-acylamidospiro(cyclohexane-1,2'-indan)-4-ols[27], such as 1'-propionylamido-5'-propoxyspiro(cyclohexane-1,2'-indan)-4-ol (isomer A) [27], yields, 1'-propionylamido-5'-propoxyspiro(cyclohexane-1,2'-indan)-4-ol methanesulfonate (isomer A)[28].

EXAMPLE 64B

1'-Acetamidospiro(cyclohexane-1,2'-indan)-4-amine hydrochloride[I(b)]

Following the procedure of Example 33B but substituting 1'-acetamidospiro(cyclohexane-1,2'-indan)-4-ol methanesulfonate[28] (prepared as in Examples 62B or 63B) as starting material, yields 1'-acetomidospiro(cyclohexane-1,2'-indan)-4-amine hydrochloride[I(b)].

Following the procedure of Example 64B but substituting other 1'-acylamidospiro(cyclohexane-1,2'-indan)-4-ol lower alkylsulfonates[28] as starting materials, such as
1. 1'-acetamido-4'-ethoxyspiro(cyclohexane-1,2'-indan)-4-ol ethanesulfonate[28],
2. 1'-isopropionylamido-5'-fluorospiro(cyclohexane-1,2'-indan)-4-ol propanesulfonate[28], and the like, yields, respectively,
1. 1'-acetamido-4'-ethoxyspiro(cyclohexane-1,2'-indan)-4-amine hydrochloride[I(b)],
2. 1'-isopropionylamido-5'-fluorospiro(cyclohexane-1,2'-indan)-4-amine hydrochloride[I(b)], and the like.

EXAMPLE 65B

1'-Acetamido-1-[spiro(cyclohexane-1,2'-indan)-4-yl]piperidine hydrochloride[I(b)]

Following the procedure of Example 36B but substituting 1'-acetamidospiro(cyclohexane-1,2'-indan)-4-amine hydrochloride[I(b)] (prepared as in Example 64B) as starting material, yields 1'-acetamido-1-[spiro(cyclohexane-1,2'-indan)-4-yl]piperidine hydrochloride[I(b)].

Following the procedure of Example 65B but substituting other 1'-acylamidospiro(cyclohexane-1,2'-indan)-4-amine acid addition salts [I(b)] and other dihaloalkanes in stoichiometrically appropriate amounts as starting materials, such as
1. 1'-acetamido-7'-ethylspiro(cyclohexane-1,2'-indan)-4-amine hydrochloride[I(b)]and 1,4-dibromobutane,
2. 5'-amino-1'-propionylamidospiro(cyclohexane-1,2'-indan)-4-amine hydrochloride[I(b)] and 1,5-diiodopentane, and the like, yields, respectively,
1. 1'-acetamido-1-[7'-ethylspiro(cyclohexane-1, 2'-indan)-4-yl] pyrrolidine hydrochloride] I(b)],
2. 1-[5'-amino-1'-propionylamidospiro(cyclohexane-1,2'-indan)-4-yl] piperidine hydrochloride [I(b)], and the like.

EXAMPLE 66B

4'-fluoro-4-[[1'-acetamidospiro[cyclohexane-1,2'-indan]-4-yl ]amino]butyrophenone hydrochloride[I(b)]

Following the procedure of Example 37B but substituting 1'-acetamidospiro(cyclohexane-1,2'-indan)-4-amine hydrochloride[I(b)] (prepared as in Example 64B) as starting material, yields 4'-fluoro-4[[1'-acetamidospiro[cyclohexane-1,2'-indan]-4-yl]amino]butyrophenone hydrochloride[I-(b)].

Following the procedure of Example 66B but substituting acid addition salts of other 1'-acylamidospiro(cyclohexane-1,2'-indan)-4-amines[I(b)] and other ω-haloalkanaryl ketones in stoichiometrically appropriate amounts, such as 1. 4'-chloro-1'-propionylamidospiro(cyclohexane-1,2'-indan)-4-amine hydrochloride[I(b)] and the 2,2-dimethyl-1,3-propanediol ketal of 3-chloro-4'-methyl propiophenone, 2. 5'-ethyl-1'-isopropionylamidospiro(cyclohexane-1,2'-indan)-4-amine hydrochloride[I(b)] and the 2,2-dimethyl-1,3-propanediol ketal of 4-chloro-3'-ethoxybutyrophenone, and the like, yields, respectively,
1. 4'-methyl-3-[[4'chloro-1'-propionylamidospiro[cyclohexane-1,2'-indan]-4-yl]amino]propiophenone hydrochloride[I(b)],
2. 3'-ethoxy 14-[[5'-ethyl-1'-isopropionylamidospiro[cyclohexane-1,2'-indan]-4-yl]amino]butyrophenone hydrochloride[I(b)], and the like.

EXAMPLE 67B

Ethyl 1'-acetamidospiro(cyclohexane-1,2'-indan)-4-carbamate[I(b)]

Following the procedures of Example 40B through 42B but substituting 1'-acetamidospiro(cyclohexane-1,2'-indan)-4-amine hydrochloride[I(b)] (prepared as in Example 64B) as starting material, yields ethyl 1-acetamidospiro(cyclohexane-1,2'-indan)-4-carbamate[I(b)].

Following the procedure of Example 67B but substituting acid addition salts of other 1'-acylamidospiro(cyclohexane-1,2'-indan)-4-amines and other lower alkyl haloformates as starting materials, such as
1. 5'-bromo-1'-propionylamidospiro(cyclohexane-1,2'-indan)-4-amine hydrochloride [I(b)] and propyl chloroformate,
2. 4'-amino-1'-isopropionylamidospiro(cyclohexane-1,2'indan)-4-amine hydrochloride[I(b)] and butyl chloroformate, and the like, yields, respectively,
1. propyl 5'-bromo-1'-propionylamidospiro(cyclohexane-1,2'-indan)-4-carbamate[I(b)],
2. butyl 4'-amino-1'-isopropionylamidospiro(cyclohexane-1,2'-indan)-4-carbamate[I(b)], and the like.

EXAMPLE 68B

1'-Acetamidospiro(cyclohexane-1,2'-indan)-4-methylamine hydrochloride[I(b)]

Following the procedure of Example 43B but substituting ethyl 1'-acetamidospiro(cyclohexane-1,2'-indan)-4-carbamate[I(b)] (prepared as in Example 67B) as starting material, yields 1'-acetamidospiro(-cyclohexane-1,2'-indan)-4-methylamine hydrochloride[I(b)].

Following the procedure of Example 68B but substituting other lower alkyl 1'-acylamidospiro(cyclohexane-1,2'-indan)-4-carbamates[I(b)] as starting materials, such as
1. propyl 4'-chloro-1'-propionylamidospiro(cyclohexane-1,2'-indan)-4-carbamate[I(b)],
2. butyl 5'-ethylamino-1'-isopropionylamidospiro(cyclohexane-1,2'-indan)-4-carbamate[I(b)], and the like, yields, respectively,
1. 4'-chloro-1'-propionylamidospiro(cyclohexane-1,2'-indan)-4-methylamine hydrochloride[I(b)],
2. 5'-ethylamino-1'-isopropionylamidospiro(cyclohexane-1,2'-indan)-4-methylamine chloride[I(b)], and the like.

EXAMPLE 69B

4'-fluoro-4[methyl[1'-acetamidospiro[cyclohexane-1,2'-indan]-4-yl]amino]butyrophenone hydrochloride[I(b)]

Following the procedure of Example 46B but substituting 1'-acetamidospiro(cyclohexane-1,2'-indan)-4-methylamine hydrochloride[I(b)] (prepared as in Example 68B) as starting material, yields 4'-fluoro-4-[methyl[1'-acetamidospiro[cyclohexane-1,2'-indan]-4-yl]amino]butyrophenone hydrochloride[I(b)].

Following the procedure of Example 69B but substituting acid addition salts of other 1'-acylamidospiro[cyclohexane-1,2'-indan]-4-lower alkylamines-[I(b)] and the 2,2-dimethyl-1,3-propanediol ketals of other ω-haloalkanaryl ketones in stoichiometrically appropriate amounts as starting materials, such as
1. 6'-ethoxy-1'-propionylamidospiro(cyclohexane-1,2'-indan)-4-methylamine hydrochloride [I(b)] and the 2,2-dimethyl-1,3-propanediol ketal of 3'-bromo-3-chloropropiophenone,
2. 5'-amino-1'-isopropionylamidospiro(cyclohexane-1,2'-indan)-4-methylamine hydrochloride[I(b)] and the 2,2-dimethyl-1,3-propanediol ketal of 5-chloro-2'-propoxyvalerophenone, and the like, yields, respectively,
1. 3'-bromo-3-[methyl[6'-ethoxy-1'-propionylamidospiro[cyclohexane-1,2'-indan]-4-yl]amino]propiophenone hydrochloride[I(b)],
2. 2'-propoxy-5-[methyl[5'-amino-1'-isopropionyl-amidospiro[cyclohexane-1,2'-indan]-4-yl]amino]valerophenone hydrochloride[I(b)], and the like.

EXAMPLE 70B

5'-Nitrospiro(cyclohexane-1,2'-indan)-4-one[29]

To an ice cooled solution of 9.04 g. (0.045 M) of spiro(cyclohexane-1,2'-indan)-4-one[11] [prepared as in (a) of Example 24B] in 45 ml. of trifluoroacetic acid, 9 ml. of nitric acid is added. After reaction in the cold for about 2 hours, the solution is poured onto ice: water. The precipitated solid is chromatographed on 1 l. of silica gel and eluted with 25% acetone: Skellysolve B. The crystalline fractions obtained are combined and recrystallized from acetone: Skellysolve B to give 7.23 g. (65% yield) of 5'-nitrospiro(cyclohexane-1,2'-indan)-4-one[29] having a melting point of 124° to 128° C. The analytical sample melted at 126° to 127.5° C.

Anal. Calcd. for $C_{14}H_{15}NO_3$: C, 68.55; H, 6.16; N, 5.71.

Found: C, 68.38; H, 6.24; N, 5.95.

EXAMPLE 71B

5'-Acetamidospiro(cyclohexane-1,2'-indan)-4-one[31]

1. A suspension of 0.5 g. of palladium on carbon catalyst in a solution of 7.89 g. (0.32 M) of 5'-nitrospiro(cyclohexane-1,2'-indan)-4-one[29] (obtained as in Example 70B) in 150 ml. of ethyl acetate is shaken under hydrogen. After about 3 hours of shaking an additional 0.5 g. of the same catalyst is added and shaking continued. When the theoretical uptake of hydrogen is observed, the catalyst is removed by filtration and a solution of 6.1 g. of p-toluenesulfonic acid in a small volume of methanol is added. The solvent is removed under vacuum and recrystallization from methanol: acetone attempted, but the ocurrence, on standing in the cold for about 65 hours, of extensive decomposition, is apparent. The material is converted to the free base, 5′-aminospiro(cyclohexane-1,2′indan)-4-one[30].

2. A solution of the product [30], obtained in (1), above, in 40 ml. of pyridine is treated with 10 ml. of acetic anhydride. After about 5 hours the mixture is poured onto ice: water and the resulting precipitate extracted with methylene chloride. This solution is washed successively with water, 2.5 N hydrochloric acid, water and brine and then evaporated to dryness. The residue is chromatographed on a column of 700 ml. of silica and eluted with 25% acetone: methylene chloride. The crystalline fractions are combined and recrystallized from methanol to give 3.15 g. (38%) of 5′-acetamidospiro(cyclohexane-1,2′-indan)-4-one[31], melting at 169° to 171° C.

Anal. Calcd. for $C_{16}H_{19}NO_2$: C, 74.68; H, 7.44; N, 5.44; M.W. 257.

Found: C, 74.36; H, 7.54; N, 5.48; m/e 257.

Following the procedure of Example 71B but substituting other 5′-nitrospiro(cyclohexane-1,2′-indan)-4-one-[29] and other anhydrides of hydrocarbon carboxylic acids as starting materials, such as 6′-ethoxy-5′-nitrospiro(cyclohexane-1,2′-indan)-4-one[29]and propionic anhydride, yields,
6′-ethoxy-5′-propionamidospiro(cyclohexane-1,2′indan)-4-one[31].

EXAMPLE 72B

5′-Acetamidospiro(cyclohexane-1,2′-indan)-4-ol methanesulfonate[33]

1. To 3.15 g (0.012 M) of 5′-acetamidospiro(cyclohexane-1,2′-indan)-4-one[31] (obtained in Example 71B) dissolved in 50 ml. of 95% isopropanol with warming on a steam bath, 0.5 g. of sodium borohydride is added. After about 4 hours of standing at room temperature, the solvent is removed under vacuum. The residue is dissolved in methylene chloride and water. The organic layer is washed with water and brine and then evaporated to dryness to give 3.03 g. of 5′-acetamidospiro(cyclohexane-1,2′-indan4-ol[32], having a melting point of 148° to 152° C.

2. A solution of the product [32], obtained in (1), above, in 30 ml. of pyridine is cooled in ice and 3 ml. methanesulfonyl chloride added. After about 5 hours in the cold, the mixture is poured onto ice: water and extracted with methylene chloride. The solution is washed successively with water, 2.5 N hydrochloric acid, water and brine and evaporated to dryness. The residue is chromatographed on a column of 300 ml. of Florisil and eluted with 25% acetone: Skellysolve B. The crystalline fractions are combined and recrystallized from ethyl acetate: cyclohexane. There is obtained 1 g. (25%) of 5′-acetamidospiro(cyclohexane-1,2′-indan)-4-ol methanesulfonate[33] having a melting point of 145° to 147° C., and a second crop of 0.2 g. (5%) melting at 143° to 145° C.

Anal. Calcd. for $C_{17}H_{23}NO_4S$: C, 60.51; H, 6.87; N, 4.15.

Found: C, 60.52; H, 7.00; N, 4.10.

Following the procedure of Example 72B but substituting other 5′-acylamidospiro(cyclohexane-1,2′-indan)-4-ones[31], such as 4′-fluoro-5′-propionamidospiro(cyclohexane-1,2′indan)-4-one[31], yields, 4′-fluoro-5′-propionamidospiro(cyclohexane-1,2′indan-4-ol methanesulfonate[33].

EXAMPLE 73B

5′-Acetamidospiro(cyclohexane-1,2′-indan)-4-amine hydrochloride[I(b)]

1. A mixture of 1.2 g. (0.0036 M) of 5′-acetamidospiro(cyclohexane-1,2′-indan)-4-ol methanesulfonate[33] (obtained in Example 72B) and 1.2 g. of sodium azide in 10 ml. of dimethylformamide is stirred for about 20 hours in an oil bath at about 90° C. The solvent is then removed under vacuum and the residue partitioned between water and benzene. The organic layer is washed with water and brine and then evaporated to dryness to give 5′-acetamidospiro(cyclohexane-1,2′-indan)-4-ylazide[34].

2. A solution of the residue[34], obtained in (1), above, in 150 ml. of ethyl acetate is shaken under hydrogen in the presence of 0.15 g. of 10% palladium on carbon catalyst. the catalyst is collected on a filter and the filtrate evaporated to dryness. The residue is dissolved in methanol and treated with 6 N hydrochloric acid in ether. This solution is evaporated to dryness and recrystallized from methanol: ethyl acetate, to give 0.67 g. (63% yield) of 5′-acetamidospiro(cyclohexane-1,2′-indan)-4-amine hydrochloride[I(b)], also named N-[4-aminospiro[cyclohexane1,2′-indan]-5′-yl]acetamide hydrochloride, melting at 270° to 275° C. (with decomposition).

Anal. Calcd. for $C_{16}H_{23}ClN_2O \cdot \frac{1}{2}H_2O$: C, 63.24; H, 7.96; N, 9.22; M.W. (free base) 258.

Found: C, 62.80; H, 8.04; N, 8.72; m/e 258.

Following the procedure of Example 73B but substituting other 5′-acylamidospiro(cyclohexane-1,2′-indan)-4-ol methanesulfonates[33] as starting materials, such as 1. 6′-ethyl-5′-propionamidospiro(cyclohexane-1,2′indan)-4-ol methanesulfonate[33],
2. 7′-bromo-5′-isopropionamidospiro(cyclohexane1,2′-indan)-4-ol methanesulfonate[33], and the like, yields, respectively, 1. 6′-ethyl-5′-propionamidospiro(cyclohexane-1,2′indan)-4-amine hydrochloride[I(b)],
2. 7′-bromo-5′-isopropionamidospiro(cyclohexane-1,2′-indan)-4-amine hydrochloride[I(b)], and the like.

EXAMPLE 74B

5′-Acetamido-1-1-[spiro(cyclohexane-1,2′-indan)-4-yl]piperidine hydrochloride[I(b)]

Following the procedure of Example 36B but substituting 5′-acetamidospiro(cyclohexane-1,2′-indan)-4-amine hydrochloride[I(b)] (prepared as in Example 73B) as starting material, yields 5′-acetamido-1-[spiro(cyclohexane-1,2′-indan)-4-yl]piperidine hydrochloride[I(b)].

Following the procedure of Example 74B but substituting other 5′-acylamido(cyclohexane-1,2′-indan)-4-amine acid addition salts[I(b)] and other dihaloalkanes in stoichiometrically appropriate amounts as starting materials, such as 5′-acetamido-7′-ethoxyspiro(cyclohexane-1,2′-indan)-4-amine hydrochloride[I(b)] and 1,4-diiodobutane, and the like,
yields,
5′-acetamido-1-[7′-ethoxyspiro(cyclohexane-1,2′-indan)-4-yl]pyrrolidine hydrochloride[I(b)], and the like.

EXAMPLE 75B

4′-Fluoro-4-[[5′-acetamidospiro[cyclohexane-1,2′-indan]-4-yl]amino]butyrophenone hydrochloride[I(b)]

Following the procedure of Example 37B but substituting 5′-acetamidospiro(cyclohexane-1,2′-indan)-4-amine hydrochloride[I(b)] (prepared as in Example 73B) as starting material, yields 4′-fluoro-4-[[5′-acetamidospiro[cyclohexane-1,2′-indan]-4-yl]amino]butyrophenone hydrochloride [I(b)].

Following the procedure of Example 75B but substituting acid addition salts of other 5′-acylamidospiro(cyclohexane-1,2′-indan)-4-amines[I(b)] and other ω-haloalkanaryl ketones in stoichiometrically appropriate amounts, such as 6′-ethyl-5′-isopropionylamidospiro(cyclohexane-1,2′-indan)-4-amine hydrochloride [I(b)] and the 2,2-dimethyl-1,3-propanediol ketal of 4-chloro-3′-ethoxybutyrophenone, yields,
3′-ethoxy-4-[[6′-ethyl-5′-isopropionylamidospiro[cyclohexane-1,2′-indan]4-yl]amino]-butyrophenone hydrochloride[I(b)].

EXAMPLE 76B

Ethyl 5′-acetamidospiro(cyclohexane-1,2′-indan)-4-carbamate[I(b)]

Following the procedure of Example 40B but substituting 5′-acetamidospiro(cyclohexane-1,2′-indan)-4-amine hydrochloride[I(b)] (prepared as in Example 73B) as starting material, yields ethyl 5′-acetamidospiro(cyclohexane-1,2′-indan)-4-carbamate[I(b)].

Following the procedure of Example 76B but substituting acid addition salts of other 5′-acylamidospiro(cyclohdexane-1,2′-indan)-4-amines and other lower alkyl haloformates as starting materials, such as 4′-propyl-5′-propionylamidospiro(cyclohexane-1,2′-indan)-4-amine hydrochloride[I(b)] and propyl chloroformate, yields,
propyl 4′-propyl-5′-propionylamidospiro(cyclohexane-1,2′-indan)-4-carbamate[I(b)].

EXAMPLE 77B

5′-Acetamidospiro(cyclohexane-1,2′indan)-4-methylamine hydrochloride[I(b)]

Following the procedure of Example 43B but substituting ethyl 5′-acetamidospiro(cyclohexane-1,2′-indan)-4-carbamate [I(b)] (prepared as in Example 76B) as starting material, gives 5′-acetamidospiro(-cyclohexane-1,2′-indan)4-methylamine hydrochloride[I(b)].

Following the procedure of Example 77B but substituting other lower alkyl 5′-acylamidospiro(cyclohexane-1,2′-indan)-4-carbamates[I(b)] as starting materials, such as butyl 7′-ethoxy-5′-isopropionylamidospiro(cyclohexane-1,2′-indan)-4-carbamate[I(b)], and the like, yields,
7′-ethoxy-5′-isopropionylamidospiro(cyclohexane1,2′-indan)-4-propylamine hydrochloride[I(b)], and the like.

EXAMPLE 78B

4′-Fluoro-4-[methyl[5′-acetamidospiro[cyclohexane-1,2′-indan]-4-yl]amino]butyrophenone hydrochloride[I(b)]

Following the procedure of Example 46B but substituting 5′-acetamidospiro(cyclohexane-1,2′-indan)-4-methylamine hydrochloride[I(b)] (prepared as in Example 77B) as starting material, yields 4′-fluoro-4-[methyl[5′-acetamidospiro[cyclohexane-1,2′-indan]4-yl]amino]butyrophenone hydrochloride [I(b)].

EXAMPLE 79B 4-hydroxy-α-methylspiro(cyclohexane-1,2′-indan)-4-acetic acid[36]

1. A chip of iodine is added to a well stirred mixture of 5.87 g.(0.029 M) of spiro(cyclohexane-1,2′-indan)-4-one [11] ]prepared as in (1) of Example 24B], 6 g. of the known compound methyl α-bromopropionate and 4 g. of zinc wool, and the reaction started by heating the mixture of reflux. After about 6 hours the mixture is allowed to cool, the excess metal separated on a filter, and the filtrate washed successively with 2.5 N hydrochloric acid, water and brine and then evaporated to dryness. The residue is chromatographed on a column of 800 ml. of silica gel and eluted with 5% acetone: Skellysolve B. The fractions similar by thin layer chromatography are combined to give 4-hydroxy-α-methylspiro(cyclohexane-1,2′-indan)-4-acetate[35] as an oil.

2. A mixture of the oily ester [35], obtained in (1), above, 10 ml. of 50% aqueous sodium hydroxide solution and 10 ml. of water in 100 ml. of methanol, is stirred with heating at reflux for about 17 hours. The solvent is then removed under vacuum. A suspension of the residue in water and ether is made strongly acidic, the organic layer washed with brine and water and then evaporated to dryness. The residual solid is recrystallized from ether: Skellysolve B to give 3.98 g. (50%) of 4-hydroxy-α-methylspiro(cyclohexane-1,2′-indan)-4-acetic acid-[36], melting at 111° to 114° C.

Anal. Calcd. for $C_{17}H_{22}O_3$: C, 74.48; H, 8.30.
Found: C, 74.42; H, 8.08.

EXAMPLE 80B

Sprio(cyclohexane-1,240 -indan)-$\Delta^{4,\alpha}$ -acetic acid [38]

1. To 4.02 g. of triethylphosphono acetate in 50 ml. of tetrahydrofuran, 0.84 g. of 56% sodium hydride (in mineral oil) is added. After about 10 minutes, 3.59 g. (0.018 M) of spiro(cyclohexane-1,2-′-indan)-4-one[11] [prepared as in (1) of Example 24B] in 50 ml. of tetrahydrofuran, is added. The mixture is heated at reflux for about 3 hours and allowed to cool. After standing at room temperature for about 17 hours, 100 ml. of 2.5 N hydrochloric acid is added. The organic layer is separated, washed with water and brine and evaporated to dryness to give spiro(cyclohexane-1,2′-indan)-$\Delta^{4,\alpha}$-acetate [37].

2. A mixture of the residual gum [36], obtained in (1), above, 6 ml. of 50% aqueous sodium hydroxide solution and 10 ml. of water in 100 ml. of methanol is heated at reflux for about 5 hours. The methanol is then removed under vacuum, the resulting residue diluted with water and acidified, and the precipitate that forms extracted with ether. The organic layer is washed with water and brine and evaporated to dryness. The residue is recrystallized twice from acetone: Skellysolve B to give 2.67 g. (61% yield) of spiro(cyclohexane-1,2'-indan)-$\Delta^{4,\alpha}$-acetic acid[38], melting at 119° to 121°C.

Anal. Calcd. for $C_{16}H_{18}O_2$: C, 79.31; H, 7.49.
Found: C, 79.38; H, 7.70.

EXAMPLE 81B spiro(cyclohexane-1,2'-indan)acetic acid[39] A mixture of 1.67 g. (0.0069 M) of spiro(cyclohexane-1,2'-indan)-$\Delta^{4,\alpha}$-acetic acid [38] (prepared as in Example 80B) and 0.15 g. of Adams catalyst is shaken under hydrogen until the theoretical uptake is observed (about 25 hours). The catalyst is removed by filtration and the filtrate evaporated to dryness. The residue is recrystallized from ether: Skellysolve B to give 1.48 g. (88%) of spiro(cyclohexane-1,2'-indan)acetic acid[39] having a melting point of 134° to 137°C.

Anal. Calcd. for $C_{16}H_{20}O_2$: C, 78.65; H, 8.25.
Found: C, 78.50; H, 8.17.

EXAMPLE 82B

1'-Hydroxy-1'-methylspiro(cyclohexane-1,2'indan)-4-one ethylene ketal [40]

A solution of 5 g. (0.019 M) of spiro(cyclohexane-1,2'-indan)-1',4-dione 4-ethylene ketal [9] (prepared as in Example 16B) in 60 ml. of tetrahydrofuran is added to 67 ml. of 3M methyl magnesium bromide in ether. After standing for about 17 hours at room temperature, the mixture is cooled in ice and treated cautiously with 50 ml. of saturated ammonium chloride. The organic layer is separated, diluted with benzene and washed with water and brine. The solution is evaporated to dryness and recrystallized from methylene chloride: cyclohexane to give 3.7 g. (71%) of 1'-hydroxy-1'-methylspiro(cyclohexane-1,2'-indan)-4-one ethylene ketal [40], melting at 140° to 143°C.

Anal. Calcd for $C_{17}H_{22}O_3$: C, 74.47; H, 8.08.
Found: C, 74.21; H, 8.09.

Following the procedure of Example 82B but substituting other spiro(cyclohexane-1,2'-indan)-1',4-dione 4-ethylene ketals[9] as starting materials, such as
4'-ethoxyspiro(cyclohexane-1,2'-indan)-1',4-dione ethylene ketal[9] yields,
4'-ethoxy-1'-hydroxy-1'-methylspiro(cyclohexane-1,2'-indan)-4-one ethylene ketal-[40].

EXAMPLE 83B

1'-Exo-methylenespiro(cyclohexane-1,2'-indan)-4-one [41]

A solution of 9.82 g.(0.036 M) of 1'-hydroxy-1'-methylspiro(cyclohexane-1,2'-indan)-4-one ethylene ketal [40](prepared as in Example 82B) and 25 ml. of 2.5 N hydrochloric acid in 250 ml. of acetone is stirred at room temperature for about 17 hours. The solvent is then removed under vacuum and the residue dissolved in ether and water. The organic layer is washed with water and brine and evaporated to dryness. The residue is recrystallized from petroleum ether to give 5.12 g. (67%) of 1'-exomethylenespiro(cyclohexane-1,2'-indan)-4-one[41], having a melting point of 60° to 62°C. The NMR spectrum of this compound is in agreement with its expected structure.

Following the procedure of Example 83B but substituting other 1'-hydroxy-1'-methylspiro(cyclohexane-1,2'-indan)-4-one ethylene ketals[40] as starting materials, such as
6'-chloro-1'-hydroxy-1'-methylspiro(cyclohexane-1,2'-indan)-4-one ethylene ketal[40], yields,
6'-chloro-1'-exo-methylenespiro(cyclohexane-1,2'indan)-4-one[41].

EXAMPLE 84B

1'-Exo-methylenespiro(cyclohexane-1,2'-indan)-4-ol[42]

A mixture of 2.17 g. (0.010 M) of 1'-exo-methylenespiro(cyclohexane-1,2'-indan)-4-one[41] (prepared as in Example 83B) and 0.75 g. of sodium borohydride in 40 ml. of isopropanol is stirred at room temperature for about 6 hours. The solvent is removed under vacuum and the residue dissolved in water and ether. The organic layer is washed with water and brine and evaporated to dryness. The residue is chromatographed on a column of 250 ml. of silica gel and eluted with 20% acetone: Skellysolve B. There is obtained 0.08 g. of solid, having a melting point of 65° to 69° C. and an NMR spectrum in agreement with the structure of a compound having its hydroxy substituent in the axial position, namely, 1'-exo-methylenespiro(cyclohexane-1,2'-indan)-4-trans-ol[42]. This is followed by a gum that crystallizes only in the presence of water, giving 1.71 g. (78% yield) of product melting at 57° to 61° C. and an NMR spectrum in agreement with the structure of a compound having its hydroxy substituent in the equatorial position, namely, 1'-exo-methylenespiro(cyclohexane-1,2'-indan)-4-cis-ol[42].

Following the procedure of Example 84B but substituting other 1'-exo-methylenespiro(cyclohexane-1,2'-indan)-4-ones [41] as starting materials, such as
1. 4'-chloro-1'-exo-methylenespiro(cyclohexane-1,2'-indan)-4-one[41],
2. 5'-ethoxy-1'-exo-methylenespiro(cyclohexane-1,2'-indan)-4-one[41], and the like, yields, respectively,
1. trans and cis 4'-chloro-1'-exo-methylenespiro(cyclohexane-1,2'-indan)-4-ol[42],
2. trans and cis 5'-ethoxy-1'-exo-methylenespiro(cyclohexane-1,2'-indan)-4-ol[42], and the like.

EXAMPLE 85B

1'-Exo-methylenespiro(cyclohexane-1,2'-indan)-4-ol methanesulfonate [43]

To an ice cold solution of 4.26 g. (0.020 M) of 1'-exo-methylenespiro(cyclohexane-1,2'-indan)-4-ol[42] (prepared as in Example 84β) in 40 ml. of pyridine, 4.3 ml. of methanesulfonyl chloride is added. After about 7 hours the mixture is poured into ice: water. The gum that precipitates is extracted with ether and the organic layer washed successively with water, 2.5 N hydrochloric acid, water and brine, then evaporated to dryness. The residue is recrystallized from a small amount of methanol to give 4.82 g. (83%) of 1'-exo-methylenespiro(cyclohexane-1,2'-indan)-4-ol methanesulfonate [43], have a melting point of 72° to 74° C.

Anal. Calcd. for $C_{16}H_{20}O_3S$: C, 65.72; H, 6.89; M.W. 292.

Found: C, 65.12; H, 7.12; m/e 292.

Following the procedure of Example 85B but substituting other 1'-exo-methylenespiro(cyclohexane-1,2'-indan)4-ols[42] as starting materials, such as
7'-bromo-1'-exo-methylenespiro(cyclohexane-1,2'-indan)-4-ol[42], yields,
7′-bromo-1′-exo-methylenespiro(cyclohexane-1,2′-indan)-4-ol methanesulfonate [43].

EXAMPLE 86B

1′-Exo-methylenespiro(cyclohexane-1,2′-indan)-4-amine hydrochloride [I(b)]

A mixture of 5.65 g. (0.019 M) of 1′-exo-methylenespiro(cyclohexane-1,2′-indan)-4-ol methanesulfonate [43] (prepared as in Example 85B) and 5.65 g. of sodium azide is heated for about 17 hours in an oil bath at about 90° C. The solvent is removed under vacuum and the residue dissolved in benzene and water. The organic layer is washed with water and brine evaporated to dryness to give 1′-exo-methylenespiro(cyclohexane-1,2′-indan)-4-ylazide[44]. The residue [44] in 80 ml. of tetrahydrofuran is added to 0.75 g. of lithium aluminum hydride in 10 ml. of tetrahydrofuran. After about 5 hours at room temperature the mixture is cooled in ice and treated successively with 0.75 ml. of water, 0.75 ml. of water, 0.75 ml. of 15% aqueous sodium hydroxide solution and 2.25 ml. of water. The inorganic gel is collected on a filter and the filtrate evaporated to dryness. An ether solution of the residue is treated with 6 N hydrogen chloride in ether. The precipitated salt is recrystallized from methylene chloride to give 3.08 g. (61%) of 1′-exo-methylenespiro(cyclohexane-1,2′-indan)-4-amine hydrochloride[I(b)], having a melting point of 250° to 253° C.

Anal. Calcd. for $C_{15}H_{20}ClN \cdot H_2O$: C, 67.29; H, 8.29; N, 5.23.

Found: C, 67.50; H, 7.92; N, 5.21.

Following the procedure of Example 86B but substituting other 1′-exo-methylenespiro(cyclohexane-1,2′-indan)4-ol methanesulfonates [43] as starting materials, such as 5′-ethoxy-1′-exo-methylenespiro(cyclohexane-1,2′-indan)-4-ol methanesulfonate [I(b)], yields,
5′-ethoxy-1′-exo-methylenespiro(cyclohexane-1,2′-indan)-4-amine hydrochloride [I(b)].

EXAMPLE 87B

1-[1′-Methylenespiro(cyclohexane-1,2′-indan)-4-yl]piperidine [I(b)]

The amine prepared from 1.41 g. (0.0056 M) of 1′-exo-methylenespiro(cyclohexane-1,2′-indan)-4-amine hydrochloride [I(b)], 1,81 g. of 1,5-diiodopentane and 1.55 g. of potassium carbonate in 15 ml. of ethanol is stirred at reflux temperature for about 18 hours. The mixture is allowed to cool, diluted with water and the solid collected on a filter. The solid is recrystallized from methanol to give 1.05 g. (67% yield) of 1-[1′-methylenespiro(cyclohexane-1,2′-indan)-4-yl]piperidine [I(b)], also named 1′-exo-methylenespiro(cyclohexane-1,2′-indan)piperidine, having a melting point of 93° to 95° C.

Anal. Calcd. for $C_{20}H_{27}N$: C, 85,35; H, 9.67; N, 4.90.
Found: C, 85.58; H, 9.99; N, 5.24.

Following the procedure of Example 87B but substituting other 1′-exo-methylenespiro(cyclohexane-1,2′-indan)-4-amine acid addition salts [I(b)]and other dihaloalkanes in stoichiometrically appropriate amounts as starting materials, such as 5′-chloro-1′-exo-methylenespiro(cyclohexane-1,2′-indan)-4-amine hydrochloride[I(b)] and 1,6-dibromohexane, yields,
1-[5′-chloro-1′-methylenespiro(cyclohexane-1,2′-indan)-4-yl] hexamethyleneimine hydrochloride [I(b)].

EXAMPLE 88B

4′-Fluoro-4-[[1′-methylenespiro(cyclohexane-1,2′-indan)-4-yl]amino]butyrophenone hydrochloride [I(b)]

A mixture of the free base obtained from 2 g. (0.0080 M) of 1′-exo-methylenespiro(cyclohexane-1,2′-indan)-4-amine hydrochloride [I(b)] (prepared as in Example 86B), 1.6 g. of potassium iodide, 2.49 g. of potassium carbonate and 2.32 g. of the 2,2-dimethyl-1,3-propanediol ketal of 4-chloro-4′-fluorobutyrophenone in 40 ml. of dimethylformamide is stirred in an oil bath at about 90° C. for about 18 hours. The solvent is then removed under vacuum and the residue dissolved in benzene and water. The organic layer is washed with water and brine and evaporated to dryness. The residue is stirred with 15 ml. of 2.5 N hydrochloric acid and 30 ml. of methanol for about 3 hours. The methanol is then removed and the solid collected on a filter. This material is recrystallized from methanol: ethyl acetate to give 0.95 g. (29%) of 4′-fluoro-4-[[1′-methylenespiro(cyclohexane-1,2′-indan)-4-yl]amino]butyrophenone hydrochloride [I(b)], having a melting point of 208° to 211° C.

Anal. Calcd. for $C_{25}H_{29}ClFNO$: C, 72.53; H, 7.06; N, 3.38.

Found: C, 72.20; H, 7.19; N, 3.68.

Following the procedure of Example 88B but substituting acid addition salts of other 1′-exo-methylenespiro(cyclohexane-1,2′-indan)-4-amines [I(b)] and other ω-haloalkanaryl ketones in stoichiometrically appropriate amounts, such as 4′-chloro-1′-exo-methylenespiro(cyclohexane-1,2′-indan)-4-amine hydrochloride [I(b)] and the 2,2-dimethyl-1,3-propanediol ketal of 3-chloro-4′-methylpropiophenone, yields.
4′-methyl-3-[[4′-chloro-1′-exo-methylenespiro(cyclohexane-1,2′-indan)-4-yl]amino]propionphenone hydrochloride [I(b)].

EXAMPLE 89B

Ethyl 1′-exo-methylenespiro(cyclohexane-1,2′-indan)-4-carbamate [I(b)]

Following the procedure of Example 40B but substituting 1′-exo-methylenespiro(cyclohexane-1,2′-indan)-4-amine hydrochloride [I(b)] (prepared as in Example 86B) as starting material, yields, ethyl-1′-exo-methylenespiro(cyclohexane-1,2′-indan)-4-carbamate [I(b)].

Following the procedure of Example 89B but substituting acid addition salts of other 1′-exo-methylenespiro(cyclohexane-1,2′-indan)-4-amines [I(b)] and other lower alkyl haloformates, such as 6′-chloro-1′-exo-methylenespiro(cyclohexane-1,2′-indan)-4-amine hydrochloride [I(b)] and butyl chloroformate, yields,
butyl 6′-chloro-1′-exo-methylenespiro(cyclohexane1,2′-indan)-4-carbamate [I(b)].

EXAMPLE 90B

1′-Exo-methylenespiro(cyclohexane-1,2′-indan)-4-methylamine hydrochloride [I(b)]

Following the procedure of Example 43B but substituting ethyl 1′-exo-methylenespiro(cyclohexane-1,2′-indan)-4-carbamate [I(b)] (prepared as in Example 89B) as starting material, yields 1′-exo-methylenespiro(cyclohexane-1,2′-indan)-4-methylamine hydrochloride [I(b)].

Following the procedure of Example 90B but substituting other lower alkyl 1′-exo-methylenespiro(cyclohexane-1,2′-indan)-4-carbamates [I(b)] as starting materials, such as butyl   5′-ethoxy-1′-exo-methylenespiro(cyclohexane1,2′-indan)-4-carbamate [I(b)], yields, 5′-ethoxy-1′-exo-methylenespiro(cyclohexane-1,2′-indan)-4-methylamine hydrochloride [I(b)], and the like.

EXAMPLE 91B

4′-Fluoro-4-[methyl[1′-exo-methylenespiro(cyclohexane-1,2′-indan)-4-yl]amino]butyrophenone hydrochloride [I(b)]

Following the procedure of Example 46B but substituting 1′-exo-methylenespiro(cyclohexane-1,2′-indan)-4-methyl-amine hydrochloride [I(b)] (prepared as in Example 90B) as starting material, yields 4′-fluoro-4-[methyl[1′-exo-methylenespiro(cyclohexane-1,2′-indan)-4-yl]amino]butyrophenone hydrochloride [I(b)].

Following the procedure of Example 91B but substituting acid addition salts of other 1′-exo-methylenespiro(cyclohexane-1,2′-indan)-4-lower alkylamines [I(b)] and the 2,2-dimethyl-1,3-propanediol ketals of other ω-haloalkanaryl ketones in stoichiometrically appropriate amounts, such as 7′-bromo-1′-exo-methylenespiro(cyclohexane-1,2′-indan)-4-methylamine hydrochloride [I(b)] and the 2,2-dimethyl-1,3-propanediol ketal of 5-chloro-4′-propylvalerophenone, yields, 4′-propyl-5-[methyl[7′-bromo-1′-exo-methylenespiro(cyclohexane-1,2′-indan)-4-yl]amino]-valerophenone hydrochloride [I(b)].

EXAMPLE 1C

4-Benzyl-4-hydroxymethylcyclohexan-1-one ethylene ketal(1)

A solution of 22.3 g. (0.77 M) of 4-benzyl-4-carbomethoxy-1-cyclohexaneone ethylene ketal [5] (prepared as in Example 4B) in 220 ml. of tetrahydrofuran is added to 3 g. of lithium aluminum hydride in 30 ml. of tetrahydrofuran. The mixture is stirred at reflux temperature for about 5.5 hours and then cooled in ice. There is added successively 3 ml. of water, 3 ml. of aqueous 15% sodium hydroxide solution and 9 ml. of water. The inorganic gel is collected on a filter and the filtrate evaporated to dryness. The residue is recrystallized from methylene chloride: Skellysolve B to give 18.8 g. (93% yield) of 4-benzyl-4-hydroxymethylcyclohexan-1-one ethylene ketal (1), having a melting point of 76° to 78° C.

Anal. Calcd. for $C_{16}H_{22}O_3$: C, 73.25; H, 8.45.

Found: C, 73.08; H, 8.65.

Following the procedure of Example 1C but substituting other 4-benzyl-4-carbomethoxy-1-cyclohexanone ethylene ketals [5] as starting materials, such as 1. 4-(p-methylbenzyl)-4-carbomethoxy-1-cyclohexane ethylene ketal [5], 2. 4-(m-methoxybenzyl)-4-carbomethoxy-1-cyclohexane ethylene ketal [5], and the like, yields respectively, 1. 4-(p-methylbenzyl)-4-hydroxymethylcyclohexan-1-one ethylene ketal (1), 2. 4-(m-methoxybenzyl)-4-hydroxymethylcyclohexan-1-one ethylene ketal (1), and the like.

EXAMPLE 2C

4-Benzyl-4-hydroxymethylcyclohexan-1-one ethylene ketal methanesulfonate (2)

To an ice cold solution of 4-benzyl-4-hydroxymethylcyclohexan-1-one ethylene ketal (1) (prepared in Example 1C) in 100 ml. of pyridine, 19 ml. of methanesulfonyl chloride is added. After standing in the cold for about 5.5 hours, the mixture is poured into ice: water. The gum that precipitates is extracted with ether. The organic layer is washed successively with water, ice cold 2.5 N hydrochloric acid, water, saturated aqueous sodium bicarbonate solution and brine, and then evaporated to dryness. The residual solid is recrystallized from methylene chloride: Skellysolve B to give 21.1 g. (86%) of 4-benzyl-4-hydroxymethylcyclohexan-1-one ethylene ketal methanesulfonate (2).

Following the procedure of Example 2C but substituting other 4-benzyl-4-hydroxymethylcyclohexan-1-one ethylene ketals (1) as starting materials, such as 1. 4-(p-ethoxybenzyl)-4-hydroxymethylcyclohexan-1-one ethylene ketal (1), 2. 4-(m-propionylamidobenzyl)-4-hydroxymethylcyclohexan-1-ethylene ketal (1), and the like, yields, respectively, 1. 4-(p-ethoxybenzyl)-4-hydroxymethylcyclohexan-1-one ethylene ketal methanesulfonate (2), 2. 4-(m-propionylamidobenzyl)-4-hydroxymethylcyclohexan-1-one ethylene ketal methanesulfonate (2), and the like.

EXAMPLE 3C

4-Benzylcyclohexan-4-acetic acid-1-one ethylene ketal (4)

1. A mixture of 18.6 g. (0.055 M) of 4-benzyl-4-hydroxymethylcyclohexan-1-one ethylene ketal methanesulfonate (2) (prepared as in Example 2C) and 18 g. of potassium cyanide in 180 ml. of hexamethylphosphoramide is heated for about 17 hours in an oil bath at about 145° C. The resulting gel is allowed to cool, diluted to 800 ml. with water and extracted with benzene. The organic layer is washed with water and brine and evaporated to dryness. The residue is chromatographed on 1 l. of silica gel and eluted with 25% ethyl acetate in Skellysolve B and the fractions found similar to TLC pooled to give 4-benzyl-4-cyanocyclohexan-1-one ethylene ketal (3).

2. The product (3), obtained in part (1), above, is heated with 14.5 g. of potassium hydroxide in 105 ml. of ethylene glycol for about 17 hours. The mixture is then allowed to cool, diluted with water and washed once with ether. The aqueous layer is then covered with ether and cautiously acidified. The organic layer separated, washed with brine and evaporated to dryness. The residue is recrystallized from cyclohexane to give 12.3 g. (77%) of 4-benzylcyclohexan-4-acetic acid-1-one ethylene ketal (4), melting at 116° to 118° C. The analytical sample has a melting point of 118° to 120° C.

Anal. Calcd. for $C_{17}H_{22}O_4$: C, 70.32; H, 7.64.

Found: C, 70.50; H, 7.83.

Following the procedure of Example 3C but substituting other 4-benzyl-4-hydroxymethylcyclohexan-1-one ethylene ketals (2) as starting materials, such as
1. 4-(o-aminobenzyl)-4-hydroxymethylcyclohexan-1-one ethylene ketal methanesulfonate (2),
2. 4-(m-fluorobenzyl)-4-hydroxymethylcyclohexan-1-one ethylene ketal methanesulfonate (2), and the like, yields, respectively,
1. 4-(o-aminobenzyl)cyclohexan-4-acetic acid-1-one ethylene ketal (4),
2. 4-(m-fluorobenzyl)cyclohexan-4-acetic acid-1-one ethylene ketal (4), and the like.

EXAMPLE 4C

4-Benzylcyclohexan-4-acetic acid-1-one (5)

A solution of 12.3 g. of 4-benzylcyclohexan-4-acetic acid-1-one ethylene ketal (4) (prepared in Example 3C) and 18 ml. of 2.5 N hydrochloric acid in 180 ml. of acetone is stirred at room temperature for about 62 hours. Most of the solvent is removed under vacuum and the residue dissolved in ether and water. The organic layer is washed with water and brine and evaporated to dryness. The residue is recrystallized from ether: Skellysolve B to give 7.94 g. (76%) of 4-benzylcyclohexan-4-acetic acid-1-one (5), having a melting point of 85° to 87° C. The analytical sample has a melting point of 91° to 92° C.

Anal. Calcd. for $C_{15}H_{18}O_3$: C, 73.15; H, 7.37.
Found: C, 73.01; H, 7.58.

Following the procedure of Example 4C but substituting other 4-benzylcyclohexan-4-acetic acid-1-one ethylene ketals (4) as starting materials, such as
1. 4-(p-ethoxybenzyl)cyclohexan-4-acetic acid-1-one ethylene ketal (4),
2. 4-(m-nitrobenzyl)cyclohexan-4-acetic acid-1-one ethylene ketal (4), and the like, yields, respectively,
1. 4-(p-ethoxybenzyl)cyclohexan-4-acetic acid-1-one (5),
2. 4-(m-nitrobenzyl)cyclohexan-4-acetic acid-1-one (5),
and the like.

EXAMPLE 5C

3',4'-Dihydrospiro[cyclohexane-1,2'(1'H)-naphthalene]-4',4-dione (6)

A solution of 6.43 g. (0.026 M) of 4-benzylcyclohexan-4-acetic acid-1-one (5) (prepared as in Example 4C) in 40 ml. of freshly distilled hydrogen fluoride is allowed to evaporate at room temperature for about 62 hours. The residue is dissolved in methylene chloride and this solution is washed successively with aqueous sodium bicarbonate solution, water and brine. The solution is evaporated to dryness and chromatographed on a colulmn of 650 ml. of silica gel and eluted with 20% acetone: Skellysolve B. The crystalline fractions are combined and recrystallized from 20% acetone: Skellysolve B to give 1.95 g. (33%) of 3',4'-dihydrospiro[cyclohexane-1,2'(1'H)-naphthalene-4',4-dione (6), having a melting point of 158° to 160° C.

Anal. Calcd. for $C_{15}H_{16}O$: C, 78.92; H, 7.06; M.W. 228.
Found: C, 78.69; H, 7.31; m/e 228.

Following the procedure of Example 5C but substituting other 4-benzylcyclohexan-4-acetic acid-1-ones (5) as starting materials, such as 1. 4-(6'-methylaminobenzyl)cyclohexan-4-acetic acid-1-one (5),
2. 4-(7'-chlorobenzyl)cyclohexan-4-acetic acid-1-one (5), and the like, yields, respectively,
1. 3',4'-dihydro[6'-methylaminospiro[cyclohexane-1,2'(1'H)-naphthalene]-1',4-dione (6),
2. 3',4'-dihydro[7'-chlorospiro[cyclohexane-1,2'-(1'H)-naphthalene]-1',4-dione (6), and the like.

EXAMPLE 6C

3',4'-Dihydrospiro[cyclohexane-1,2'(1'H)-naphthalene]-4',4-dione, 4-(ethylene ketal) (7)

A mixture of 2.65 g. (0.012 M) of 3',4'-dihydrospiro[cyclohexane-1,2'(1'H)-naphthalene]-4',4-dione (6) (prepared as in Example 5C), 0.72 g. (0.65 ml.) of ethylene glycol and 0.20 g. of p-toluenesulfonic acid in 100 ml. of benzene is heated at reflux under a Dean-Stark trap for about 14 hours. The mixture is allowed to cool, washed with aqueous sodium bicarbonate solution and brine and evaporated to dryness. The residue is chromatographed on a 300 ml. column of silica gel and eluted with 25% ethyl acetate: Skellysolve B to give 2.2 g. (70%) of 3',4'-dihydrospiro[cyclohexane-1,2'(-1'H)-naphthalene]4',4-dione, ethylene ketal (7), melting at 90° to 91.5° C.

Anal. Calcd. for $C_{17}H_{20}O_3$: C, 74.97; H, 7.40.
Found: C, 75.00; H, 7.66.

Following the procedure of Example 6C but substituting other 3',4'-dihydrospiro[cyclohexane-1,2'(-1'H)-naphthalene]-4',4-diones (6) as starting materials, such as
1. 3',4'-dihydro[5'-propoxyspiro[cyclohexane-1,2'(-1'H)-naphthalene]-1',4-dione (6),
2. 3',4'-dihydro[6'-ethylspiro[cyclohexane-1,2'-(1'H)-naphthalene]-4',4-dione (6), and the like, yields, respective
1. 3',4'-dihydro[5'-propoxyspiro[cyclohexane-1,2'(-1'H)-naphthalene]-4',4-dione, 4-(ethylene ketal) (7),
2. 3',4'-dihydro[6'-ethylspiro[cyclohexane-1,2'-(1'H)-naphthalene]-4',4-dione, 4-(ethylene ketal) (7), and the like.

EXAMPLE 7C

3',4'-Dihydrospiro[cyclohexane-1,2'(1'H)-naphthalen]-4-one, ethylene ketal (8)

A mixture of 2.2 g. (0.0081 M) of 3',4'-dihydrospiro[cyclohexane-1,2'(1'H)-naphthalene]-4',4-dione, 4-(ethylene ketal) (7) (prepared in Example 7C), 1.2 ml. of hydrazine hydrate and 1.6 g. of potassium hydroxide, is heated at reflux for about 1 hour. Solvent is removed by distillation to bring the temperature of the reaction mixture to about 200° C., and the refluxing is continued for about 17 hours, The mixture is then poured into water and extracted with ether. The organic layer is washed with water and brine and evaporated to dryness. The residue is recrystallized from petroleum ether to give 1.86 g. (88%) of 3',4'-dihydrospiro[cyclohexane-1,2'(1'H)-naphthalen] 4-one, ethylene ketal (8), having having a melting point of 79° to 81° C.

Anal. Calcd. for $C_{17}H_{22}O_2$: C, 79.03; H, 8.59.
Found: C, 79.14; H, 8.72.

Following the procedure of Example 7C but substituting other 3',4'-dihydrospiro[cyclohexane-1,2'(-1'H)-naphthalene]-4',4-dione, 4-(ethylene ketals) (7) as starting materials, such as 3',4'-dihydro[7'-nitrospiro[cyclohexane-1,2'(1'H)-naphthalene]-4',4-dione, 4-(2,2-dimethyltrimethylene ketal) (7)

yields,

3',4'-dihydro[7'-nitrospiro[cyclohexane-1,2'(1'H)-naphthalene]-4-one, ethylene ketal (8).

EXAMPLE 8C

3',4'-Dihydrospiro[cyclohexane-1,2'(1'H)-naphthalen]-4-ol (10)

1. A mixture of 1.86 g. (0.0072 mole) of 3',4'-dihydrospiro[cyclohexane-1,2'(1'H)-naphthalen]-4-one, ethylene ketal (8) (prepared in Example 7C) and 2 ml. of 2.5 N hydrochloric acid in 40 ml. of acetone is heated at reflux for about 17 hours. Most of the solvent is removed under vacuum and the residue dissolved in water and ether. The organic layer is washed with water and brine and then evaporated to dryness to give 3',4'-dihydrospiro[cyclohexane-1,2'(1'H)-naphthalen]-4-one (9).

2. The residue (9), obtained in part (1), above, is dissolved in 50 ml. of 95% isopropanol and treated with 1 g. of sodium borohydride. After about 5 hours the solvent is removed under vacuum and the residue dissolved in water and ether. The organic layer is washed with water and brine, evaporated to dryness, the crude produce chromatographed on a 170 ml. column of silica gel and eluted with methylene chloride. There is first obtained 0.24 g. of starting material (8). The product fractions are combined and recrystallized from Skellysolve B to give 0.65 g. (42%) of 3',4'-dihydrospiro[cyclohexane-1,2'(1'H)-naphthalen]-4-ol (10), melting at 78° to 82° C.

Anal. Calcd. for $C_{15}H_{20}O$: C, 82.28; H, 9.32. M.W. 216.

Found: C, 83.37; H, 9.43, m/e 216.

Following the procedure of Example 8C but substituting other 3',4'-dihydrospiro[cyclohexane-1,2'(-1'H)-naphthalen]-4-one, ethylene ketals (8) as starting materials, such as 3',4'-dihydro[6'-fluorospiro[cyclohexane-1,2'(1'H)-naphthalen]-4-one, 2,2-dimethyltriethylene ketal (8), yields, 3',4'-dihydro[6'-fluorospiro[cyclohexane-1,2'(1'H)-naphthalen]-4-ol (10).

EXAMPLE 9C

3',4'-Dihydrospiro[cyclohexane-1,2'(1'H)-naphthalen]-4-ol methanesulfonate (11)

To an ice cold solution of 2.16 g. (0.01 M) of 3',4'-dihydrospiro[cyclohexane-1,2'(1'H)-naphthalen]-4-ol (10) (prepared as in Example 8C) in 10 ml. of pyridine, 2 ml. of methanesulfonyl chloride is added. After about 4 hours in the cold, the mixture is poured onto ice: water. The resulting solid precipitate is collected on a filter and recrystallized from ether: petroleum ether to give 2.52 g. (86%) of 3',4'-dihydrospiro[cyclohexane-1,2'(1'H)-naphthalen]-4-ol methansulfonate (11), melting at 66° to 69° C.

Anal. Calcd. for $C_{16}H_{22}O_3S$: C, 65.27; H, 7.53

Found: C, 65.38; H, 7.54.

Following the procedure of Example 9C but substituting other 3',4'-dihydrospiro[cyclohexane-1,2'(-1'H)-naphthalen]-4-ols (10) and other lower alkyl sulfonyl halides as starting materials, such as 3',4'-dihydro[5'-ethoxyspiro[cyclohexane-1,2'(-1'H)-naphthalen]-4-ol (10) and propane sulfonyl bromide, yields, 3',4'-dihydro[5'-ethoxyspiro[cyclohexane-1,2'(-1'H)-naphthalen]-4-ol propanesulfonate (11).

EXAMPLE 10C

3',4'-Dihydrospiro[cyclohexane-1,2'(1'H)-naphthalen]-4-ylamine hydrochloride [I(c)]

A mixture of 2.52 g. (0.0085 M) of 3',4'-dihydrospiro[cyclohexane-1,2'(1'H)-naphthalen]-4-ol methanesulfonate (11) (prepared in Example 9C) and 2.5 g. of sodium azide in 25 ml. of dimethylformamide is heated for about 17 hours in an oil bath at about 90° C. The solvent is then removed under vacuum and the residue, 3',4'-dihydrospiro[cyclohexane-1,2'(1'H)-napthalen]-4-ylazide, dissolved in benzene and water. The organic layer is washed with water and brine and evaporated to dryness. A solution of the residue in 60 ml. of tetrahydrofuran is added to 0.35 g. of lithium aluminum hydride in 10 ml. of tetrahydrofuran. After stirring for about 4 hours at room temperature, the mixture is cooled in ice and treated successively with 0.35 ml. of water, 0.35 ml. of aqueous 15% sodium hydroxide solution and 1.05 ml. of water. The resulting inorganic gel is collected on a filter and the filtrate evaporated to dryness. A solution of the residue in ether is treated with 6 N hydrogen chloride in ether. The resulting solid is recrystallized from methylene chloride: ethyl acetate to give 1.65 g. (77%) of 3',4'-dihydrospiro[cyclohexane-1,2'(1'H)-naphthalen]-4-ylamine hydrochloride [I(c)], melting at 208° to 211° C.

Following the procedure of Example 10C but substituting other 3',4'-dihydrospiro[cyclohexane-1,2'(1'-H)-naphthalen]-4-ol lower alkylsulfonates (11) as starting materials, such as 3',4'-dihydro[6'-fluorospiro[cyclohexane-1,2'(1'H)-naphthalen]-4-ol propanesulfonate (11), yields, 3',4'-dihydro[6'-fluorospiro[cyclohexane-1,2'(1'H)-naphthalen]-4-ylamine hydrochloride [I(c)].

EXAMPLE 11C

1-[3',4'-dihydrospiro[cyclohexane-1,2'(1'H)-naphthalen]-4-yl]piperidine [I(c)]

The amine prepared from 1.5 g. of 3',4'-dihydrospiro[cyclohexane-1,2'(1'H)-naphthalen]-4-ylamine hydrochloride [I(c)] (prepared as in Example 10C), 1.9 g. of 1,5-diiodopentane and 1.6 g. of potassium carbonate in 18 ml. of ethanol is stirred at reflux temperature for about 18 hours. The mixture after cooling is diluted with water, the solid collected on a filter and recrystallized from methanol to give 1-[3',4'-dihydrospiro[cyclohexane-1,2'(1'H)-naphthalen]-4-yl]piperidine [I(c)].

Following the procedure of Example 11C but substituting acid addition salts of the same and other 3',4'-dihydrospiro[cyclohexane-1,2'(1'H)-naphthalen]-4-ylamines [I(c)] and other dihaloalkanes, such as 1. 3',4'-dihydrospiro[cyclohexane-1,2'(1'H)-naphthalen]-4-ylamine [I(c)] and 1,4-diiodobutane,
2. 3',4'-dihydrospiro[cyclohexane-1,2'(1'H)-naphthalen]-4-ylamine [I(c)] and 1,6-diiodohexane,
3. 5'-bromospiro[cyclohexane-1,2'(1'H)-naphthalen]-4-ylamine [I(c)] and 1,5-diiodopentane and the like, yields respectively, 1. 1-[3',4'-dihydrospiro[cyclohexane-1,2'(1'H)-naphthalen]-4-yl pyrrolidine [I(c)],
2. 1-[3',4'-dihydrospiro[cyclohexane-1,2'(1'H)-naphthalen]-4-yl hexamethyleneimine [I(c)], 3. 1-[5'-bromospiro[cyclohexane-1,2'(1'H)-naphthalen]-4-yl piperidine [I(c)], and the like.

EXAMPLE 12C

4'-Fluoro-4-[[3',4'-dihydrospiro[cyclohexane-1,2'(-1'H)-naphthalen]-4-yl]amino]butyrophenone hydrochloride [I(c)]

The free base from 1.65 g. (0.0066 M) of 3',4'-dihydrospiro[cyclohexane-1,2'(1'H)-naphthalen]-4-ylamine hydrochloride [I(c)] (prepared in Example 10C), 1.34 g. of potassium iodide, 2.06 g. of potassium carbonate and 1.9 g. of the 2,2-dimethyl-1,3-propanediol ketal of 4-chloro-4'-fluorobutyrophenone in 35 ml. of dimethylformamide are heated in an oil bath at about 90° C. for about 18 hours. The solvent is removed under vacuum and the residue that remains in dissolved in benzene and water. The organic layer is washed with water and brine and evaporated to dryness. A mixture of the residue and 10 ml. of 2.5 N hydrochloric acid in 20 ml. of methanol is stirred at room temperature for about 4 hours. The methanol is then removed under vacuum and the solid collected on a filter. This material is recrystallized twice from methylene chloride: ethyl acetate to give 1.07 g. (39% yield) of 4'-fluoro-4-[[3',-4'-dihydrospiro[cyclohexane-1,2'(1'H)-naphthalen]-4-yl]amino]butyrophenone hydrochloride [I(c), having a melting point of 182° to 184° C.

Anal. Calcd for $C_{25}H_{31}ClFNO$: C, 72.18; H, 7.51; N, 3.37; M.W. 379.

Found: C, 72.20; H, 7.53; N, 3.47; m/e 379.

Following the procedure of Example 12C but substituting another 3',4'-dihydrospiro[cyclohexane-1,2'(-1'H)-naphthalen]-4-ylamine [I(c)] as starting material and the 2,2-dimethyl-1,3-propanediol ketal of another ω-haloalkanaryl ketone, such as 5'-bromospiro[cyclohexane-1,2'(1'H)-naphthalen]-4-ylamine hydrochloride [I(c)] and the 2,2-dimethyl-1,3-propanediol ketal of 4'-bromo-4-chlorobutyrophenone, yields, 4'-bromo-4-[[5'-bromospiro[cyclohexane-1,2'(-1'H)-naphthalen]-4-yl]amino]butyrophenone hydrochloride [I(c)].

EXAMPLE 13C

Ethyl 3',4'-dihydrospiro[cyclohexane-1,2'(1'H)-naphthalene]-4-carbamate [I(c)]

To an ice cooled solution of the free base prepared from 1.5 g. of 3',4'-dihydrospiro[cyclohexane-1,2'(-1'H)-naphthalen]-4-ylamine hydrochloride [I(c)] (prepared as in Example 10C) in 12 ml. of pyridine, 1 ml. of ethyl chloroformate is added. The mixture is allowed to stand in the cold for about 5 hours and then poured into ice water. The solid that precipitates is collected on a filter and recrystallized from methylene chloride: benzene to give ethyl 3',4'-dihydrospiro[cyclohexane-1,2'(1'H)-naphthalene]-4-carbamate [I(c)].

Following the procedure of Example 13C but substituting another 3',4'-dihydrospiro[cyclohexane-1,2'(-1'H)-naphthalen]-4-ylamine [I(c)] as starting material and another lower alkyl haloformate, such as 5'-ethoxyspiro[cyclohexane-1,2'(1'H)-naphthalen]-4-ylamine [I(c)] and propyl bromoformate, and the like, yields, propyl 5'-ethoxyspiro[cyclohexane-1,2'(1'H)-naphthalene]-4-carbamate [I(c)].

EXAMPLE 14C

3',4'-Dihydrospiro[cyclohexane-1,2'(1'H)-naphthalen]-4-yl-N-methylamine hydrochloride [I(c)]

To a suspension of 0.22 g. of lithium aluminum hydride in 10 ml. of tetrahydrofuran, a tetrahydrofuran solution of 1.3 g. of ethyl 3',4'-dihydrospiro[cyclohexane-1,2'(1'H)-naphthalene]-4-carbamate [I(c)] (prepared as in Example 13C) is added. The mixture is stirred at reflux temperature for about 6 hours, at room temperature for about 18 hours, and cooled in an ice bath. To this is added successively, 0.22 ml. of water, 0.22 ml. of 15% aqueous sodium hydroxide solution and 0.66 ml. of water. The resulting inorganic gel is collected on a filter, rinsed with ether and the filtrates evaporated to dryness. The residue is dissolved in a small amount of ether and treated with an excess of 6.4 N hydrogen chloride in ether. The resulting precipitate is collected on a filter and recrystallized from methanol: ethyl acetate to give 3',4'-dihydrospiro[cyclohexane-1,2'(1'H)-naphthalen]-4-yl-N-methyl-amine hydrochloride [I(c)].

Following the procedure of Example 14C but substituting another lower alkyl 3',4'-dihydrospiro[cyclohexane-1,2'-(1'H)-naphthalene]-4-carbamate [I(c)] as starting material, such as ethyl 5'-isopropylspiro[cyclohexane-1,2'(1'H)-naphthalen]-4-carbamate [I(c)], yields, 5'-isopropylspiro[cyclohexane-1,2'(1'H)-naphthalen]-4-yl-N-methylamine hydrochloride [I(c)].

EXAMPLE 15C

4'-Fluoro-4-[3',4'-dihydrospiro[cyclohexane-1,2'(-1'H)-naphthalen]-4-yl-N-methylamino]-butyrophenone hydrochloride [I(c)]

A mixture of the free base prepared from 0.81 g. of 3',4'-dihydrospiro[cyclohexane-1,2'(1'H)-naphthalen]-4-yl-N-methylamine hydrochloride [I(c)] (obtained as in Example 14C), 0.63 g. of potassium iodide, 0.96 g. of potassium carbonate and 0.87 g. of the 2,2-dimethyl-1,3-propanediol ketal of 4-chloro-4'-fluorobutyrophenone in 15 ml. of dimethylformamide is heated together in an oil bath at about 90° C. for about 20 hours. The solvent is removed under vacuum and the residue dissolved in water and benzene. The organic layer is washed with water and brine and evaporated to dryness. A mixture of the residue, 6 ml. of 2.5 N hydrochloric acid and 12 ml. of methanol is stirred at room temperature for about 1.5 hours and most of the methanol removed under vacuum. The residual suspended solid is collected on a filter, washed with ether and recrystallized from methanol: ethyl acetate to give 4'-fluoro-4-[3',4'-dihydrospiro[cyclohexane-1,2'(-1'H)-naphthalen]-4-yl-N-methylamino]butyrophenone hydrochloride [I(c)].

Following the procedure of Example 15C but substituting another 3',4'-dihydrospiro[cyclohexane-1,2'(-1'H)-naphthalen]-4-yl-N-lower alkylamine [I(c)] as starting material and the 2,2-dimethyl-1,3-propanediol ketal of another ω-haloalkanaryl ketone, such as 1. 6'-bromospiro(cyclohexane-1,2'(1'H)-naphthalen]-4-yl-N-methylamine [I(c)] and the 2,2-dimethyl-1,3-propanediol ketal of 4-chloro-4'-methoxybutyrophenone, 2. 5'-propoxyspiro[cyclohexane-1,2'(1'H)-naphthalen]-4-yl-N-ethylamine [I(c)] and the 2,2-dimethyl-1,3-propanediol ketal of 4-chloro-2'-ethylbutyrophenone, and the like.

yields, respectively,
1. 4'-methoxy-4-[6'-bromospiro[cyclohexane-1,2'(-1'H)-naphthalen]-4-yl-N-methylamino]butyrophenone hydrochloride [I(c)],
2. 2'-ethyl-4-[5'-propoxyspiro[cyclohexane-1,2'(-1'H)-naphthalen]-4-yl-N-ethylamino]butyrophenone hydrochloride [I(c)], and the like.

I claim:
1. A compound of the formula

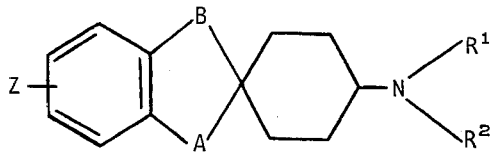

wherein the sum of A and B carbon atoms is at least the integer 2; A is $-(CH_2)_n-$ wherein $n$ is 1 through 5; B is absent or $-(CH_2)_n-$ wherein $n$ is 1 through 3; $R^1$ is selected from the group consisting of hydrogen and lower alkyl of 1 through 3 carbon atoms; $R^2$ is selected from the group consisting of hydrogen, lower alkyl of 1 through 3 carbon atoms, $R^1$ and $R^2$ taken together with $-N<$ is a saturated heterocyclic amino radical selected from the group consisting of pyrrolidino, piperidino, and hexamethylenimino; Z is selected from the group consisting of hydrogen, lower alkyl of 1 through 3 carbon atoms, lower alkoxy of 1 through 3 carbon atoms, nitro, amino, monoalkylamino of 1 through 3 carbon atoms, alkanoylamido of 1 through 4 carbon atoms, bromine, chlorine and fluorine; and a pharmacologically acceptable acid addition salt thereof.

2. A compound of claim 1 wherein A is $-(CH_2)_N-$ wherein $n$ is 3, B is absent, $R^1$, $R^2$ and Z are hydrogen and the pharmacologically acceptable acid addition salt is that of hydrochloric acid, namely, 3',4'-dihydrospiro(cyclohexane-1,1'-(2'H)-naphthalen)-4-ylamine hydrochloride.

3. A compound of claim 1 wherein A is $-(CH_2)_n-$ wherein $n$ is 3, B is absent, $R^1$ is methyl, $R^2$ and Z are hydrogen and the pharmacologically acceptable acid addition salt is that of hydrochloric acid, namely, 3',4'-dihydrospiro(cyclohexane-1,1'(2'H)-naphthalen)-4-yl-N-methylamine hydrochloride.

4. A compound of claim 1 wherein A and B are $-(CH_2)_n-$ wherein $n$ is 1, $R^1$, $R^2$ and Z are hydrogen and the pharmacologically acceptable acid addition salt is that of hydrochloric acid, namely, spiro(cyclohexane-1,2'-indan)-4-amine hydrochloride.

5. A compound of claim 1 wherein A and B are $-(CH_2)_n-$ wherein $n$ is 1, $R^1$ is methyl, $R^2$ and Z are hydrogen and the pharmacologically acceptable acid addition salt is that of hydrochloric acid, namely, spiro(cyclohexane-1,2'-indan)-4-methylamine hydrochloride.

6. A compound of claim 1 wherein A and B are $-(CH_2)_n-$ wherein $n$ is 1, $R^1$ is methyl, $R^2$ is hydrogen, Z is 5'-methyl and the pharmacologically acceptable acid addition salt is that of hydrochloric acid, namely, 5'-methylspiro(cyclohexane-1,2'-indan)-4-amine hydrochloride.

7. A compound of claim 1 wherein A and B are $-(CH_2(_n-$ wherein $n$ is 1, $R^1$ and $R^2$ are hydrogen, Z is 5'-methoxy and the pharmacologically acceptable acid addition salt is that of hydrochloric acid, namely, 5'-methoxyspiro(cyclohexane-1,2'-indan)-4-amine hydrochloride.

8. A compound of claim 1 wherein A and B are $-(CH_2)_n-$ wherein $n$ is 1, $R^1$ and $R^2$ are hydrogen, Z is 5'-acetamido and the pharmacologically acceptable acid addition salt is that of hydrochloric acid, namely, N-[4-aminospiro[cyclohexane-1,2'-indan]-5'-yl]acetamide hydrochloride.

9. A compound of claim 1 wherein A and B are $-(CH_2)_n-$ wherein for A $n$ is 2 and for B $n$ is 1, $R^1$, $R^2$ and Z are hydrogen and the pharmacologically acceptable acid addition salt is that of hydrochloric acid, namely, 3',4'-dihydrospiro(cyclohexane-1,2'(1'H)-naphthalen)-4-ylamine hydrochloride.

10. A compound of claim 1 wherein A and B are $-(CH_2)_n-$ wherein $n$ is 1, $R^1$ and $R^2$ taken together with $-N<$ is piperidino, Z is hydrogen and the pharmacologically acceptable acid addition salt is that of hydrochloric acid, namely, 1-[spiro(cyclohexane-1,2'-indane)-4-yl]-piperidine hydrochloride.

* * * * *